(12) United States Patent
Lagu et al.

(10) Patent No.: US 8,236,819 B2
(45) Date of Patent: Aug. 7, 2012

(54) DIHYDRO-[1H]-QUINOLIN-2-ONE DERIVATIVES AS RXR AGONISTS FOR THE TREATMENT OF DYSLIPIDEMIA, HYPERCHOLESTEROLEMIA AND DIABETES

(75) Inventors: Bharat Lagu, Hillsborough, NJ (US); Rimma Lebedev, Basking Ridge, NJ (US); Barbara Pio, Hillsborough, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 251 days.

(21) Appl. No.: 12/617,776

(22) Filed: Nov. 13, 2009

(65) Prior Publication Data
US 2010/0105728 A1    Apr. 29, 2010

Related U.S. Application Data

(62) Division of application No. 11/534,928, filed on Sep. 25, 2006, now Pat. No. 7,638,533.

(60) Provisional application No. 60/722,218, filed on Sep. 30, 2005.

(51) Int. Cl.
*A61K 31/47* (2006.01)
*C07D 215/20* (2006.01)

(52) U.S. Cl. ........ 514/312; 546/112; 546/152; 546/157; 514/299; 514/311

(58) Field of Classification Search .................. 546/112, 546/152, 157; 514/299, 312
See application file for complete search history.

(56) References Cited

U.S. PATENT DOCUMENTS

| | | | |
|---|---|---|---|
| 5,739,338 A | 4/1998 | Beard et al. | |
| 6,048,873 A | 4/2000 | Vasudevan et al. | |
| 6,734,193 B1 | 5/2004 | Duong et al. | |
| 7,071,218 B2 | 7/2006 | Pfahl et al. | |
| 7,196,108 B2 | 3/2007 | Pfahl et al. | |
| 7,265,139 B2 | 9/2007 | Tachdjian et al. | |
| 7,638,533 B2 * | 12/2009 | Lagu et al. | 514/312 |
| 7,723,326 B2 * | 5/2010 | Lagu et al. | 514/230.5 |

FOREIGN PATENT DOCUMENTS

| | | |
|---|---|---|
| EP | 1117648 | 8/2003 |
| WO | WO 03/075924 | 9/2003 |

OTHER PUBLICATIONS

PCT International Search Report No. PCT/US2006/037545 dated May 23, 2007 which relates to U.S. Appl. No. 11/534,928.

Unger et al., "Hyperglycaemia as an inducer as well as a consequence of impaired isle cell function and insulin resistance: implications for the management of diabetes.", Diabetologia, 1985, vol. 28, pp. 119-121.

Rosetti et al., "Glucose Toxicity.", Diabetes Cares, 1990, vol. 13(6), pp. 610-630, *abstract only*.

Mangelsdorf et al., "The RXR Heterodimers and Orphan Receptors.", Cell, 1995, vol. 83, pp. 841-850.

Kastner et al., "Nonsteroid Nuclear Receptors: What are Genetic Studies Telling Us about Their Role in Real Life ?", Cell,, 1995, vol. 83, pp. 859-869.

Hibi et al., "Syntheses and Structure-Activity Relationships of Novel Retinoid X Receptor.", Journal of Medicinal Chemistry, 1998, vol. 41(17), pp. 3245-3252, American Chemical Society, XP002131548, ISSN: 0022-2623.

Haffner et al., "Structure-Based Design of Potent Retinoid X Receptor α Agonists.", Journal of Medicinal Chemistry, 2004, vol. 47(8), pp. 2010-2029, XP002415204, ISSN: 0022-2623.

Pogenberg et al., "Characterization of the Interaction between Retinoic Acid Receptor/Retinoin X Receptor (RAR,RXR) Heterodimers and Transcriptional Coactivators through Structural and Fluorescence Anisotropy Studies.", Journal of Biological Chemistry, 2005, Vo. 280(2), pp. 1625-1633, XP002415142, ISSN: 0021-9258.

Denmark et al., "Cyclopropanation with Diazomethane and Bis(oxazoline)palladium(II) Complexes.", Journal of Organic Chemistry, 1997, vol. 62(10), pp. 3375-3389.

Charette et al., "Bis(oxazoline)•copper(I)-catalyzed enantioselective cyclopropanation of cinnamate esters with diazomethane.", Tetrahedron: Asymmetry, 2003, vol. 14(7), pp. 867-872.

Eilbracht et al., Tandem silylformylation/Wittig Olefination of Terminal Alkynes: Stereoselective Synthesis of 2,4-Dienoic Esters., European Journal of Organic Chemistry, 2000(7), pp. 1131-1135.

* cited by examiner

*Primary Examiner* — Golam M M Shameem

(57) ABSTRACT

The present invention relates to compounds of Formula (I),

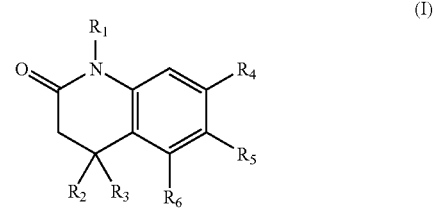

(I)

methods for preparing these compounds, compositions, intermediates and derivatives thereof and for treating RXR mediated disorders. More particularly, the compounds of the present invention are RXR agonists useful for treating RXR mediated disorders.

5 Claims, No Drawings

DIHYDRO-[1H]-QUINOLIN-2-ONE DERIVATIVES AS RXR AGONISTS FOR THE TREATMENT OF DYSLIPIDEMIA, HYPERCHOLESTEROLEMIA AND DIABETES

CROSS REFERENCE TO RELATED APPLICATION

This Application is a divisional application of U.S. application Ser. No. 11/534,928, filed Sep. 25, 2006, which claims priority to U.S. Provisional Patent Application No. 60/722,218, filed Sep. 30, 2005, the disclosures of which are hereby incorporated by reference in their entireties.

FIELD OF THE INVENTION

The present invention relates to certain novel compounds, methods for preparing compounds, compositions, intermediates and derivatives thereof and for treating cancer and metabolic disorders. More particularly, the compounds of the present invention are Retinoid X Receptor (RXR) agonists useful for treating, ameliorating or inhibiting the onset of cancer and metabolic disorders such as diabetes, dyslipidemia, and hypercholesterolemia.

BACKGROUND OF THE INVENTION

Diabetes is a chronic disorder affecting carbohydrate, fat and protein metabolism in animals.

Type I diabetes mellitus, which comprises approximately 10% of all diabetes cases, was previously referred to as insulin-dependent diabetes mellitus ("IDDM") or juvenile-onset diabetes. This disease is characterized by a progressive loss of insulin secretory function by beta cells of the pancreas. This characteristic is also shared by non-idiopathic, or "secondary," diabetes having its origins in pancreatic disease. Type I diabetes mellitus is associated with the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Type II diabetes mellitus (non-insulin-dependent diabetes mellitus or NIDDM) is a metabolic disorder involving the dysregulation of glucose metabolism and impaired insulin sensitivity. Type II diabetes mellitus usually develops in adulthood and is associated with the body's inability to utilize or make sufficient insulin. In addition to the insulin resistance observed in the target tissues, patients suffering from type II diabetes mellitus have a relative insulin deficiency—that is, patients have lower than predicted insulin levels for a given plasma glucose concentration. Type II diabetes mellitus is characterized by the following clinical signs or symptoms: persistently elevated plasma glucose concentration or hyperglycemia; polyuria; polydipsia and/or hyperphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Dyslipidemia, or dislipidemia, includes lipoprotein overproduction or deficiency; sometimes associated with diabetes, it is a common cause of lipidemia. For example, it is recommended for adults with diabetes to have their levels of LDL, HDL, total cholesterol, and triglyceride measured regularly. The desirable levels for such adults can be: LDL—less than 100 mg/dL (2.60 mmol/L), HDL—no less than 40 mg/dL (1.02 mmol/L), and triglyceride—less than 150 mg/dL (1.7 mmol/L). When blood cholesterol is too high, the condition is referred to as hypercholesterolemia. In one instance, dyslipidemia can include hypertriglyceridemia, and mixed hyperlipidemia. In terms of the above indices, dyslipidemia (including hyperlipidemia) may be one or more of the following conditions: low HDL (<35 or 40 mg/dl), high triglycerides (>200 mg/dl), and high LDL (>150 mg/dl).

Compounds having retinoid-like activity are useful for preventing, treating or at least alleviating the symptoms and conditions of numerous diseases and conditions. There are two main types of retinoid receptors: the Retinoid X Receptors (RXRs) including their subtypes RXRα, β, γ, and the Retinoic Acid Receptors (RARs), also including their subtypes RARα, β, γ. Retinoid receptor modulators are useful in a variety of conditions including, but not limited to, metabolic disorders, such as type II diabetes, dyslipidemia, hypercholesterolemia, and atherosclerosis, and various cancerous and precancerous conditions in the breast, skin, prostate, cervix, uterus, colon, bladder, esophagus, stomach, lung, larynx, oral cavity, blood and/or lymphatic systems. For example, RXRs belong to the nuclear receptor superfamily and consist of a large number of ligand-regulated transcription factors that mediate the diverse physiological functions of steroid hormones, retinoids, thyroid hormone, and vitamin D in embryonic development, growth, differentiation, apoptosis, and homeostasis (Mangelsdorf, D. J., et al., Cell 83, 841-850 (1995); Kastner, P., et al., Cell 83, 859-869 (1995)).

RXR modulators have been identified as insulin sensitizing drugs. All diabetics, regardless of their genetic and environmental backgrounds, have in common an apparent lack of insulin or inadequate insulin function. Because transfer of glucose from the blood into muscle and fatty tissue is insulin dependent, diabetics lack the ability to utilize glucose adequately, which leads to undesired accumulation of glucose in the blood, or hyperglycemia. Chronic hyperglycemia leads to decrease in insulin secretion and contributes to increased insulin resistance, and as a result, the blood glucose concentration is increased so that diabetes is self-exacerbated (Diabetologia, 1985, "Hyperglycaemia as an inducer as well as a consequence of impaired isle cell function and insulin resistance: implications for the management of diabetes", Vol. 28, p. 119); Diabetes Cares, 1990, Vol. 13, No. 6, "Glucose Toxicity", pp. 610-630). Therefore, by treating hyperglycemia, the aforementioned self-exacerbating cycle can be interrupted so that prophylaxis or treatment of diabetes is made possible.

U.S. Pat. No. 6,048,873 to Vasudevan et al. is directed to novel compounds having retinoid-like biological activity. More specifically, it is directed to compounds that include a substituted tetrahydroquinoline moiety and a 2,4-pentadienoic acid moiety and have selective activity for retinoid X receptors.

U.S. Pat. No. 5,739,338 to Beard et al. is directed to novel compounds having retinoid antagonist and/or retinoid inverse-agonist-like biological activity. More specifically, it is directed to aryl substituted tetrahydroquinoline derivatives which bind to retinoid receptors and have retinoid-like, retinoid antagonist or retinoid inverse agonist-like biological activity.

There is a continuing need for new RXR agonists. There is also a need for RXR agonists useful for the treatment of conditions including but not limited to cancer and metabolic disorders such as diabetes, dyslipidemia, and hypercholesterolemia.

SUMMARY OF THE INVENTION

In its many embodiments, the present invention provides a novel class of compounds useful as, for example, retinoid x receptor agonists, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with the retinoid x receptors using such compounds or pharmaceutical compositions.

One aspect of the present invention features a compound of Formula (I)

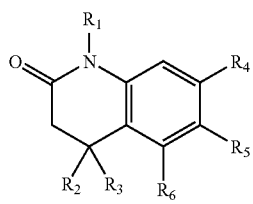

(I)

wherein
 $R_1$ is H or optionally substituted $C_{1-3}$alkyl;
 $R_2$ and $R_3$ are independently $C_{1-3}$alkyl;
 $R_4$ is

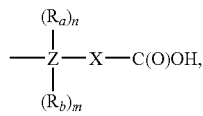

wherein
 Z is selected from

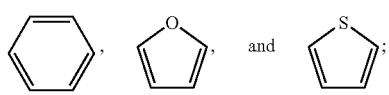

X is selected from a bond, optionally substituted —O—$C_{1-5}$alkyl-, and optionally substituted $C_{1-6}$alkylene;
 $R_a$ and $R_b$ are independently selected from optionally substituted $C_{1-3}$alkyl, optionally substituted —$C_{2-3}$alkenyl, and optionally substituted $C_{1-3}$alkoxy; and
 m and n are independently selected from 0, 1, and 2, except that m and n can not both be 2;
 or alternatively $R_4$ is H or optionally substituted $C_{1-3}$alkyl;
 with the proviso that when $R_4$ is

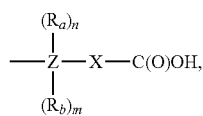

then $R_5$ cannot be

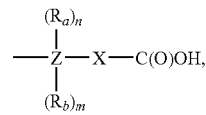

provided further that when $R_4$ is H or optionally substituted $C_{1-3}$alkyl, then $R_5$ cannot be H or optionally substituted $C_{1-3}$alkyl;
 $R_5$ is

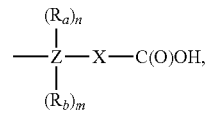

wherein
 Z is selected from

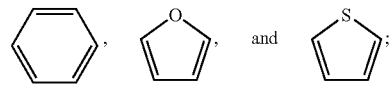

X is selected from a bond, optionally substituted —O—$C_{1-5}$alkyl-, and optionally substituted $C_{1-6}$alkylene;
 $R_a$ and $R_b$ are independently selected from optionally substituted $C_{1-3}$alkyl, optionally substituted —$C_{2-3}$alkenyl, and optionally substituted $C_{1-3}$alkoxy; and
 m and n are independently selected from 0, 1, and 2, except that m and n can not both be 2;
 or alternatively $R_5$ is H or optionally substituted $C_{1-3}$alkyl;
 with the proviso that when $R_5$ is

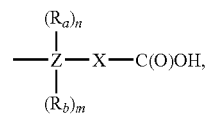

then $R_4$ cannot be

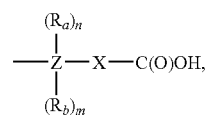

provided further that when $R_5$ is H or optionally substituted $C_{1-3}$alkyl, then $R_4$ cannot be H or optionally substituted $C_{1-3}$alkyl; and
 $R_6$ is H or $C_{1-3}$alkyl;
or an optical isomer, enantiomer, diastereomer, racemate, or pharmaceutically acceptable salt thereof.

Another aspect of the present invention features a pharmaceutical composition comprising at least one compound of Formula (I) and at least one pharmaceutically acceptable carrier.

One embodiment of the invention is a method for treating, preventing or ameliorating a RXR mediated condition in a subject in need thereof comprising administering to the subject a therapeutically effective amount of at least one compound of Formula (I). Particularly, it is an embodiment of the invention to provide a method for treating, preventing or ameliorating a condition selected from cancer, diabetes, dyslipidemia, hypercholesterolemia, and associated symptoms or complications thereof in a subject in need thereof, comprising administering to said subject a therapeutically effective amount of (a) at least one compound of Formula (I); and (b) at least one additional agent selected from a retinoid receptor agonist, an anti-diabetic agent, a lipid lowering agent, an anti-thrombotic agent, and a blood pressure lowering agent, said co-administration being in any order. In one embodiment the additional agent is a RXR agonist.

Another embodiment of the invention is a method for inhibiting the onset of a RXR condition in a subject in need thereof, comprising administering to said subject a therapeutically effective amount of (a) at least one compound of Formula (I); and (b) at least one additional agent selected from a retinoid receptor agonist, an anti-diabetic agent, a lipid lowering agent, an anti-thrombotic agent, and a blood pressure lowering agent, said co-administration being in any order and the combined amounts providing the desired prophylactic effect. In one embodiment the additional agent is a RXR agonist.

It is a further embodiment of the invention to provide a process for making a pharmaceutical composition comprising admixing any of the compounds according to Formula (I) and a pharmaceutically acceptable carrier.

In the disclosed methods, the diabetes, dyslipidemia, hypercholesterolemia, and associated symptoms or complications thereof can be selected, for example, from IDDM, NIDDM, IGT (Impaired Glucose Tolerance), IFG (Impaired Fasting Glucose), Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts.

Another aspect of the invention relates to treating hypertriglyceridemia, raising levels of HDL, lowering levels of LDL, and/or lowering total cholesterol.

Additional embodiments and advantages of the invention will become apparent from the detailed discussion, examples, and claims below.

DETAILED DESCRIPTION OF THE INVENTION

This invention relates to novel RXR agonists and compositions thereof for treatment or prophylaxis of conditions such as diabetes, dyslipidemia, and hypercholesterolemia, and associated symptoms or complications thereof.

One aspect of the present invention features a compound of Formula (I)

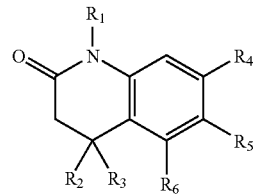

(I)

wherein $R_1$ is H or optionally substituted $C_{1-3}$alkyl;

$R_2$ and $R_3$ are independently $C_{1-3}$alkyl;

$R_4$ is

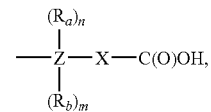

wherein

Z is selected from

X is selected from a bond, optionally substituted —O—$C_{1-5}$alkyl-, and optionally substituted $C_{1-6}$alkylene;

$R_a$ and $R_b$ are independently selected from optionally substituted $C_{1-3}$alkyl, optionally substituted —$C_{2-3}$alkenyl, and optionally substituted $C_{1-3}$alkoxy; and m and n are independently selected from 0, 1, and 2, except that m and n can not both be 2;

or alternatively $R_4$ is H or optionally substituted $C_{1-3}$alkyl;

with the proviso that when $R_4$ is

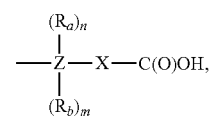

then $R_5$ cannot be

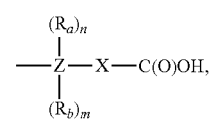

provided further that when $R_4$ is H or optionally substituted $C_{1-3}$alkyl, then $R_5$ cannot be H or optionally substituted $C_{1-3}$alkyl;

$R_5$ is

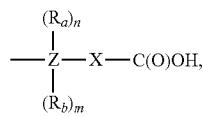

wherein

Z is selected from

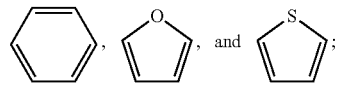

X is selected from a bond, optionally substituted —O—$C_{1-5}$alkyl-, and optionally substituted $C_{1-6}$alkylene;

$R_a$ and $R_b$ are independently selected from optionally substituted $C_{1-3}$alkyl, optionally substituted —$C_{2-3}$alkenyl, and optionally substituted $C_{1-3}$alkoxy; and m and n are independently selected from 0, 1, and 2, except that m and n can not both be 2;

or alternatively $R_5$ is H or optionally substituted $C_{1-3}$alkyl;

with the proviso that when $R_5$ is

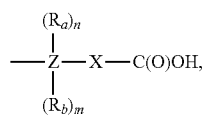

then $R_4$ cannot be

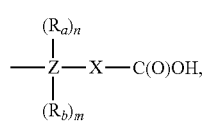

provided further that when $R_5$ is H or optionally substituted $C_{1-3}$alkyl, then $R_4$ cannot be H or optionally substituted $C_{1-3}$alkyl; and $R_6$ is H or $C_{1-3}$alkyl;

or an optical isomer, enantiomer, diastereomer, racemate, or pharmaceutically acceptable salt thereof.

Particularly, the present invention features a compound of Formula (I) wherein $R_1$ is H or $C_{1-3}$alkyl.

Particularly, the present invention features a compound of Formula (I) wherein $R_2$ and $R_3$ are —$CH_3$.

Particularly, the present invention features a compound of Formula (I) wherein $R_4$ or $R_5$ is

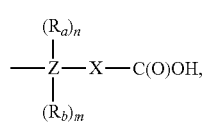

wherein Z is

More particularly, Z is

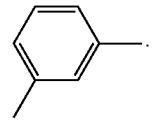

Particularly, the present invention features a compound of Formula (I) wherein $R_4$ or $R_5$ is

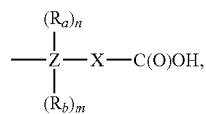

wherein Z is

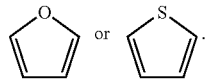

More particularly, Z is

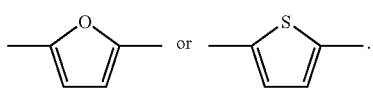

Particularly, the present invention features a compound of Formula (I) wherein $R_4$ or $R_5$ is

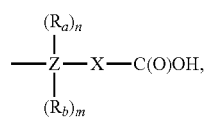

wherein X is a bond.

Particularly, the present invention features a compound of Formula (I) wherein $R_4$ or $R_5$ is

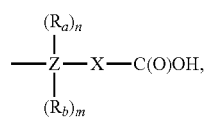

wherein X is optionally substituted —O—$C_{1-5}$alkyl-. More particularly, the $C_{1-5}$alkyl- is saturated. More particularly, the $C_{1-5}$alkyl- is

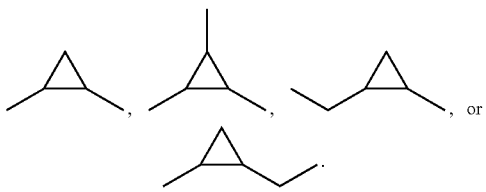

More particularly, 1, 2, or 3 of the hydrogen atoms in the $C_{1-5}$alkyl- is further substituted by halogen. Particularly, the halogen is F.

Particularly, the present invention features a compound of Formula (I) wherein $R_4$ or $R_5$ is

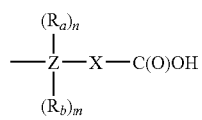

wherein X is optionally substituted $C_{1-6}$alkylene. More particularly, the $C_{1-6}$alkylene is saturated. More particularly, the $C_{1-6}$alkylene is

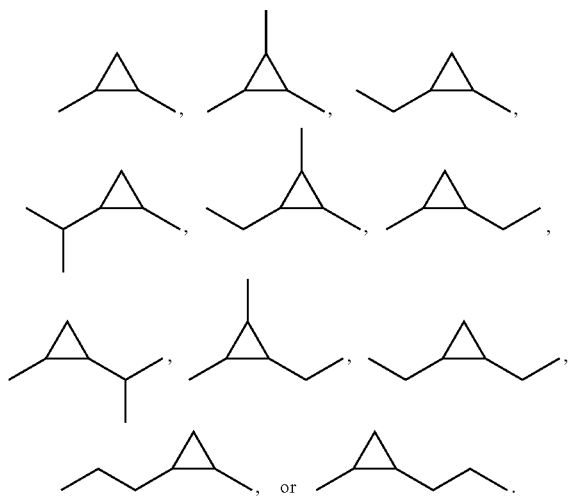

More particularly, 1, 2, or 3 of the hydrogen atoms in the $C_{1-6}$alkylene is further substituted by halogen. Particularly, the halogen is F.

Particularly, the present invention features a compound of Formula (I) wherein $R_4$ or $R_5$ is

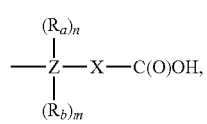

wherein X is optionally substituted —O—$C_{1-5}$alkyl- or optionally substituted $C_{1-6}$alkylene. More particularly, the $C_{1-6}$alkylene is unsaturated. More particularly, the $C_{1-6}$alkylene contains a double or triple bond.

Particularly, the present invention features a compound of Formula (I) wherein m and n are both 0.

Particularly, the present invention features a compound of Formula (I) wherein $R_a$ and $R_b$ are independently selected from —OCF$_3$, —OCH$_3$, —OCH$_2$CF$_3$, and —CH=CH—C(O)OH.

Particularly, the present invention features a compound of Formula (I) wherein
$R_1$ is H, —CH$_3$, —CH$_2$CH$_3$, —CH$_2$CH$_2$CH$_3$, —CH$_2$CF$_3$, or —CH(CH$_3$)$_2$;
$R_2$ and $R_3$ are —CH$_3$;
$R_4$ is

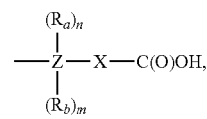

wherein
Z is selected from

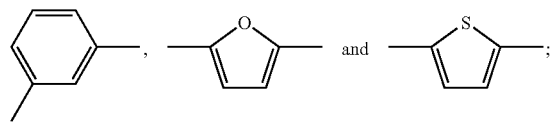

X is selected from a bond, —CH$_2$—,

—CH$_2$CH$_2$—, CH=CH—, —C≡C—, —CH$_2$CH$_2$CH$_2$—, —CH(CH$_3$)CH$_2$—, —CH$_2$CH(CH$_3$)—, —C(CH$_3$)=CH$_2$—, —CH=C(CH$_3$)—, —O—CH$_2$—, —O—C(CH$_3$)$_2$—, —CH=C(F)—, —CH=CH—C(CH$_3$)=CH—, and —CH=CH—CH=CH—;
$R_a$ and $R_b$ are independently selected from —OCF$_3$, —OCH$_3$, —OCH$_2$CF$_3$, and —CH=CH—C(O)OH;
m is 0 or 1; and
n is 0, 1 or 2;
or alternatively $R_4$ is H or CH$_3$;
with the proviso that when $R_4$ is

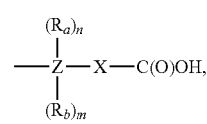

then $R_5$ cannot be

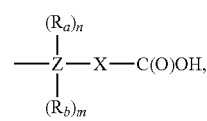

provided further that when $R_4$ is H or CH$_3$, then $R_5$ cannot be H or optionally substituted $C_{1-3}$alkyl;
$R_5$ is

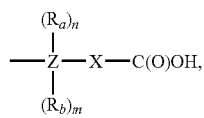

wherein
Z is selected from

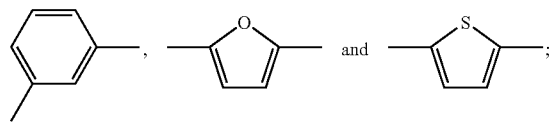

X is selected from a bond, —CH₂—,

—CH₂CH₂—, —CH=CH—, —C≡C—, —CH₂CH₂CH₂—, —CH(CH₃)CH₂—, —CH₂CH(CH₃)—, —C(CH₃)=CH₂—, —CH=C(CH₃)—, —O—CH₂—, —O—C(CH₃)₂—, —CH=C(F)—, —CH=CH—C(CH₃)=CH—, and —CH=CH—CH=CH—; and $R_a$ and $R_b$ are independently selected from —OCF₃, —OCH₃, —OCH₂CF₃, and —CH=CH—C(O)OH;
m is 0 or 1; and
n is 0, 1 or 2;
or alternatively $R_5$ is H or CH₃;
with the proviso that when $R_5$ is

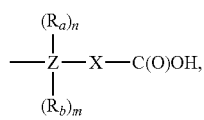

then $R_4$ cannot be

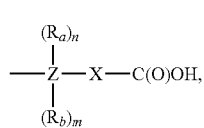

provided further that when $R_5$ is H or CH₃, then $R_4$ cannot be H or CH₃; and
$R_6$ is H or CH₃.

Another aspect of the present invention features a pharmaceutical composition comprising at least one compound of Formula (I) and at least one pharmaceutically acceptable carrier. In another aspect of the invention, the pharmaceutical composition further comprises at least one additional agent, drug, medicament, antibody and/or inhibitor for treating, ameliorating and/or preventing a RXR mediated disease. In one embodiment, at least one compound of Formula (I) is selected from

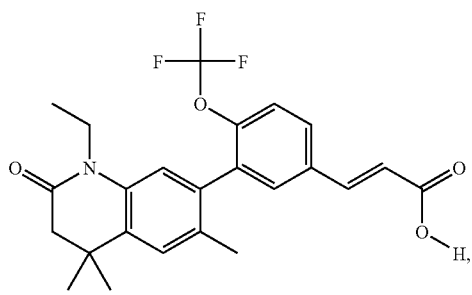

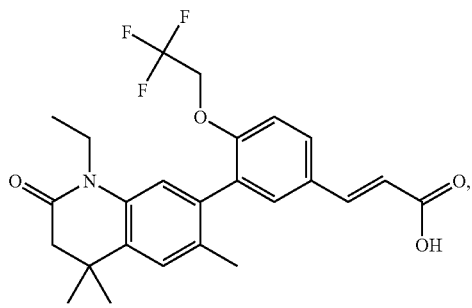

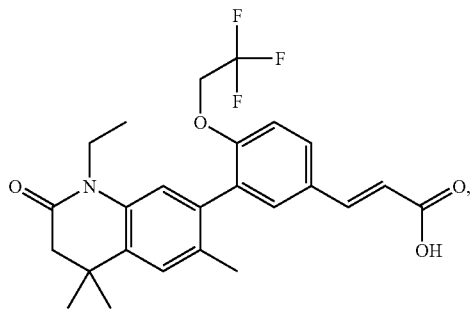

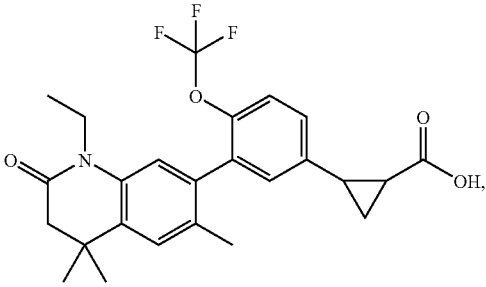

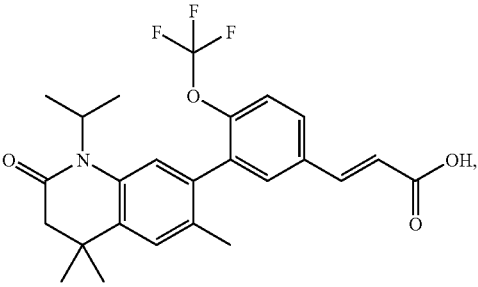

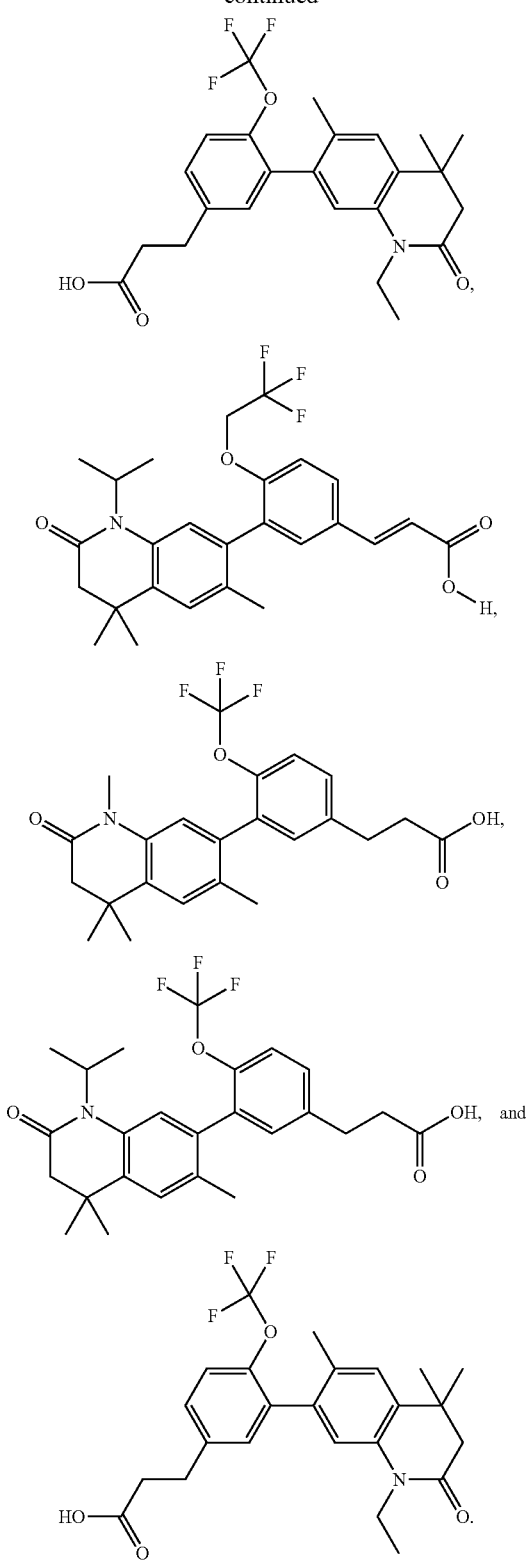
In another embodiment, at least one compound of Formula (I) is selected from -continued

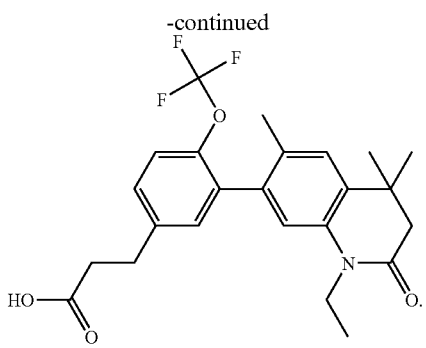

In another embodiment of the invention a method is disclosed for treating, preventing or ameliorating a RXR mediated condition in a subject in need thereof comprising administering to the subject a therapeutically effective amount of at least one compound of Formula (I). An embodiment of the invention includes a method for treating, preventing or ameliorating a RXR mediated condition selected from cancer, diabetes, dyslipidemia, hypercholesterolemia, and associated symptoms or complications thereof in a subject in need thereof, comprising administering to said subject a therapeutically effective amount of at least one compound of Formula (I).

A further embodiment of the invention is a method for treating, preventing or ameliorating a RXR mediated condition selected from IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts in a subject in need thereof, comprising administering to said subject a therapeutically effective amount of at least one compound of Formula (I).

One embodiment of the invention is a method of treating hypertriglyceridemia, raising levels of HDL, lowering levels of LDL, and/or lowering total cholesterol.

Furthermore, RXR agonists can be co-administered with a second agent other than a retinoid receptor agonist; such second agent can be, for example, an anti-diabetic agent, a lipid lowering agent, a blood pressure lowering agent, and an anti-thrombotic agent (e.g., aspirin, heparins, glycoprotein IIb-IIIa inhibitors, or Factor Xa inhibitors).

Particularly, it is an embodiment of the invention to provide a method for treating, preventing or ameliorating a condition selected from cancer, diabetes, dyslipidemia, hypercholesterolemia, and associated symptoms or complications thereof in a subject in need thereof, comprising administering to said subject a thereapeuctically effective amount of (a) at least one compound of Formula (I); and (b) at least one additional agent selected from a retinoid receptor agonist, an anti-diabetic agent, a lipid lowering agent, an anti-thrombotic agent, and a blood pressure lowering agent, said administration being in any order. In one embodiment, the additional agent is a second RXR agonist. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent. In another embodiment, the additional agent is a RAR agonist.

Another embodiment of the invention is a method for inhibiting the onset of a RXR condition in a subject in need thereof, comprising administering to said subject a therapeutically effective amount of at least one compound of Formula (I). Another embodiment of the invention is a method for inhibiting the onset of a condition selected from cancer, diabetes, dyslipidemia, hypercholesterolemia, and associated symptoms or complications thereof in a subject in need thereof, comprising administering to said subject a therapeutically effective amount of (a) at least one compound of Formula (I); and (b) at least one compound selected from the group consisting of a retinoid receptor agonist, an anti-diabetic agent, a lipid lowering agent, an anti-thrombotic agent, and a blood pressure lowering agent, said co-administration being in any order and the combined amounts providing the desired prophylactic effect.

A further embodiment of the invention is a method for inhibiting the onset of a RXR condition selected from IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts in a subject in need thereof, comprising administering to said subject a therapeutically effective amount of at least one compound of Formula (I). In one embodiment, the additional agent is a second RXR agonist. In a further embodiment, the additional agent is an anti-diabetic agent. In another embodiment, the additional agent is a lipid lowering agent. In still another embodiment, the additional agent is an anti-thrombotic agent. In yet another embodiment, the additional agent is a blood pressure lowering agent. In another embodiment, the additional agent is a RAR agonist.

It is a further embodiment of the invention to provide a process for making a pharmaceutical composition comprising admixing any of the compounds according to Formula (I) and a pharmaceutically acceptable carrier.

In a further embodiment of the invention, a method for treating, preventing or ameliorating a RXR mediated condition in a subject in need thereof comprising administering to the subject a therapeutically effective amount of at least one compound of Formula (I), wherein the therapeutically effective amount of the compound of Formula (I) is from about 0.001 mg/kg/day to about 5 mg/kg/day.

In a further embodiment of the invention, a method for inhibiting the onset of a RXR mediated condition in a subject in need thereof comprising administering to the subject a therapeutically effective amount of at least one compound of Formula (I), wherein the therapeutically effective amount of the compound of Formula (I) is from about 0.001 mg/kg/day to about 5 mg/kg/day.

The invention is further described below.

A) Terms

Some terms are defined below and by their usage throughout this disclosure.

Unless otherwise noted, "alkyl" as used herein, whether used alone or as part of a substituent group, includes straight, cyclic, and branched-chain alkyl having 1 to 6 carbon atoms, or any number within this range. For example, alkyl radicals include methyl, ethyl, n-propyl, isopropyl, n-butyl, isobutyl, sec-butyl, t-butyl, 2-butenyl, 2-butynyl, n-pentyl, 3-(2-methyl)butyl, 2-pentyl, 2-methylbutyl, neopentyl, n-hexyl, 2-hexyl and 2-methylpentyl. "Alkoxy" radicals are oxygen ethers formed from the previously described straight, branched, or cyclic chain alkyl groups.

The term "alkenyl" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, beta-1,3-dien-2-yl, cyclobut-1-en-1-yl, cyclobut-1-en-3-yl, cyclobuta-1,3-dien-1-yl, etc.; and the like.

The term "alkynyl" refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

The term "alkylene" denotes straight, branched, or cyclic alkyl, or straight or branched alkenyl, or straight or branched alkynyl, optionally substituted with one to five, preferably one to three groups including, but not limited to, optionally substituted $C_{1-3}$alkyl and F.

The term "oxo" whether used alone or as part of a substituent group refers to an O= to either a carbon or a sulfur atom. For example, phthalimide and saccharin are examples of compounds with oxo substituents.

The term "substituted" refers to a radical in which one or more hydrogen atoms are each independently replaced with the same or different substituent(s). Preferred substituents include hydroxy, halogen, oxo, amino, carboxyl, and alkoxy.

With reference to substituents, the term "independently" means that when more than one of such substituent is possible, such substituents may be the same or different from each other.

The term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who is the object of treatment, observation or experiment.

The term "RXR" as used herein refers to Retinoid-X Receptors.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Diabetes and associated symptoms or complications include such conditions as IDDM, NIDDM, Syndrome X, IGT (Impaired Glucose Tolerance), IFG (Impaired Fasting Glucose), obesity, nephropathy, neuropathy, retinopathy, atherosclerosis, polycystic ovary syndrome, polycystic ovarian syndrome, hypertension, ischemia, stroke, heart disease, irritable bowel disorder, inflammation, and cataracts. IGT and IFG are also known as "prediabetic state."

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present invention provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the invention; or (c) both (or more) drugs are administered in an amount that is sub-therapeutic or sub-prophylactic if administered alone, but are therapeutic or prophylactic when administered together.

The term "protecting groups" refer to those moieties known in the art that are used to mask functional groups; protecting groups may be removed during subsequent synthetic transformations or by metabolic or other in vivo administration conditions. During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known in the art. Examples of hydroxyl and diol protecting groups are provided below.

Protection for the hydroxyl group includes methyl ethers, substituted methyl ethers, substituted ethyl ethers, substituted benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, and polyethyleneglycol ethers.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-ylmethyl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate), and polyethyleneglycol esters.

Carbonates

Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, methyl dithiocarbonate, and polyethyleneglycol carbonates.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthlomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate(tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate Sulfonates Examples of sulfonates include sulfate, methanesulfonate (mesylate), benzylsulfonate, and tosylate.

Protection for 1,2- and 1,3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, 30% cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyldisiloxanylidene) derivative.

B) Compounds

| STRUCTURE | COMPOUND # | NAME |
|---|---|---|
| 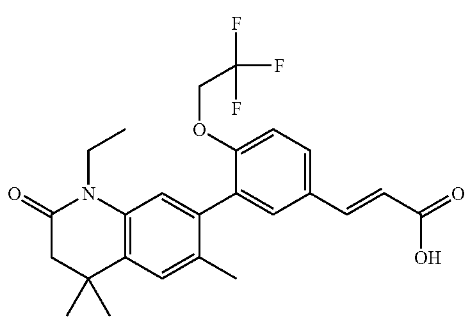 | 1 | 3-[3-(1-Ethyl-4,4,6-trimethyl-2-oxo-1,2,3,4-tetrahydro-quinolin-7-yl)-4-(2,2,2-trifluoro-ethoxy)-phenyl]-acrylic acid |

-continued

| STRUCTURE | COMPOUND # | NAME |
|---|---|---|
| 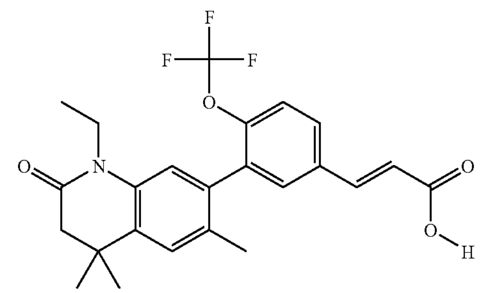 | 2 | 3-[3-(1-Ethyl-4,4,6-trimethyl-2-oxo-1,2,3,4-tetrahydro-quinolin-7-yl)-4-trifluoromethoxy-phenyl]-acrylic acid |
| 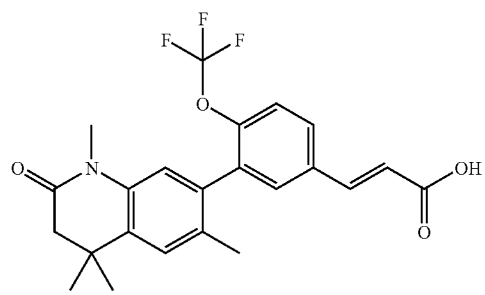 | 3 | 3-[3-(1,4,4,6-Tetramethyl-2-oxo-1,2,3,4-tetrahydro-quinolin-7-yl)-4-trifluoromethoxy-phenyl]-acrylic acid |
| 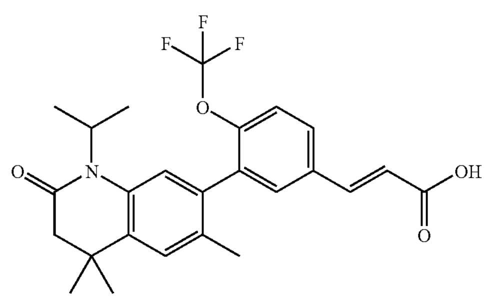 | 4 | 3-[3-(1-Isopropyl-4,4,6-trimethyl-2-oxo-1,2,3,4-tetrahydro-quinolin-7-yl)-4-trifluoromethoxy-phenyl]-acrylic acid |
| 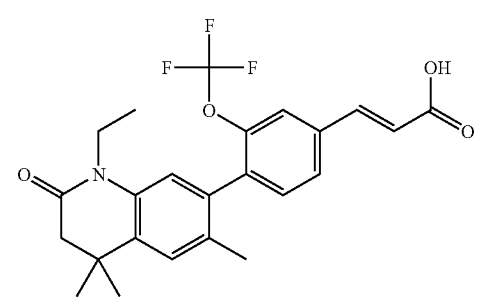 | 5 | 3-[4-(1-Ethyl-4,4,6-trimethyl-2-oxo-1,2,3,4-tetrahydro-quinolin-7-yl)-3-trifluoromethoxy-phenyl]-acrylic acid |
| 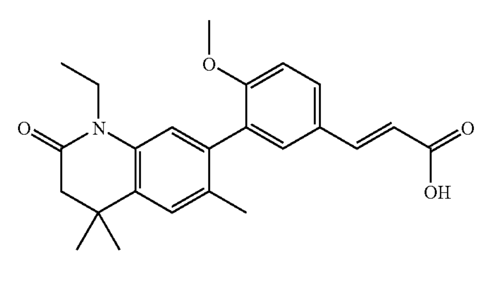 | 6 | 3-[3-(1-Ethyl-4,4,6-trimethyl-2-oxo-1,2,3,4-tetrahydro-quinolin-7-yl)-4-methoxy-phenyl]-acrylic acid |

| STRUCTURE | COMPOUND # | NAME |
|---|---|---|
| 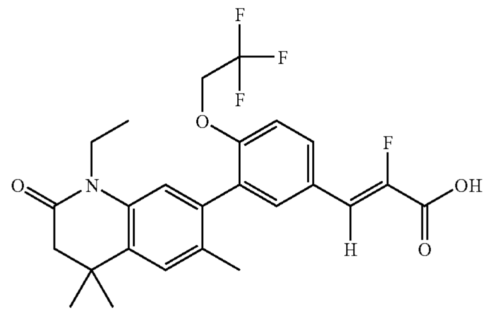 | 7 | 3-[3-(1-Ethyl-4,4,6-trimethyl-2-oxo-1,2,3,4-tetrahydro-quinolin-7-yl)-4-(2,2,2-trifluoro-ethoxy)-phenyl]-2-fluoro-acrylic acid |
| 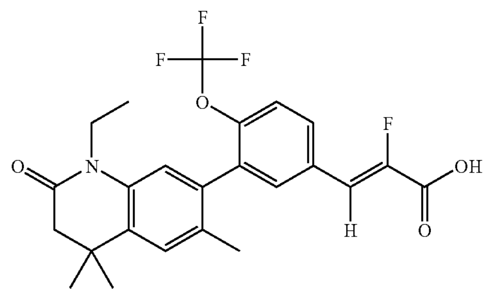 | 8 | 3-[3-(1-Ethyl-4,4,6-trimethyl-2-oxo-1,2,3,4-tetrahydro-quinolin-7-yl)-4-trifluoromethoxy-phenyl]-2-fluoro-acrylic acid |
| 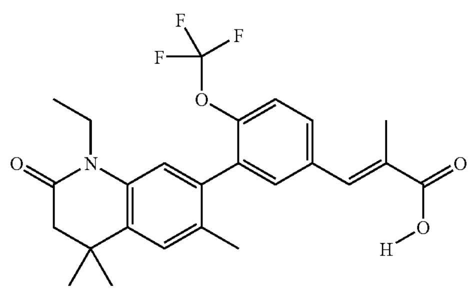 | 9 | 3-[3-(1-Ethyl-4,4,6-trimethyl-2-oxo-1,2,3,4-tetrahydro-quinolin-7-yl)-4-trifluoromethoxy-phenyl]2-methyl-acrylic acid |
| 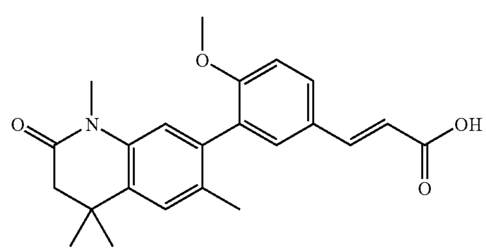 | 10 | 3-[4-Methoxy-3-(1,4,4,6-tetramethyl-2-oxo-1,2,3,4-tetrahydro-quinolin-7-yl)-phenyl]-acrylic acid |
| 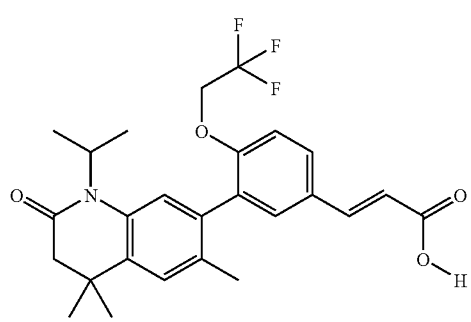 | 11 | 3-[3-(1-Isopropyl-4,4,6-trimethyl-2-oxo-1,2,3,4-tetrahydro-quinolin-7-yl)-4-(2,2,2-trifluoro-ethoxy)-phenyl]-acrylic acid |

| STRUCTURE | COMPOUND # | NAME |
|---|---|---|
| 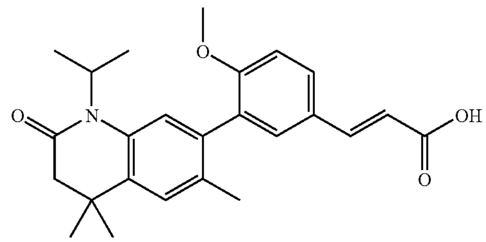 | 12 | 3-[3-(1-Isopropyl-4,4,6-trimethyl-2-oxo-1,2,3,4-tetrahydro-quinolin-7-yl)-4-methoxy-phenyl]-acrylic acid |
| 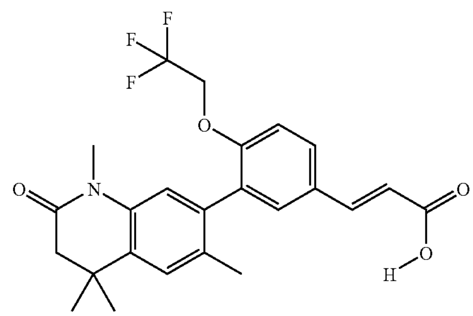 | 13 | 3-[3-(1,4,4,6-Tetramethyl-2-oxo-1,2,3,4-tetrahydro-quinolin-7-yl)-4-(2,2,2-trifluoro-ethoxy)-phenyl]-acrylic acid |
| 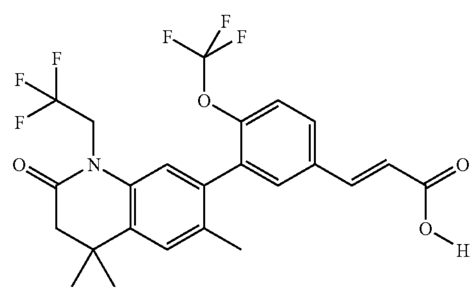 | 14 | 3-{4-Trifluoromethoxy-3-[4,4,6-trimethyl-2-oxo-1-(2,2,2-trifluoro-ethyl)-1,2,3,4-tetrahydro-quinolin-7-yl]-phenyl}-acrylic acid |
| 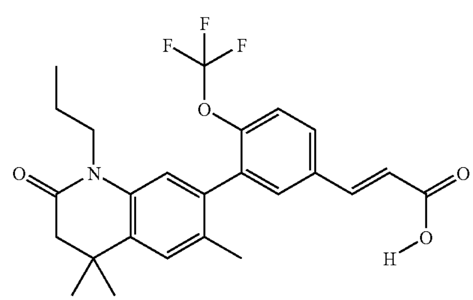 | 15 | 3-[4-Trifluoromethoxy-3-(4,4,6-trimethyl-2-oxo-1-propyl-1,2,3,4-tetrahydro-quinolin-7-yl)-phenyl]-acrylic acid |
| 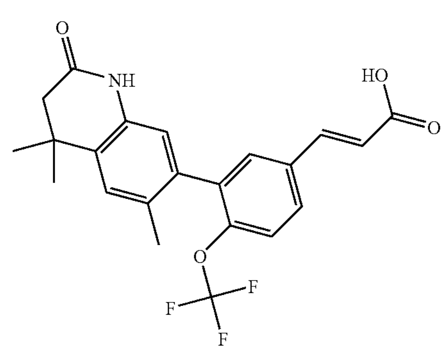 | 16 | 3-[4-Trifluoromethoxy-3-(4,4,6-trimethyl-2-oxo-1,2,3,4-tetrahydro-quinolin-7-yl)-phenyl]-acrylic acid |

-continued

| STRUCTURE | COMPOUND # | NAME |
|---|---|---|
| 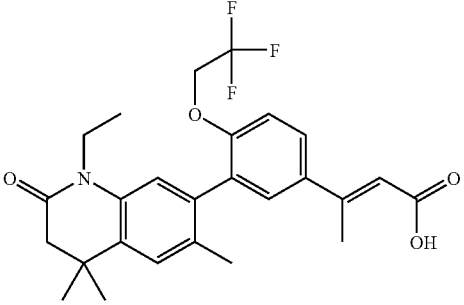 | 17 | 3-[3-(1-Ethyl-4,4,6-trimethyl-2-oxo-1,2,3,4-tetrahydro-quinolin-7-yl)-4-(2,2,2-trifluoro-ethoxy)-phenyl]-but-2-enoic acid |
| 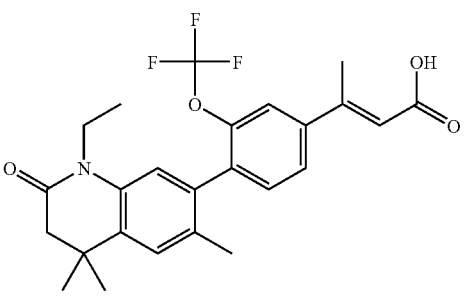 | 18 | 3-[4-(1-Ethyl-4,4,6-trimethyl-2-oxo-1,2,3,4-tetrahydro-quinolin-7-yl)-3-trifluoromethoxy-phenyl]-2-methyl-acrylic acid |
| 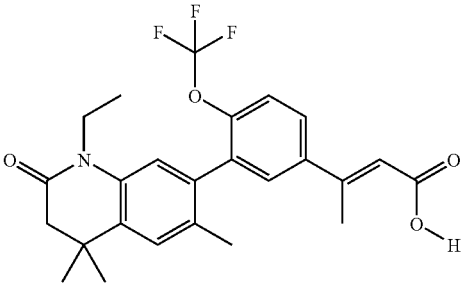 | 19 | 3-[3-(1-Ethyl-4,4,6-trimethyl-2-oxo-1,2,3,4-tetrahydro-quinolin-7-yl)-4-trifluoromethoxy-phenyl]-but-2-enoic acid |
| 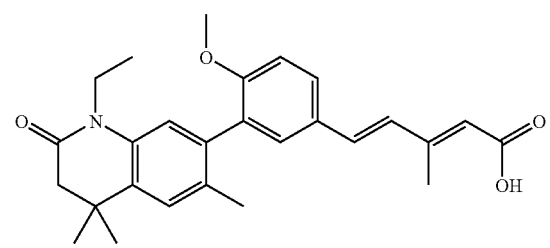 | 20 | 5-[3-(1-Ethyl-4,4,6-trimethyl-2-oxo-1,2,3,4-tetrahydro-quinolin-7-yl)-4-methoxy-phenyl]-3-methyl-penta-2,4-dienoic acid |
| 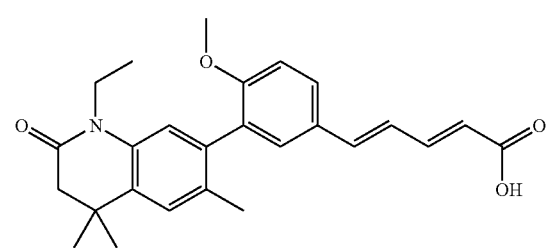 | 21 | 5-[3-(1-Ethyl-4,4,6-trimethyl-2-oxo-1,2,3,4-tetrahydro-quinolin-7-yl)-4-methoxy-phenyl]-penta-2,4-dienoic acid |

-continued

| STRUCTURE | COMPOUND # | NAME |
|---|---|---|
| 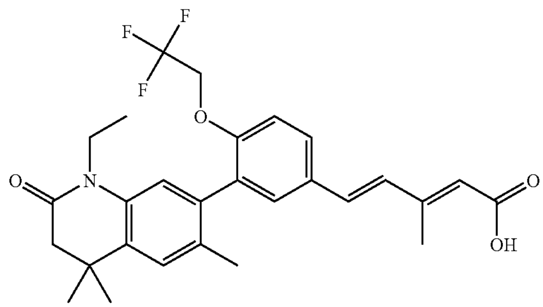 | 22 | 5-[3-(1-Ethyl-4,4,6-trimethyl-2-oxo-1,2,3,4-tetrahydro-quinolin-7-yl)-4-(2,2,2-trifluoro-ethoxy)-phenyl]-3-methyl-penta-2,4-dienoic acid |
| 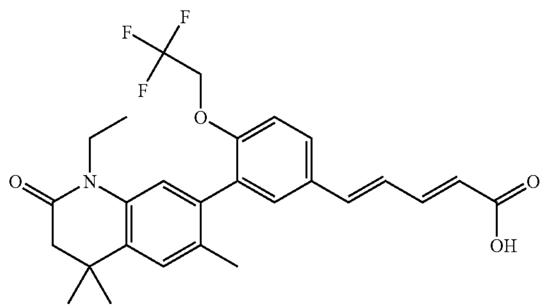 | 23 | 5-[3-(1-Ethyl-4,4,6-trimethyl-2-oxo-1,2,3,4-tetrahydro-quinolin-7-yl)-4-(2,2,2-trifluoro-ethoxy)-phenyl]-penta-2,4-dienoic acid |
| 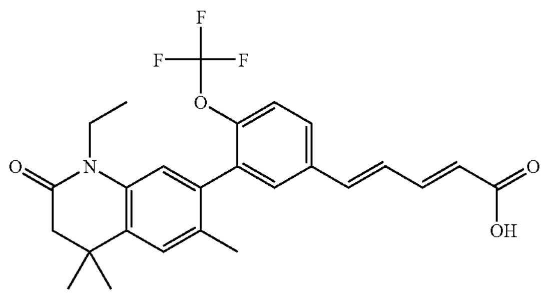 | 24 | 5-[3-(1-Ethyl-4,4,6-trimethyl-2-oxo-1,2,3,4-tetrahydro-quinolin-7-yl)-4-trifluoromethoxy-phenyl]-penta-2,4-dienoic acid |
| 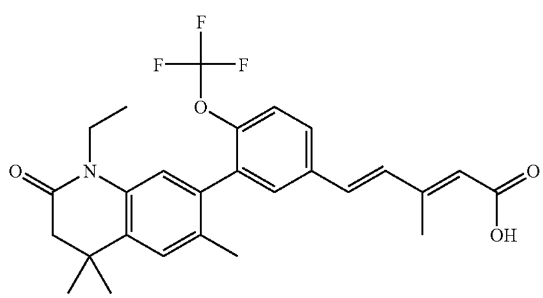 | 25 | 5-[3-(1-Ethyl-4,4,6-trimethyl-2-oxo-1,2,3,4-tetrahydro-quinolin-7-yl)-4-trifluoromethoxy-phenyl]-3-methyl-penta-2,4-dienoic acid |
| 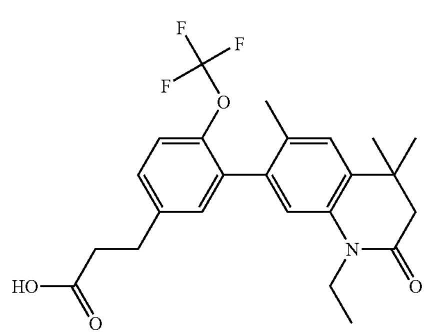 | 26 | 3-[3-(1-Ethyl-4,4,6-trimethyl-2-oxo-1,2,3,4-tetrahydro-quinolin-7-yl)-4-trifluoromethoxy-phenyl]-propionic acid |

| STRUCTURE | COMPOUND # | NAME |
|---|---|---|
| 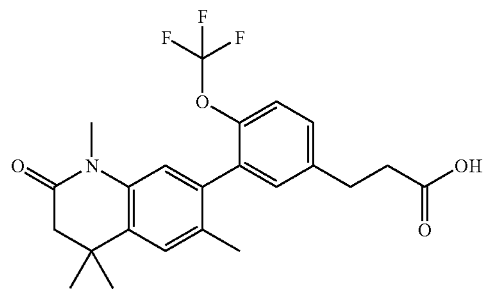 | 27 | 3-[3-(1,4,4,6-Tetramethyl-2-oxo-1,2,3,4-tetrahydro-quinolin-7-yl)-4-trifluoromethoxy-phenyl]-propionic acid |
| 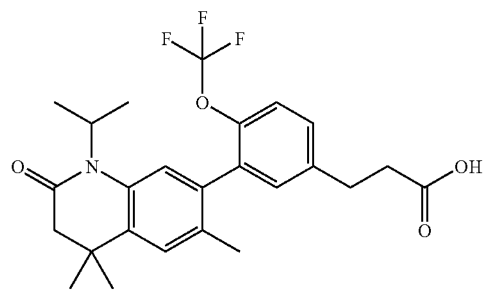 | 28 | 3-[3-(1-Isopropyl-4,4,6-trimethyl-2-oxo-1,2,3,4-tetrahydro-quinolin-7-yl)-4-trifluoromethoxy-phenyl]-propionic acid |
| 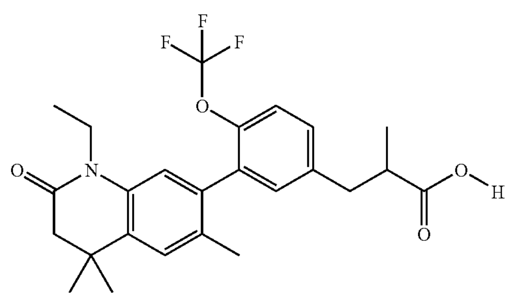 | 29 | 3-[3-(1-Ethyl-4,4,6-trimethyl-2-oxo-1,2,3,4-tetrahydro-quinolin-7-yl)-4-trifluoromethoxy-phenyl]-2-methyl-propionic acid |
| 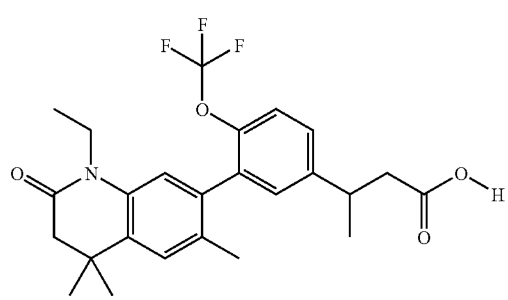 | 30 | 3-[3-(1-Ethyl-4,4,6-trimethyl-2-oxo-1,2,3,4-tetrahydro-quinolin-7-yl)-4-trifluoromethoxy-phenyl]3-butyric acid |
| 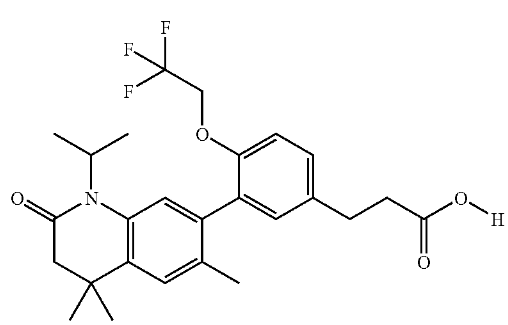 | 31 | 3-[3-(1-Isopropyl-4,4,6-trimethyl-2-oxo-1,2,3,4-tetrahydro-quinolin-7-yl)-4-(2,2,2-trifluoro-ethoxy)-phenyl]-propionic acid |

-continued

| STRUCTURE | COMPOUND # | NAME |
|---|---|---|
| 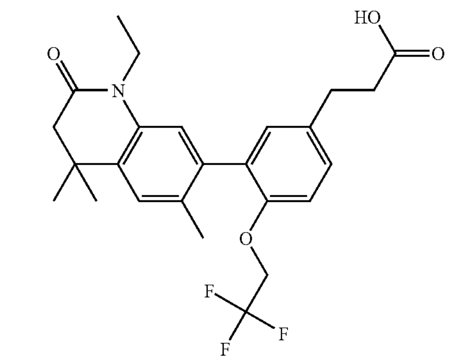 | 32 | 3-[3-(1-Ethyl-4,4,6-trimethyl-2-oxo-1,2,3,4-tetrahydro-quinolin-7-yl)-4-(2,2,2-trifluoro-ethoxy)-phenyl]-propionic acid |
| 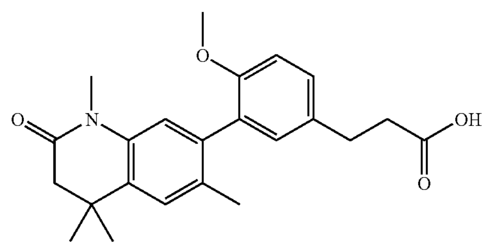 | 33 | 3-[4-Methoxy-3-(1,4,4,6-tetramethyl-2-oxo-1,2,3,4-tetrahydro-quinolin-7-yl)-phenyl]-propionic acid |
| 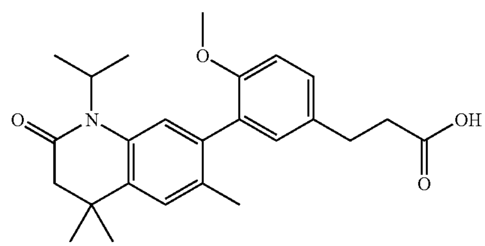 | 34 | 3-[3-(1-Isopropyl-4,4,6-trimethyl-2-oxo-1,2,3,4-tetrahydro-quinolin-7-yl)-4-methoxy-phenyl]-propionic acid |
| 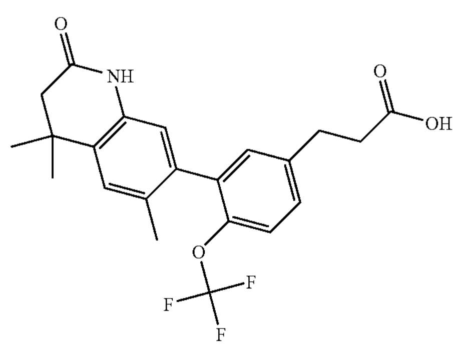 | 35 | 3-[4-Trifluoromethoxy-3-(4,4,6-trimethyl-2-oxo-1,2,3,4-tetrahydro-quinolin-7-yl)-phenyl]-propionic acid |
| 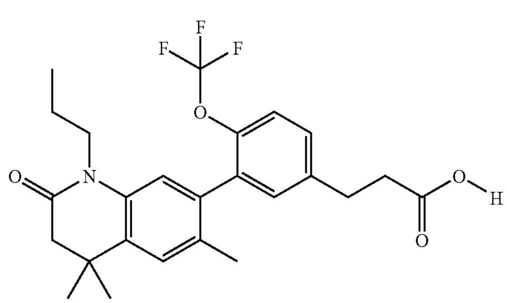 | 36 | 3-[4-Trifluoromethoxy-3-(4,4,6-trimethyl-2-oxo-1-propyl-1,2,3,4-tetrahydro-quinolin-7-yl)-phenyl]-propionic acid |

-continued

| STRUCTURE | COMPOUND # | NAME |
|---|---|---|
| 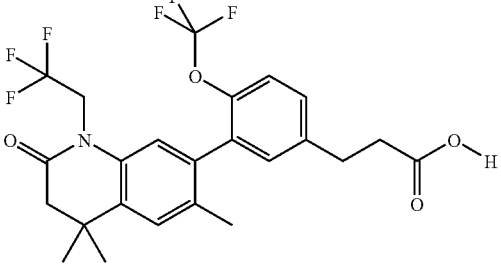 | 37 | 3-{4-Trifluoromethoxy-3-[4,4,6-trimethyl-2-oxo-1-(2,2,2-trifluoro-ethyl)-1,2,3,4-tetrahydro-quinolin-7-yl]-phenyl}-propionic acid |
| 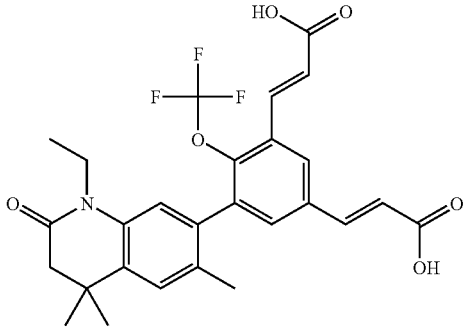 | 38 | 3-[3-(2-Carboxy-vinyl)-5-(1-ethyl-4,4,6-trimethyl-2-oxo-1 2,3,4-tetrahydro-quinolin-7-yl)-4-trifluoromethoxy-phenyl]-acrylic acid |
| 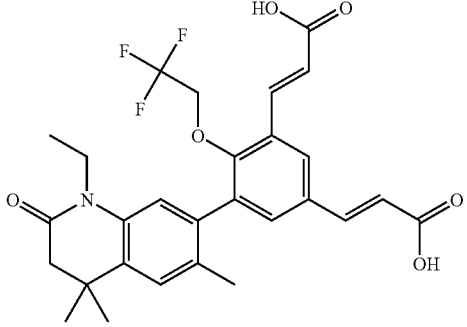 | 39 | 3-[3-(2-Carboxy-vinyl)-5-(1-ethyl-4,4,6-trimethyl-2-oxo-1,2,3,4-tetrahydro-quinolin-7-yl)-4-(2,2,2-trifluoro-ethoxy)-phenyl]-acrylic acid |
| 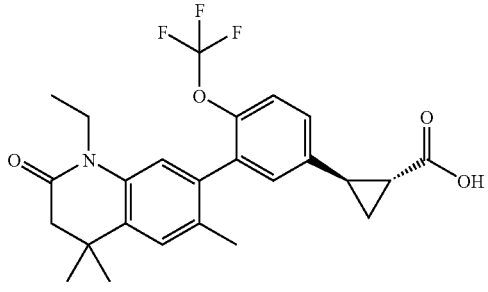 | 40 | (☐)-2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid |
| 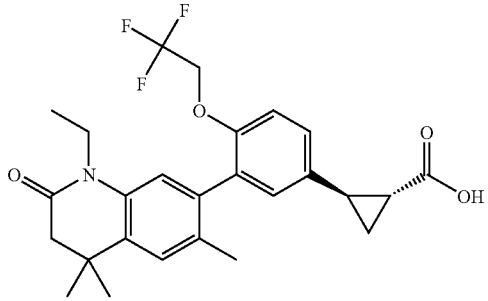 | 41 | (☐)-2-[3-(1-Ethyl-4,4,6-trimethyl-2-oxo-1,2,3,4-tetrahydro-quinolin-7-yl)-4-(2,2,2-trifluoro-ethoxy)-phenyl]-cyclopropanecarboxylic acid |

| STRUCTURE | COMPOUND # | NAME |
|---|---|---|
| 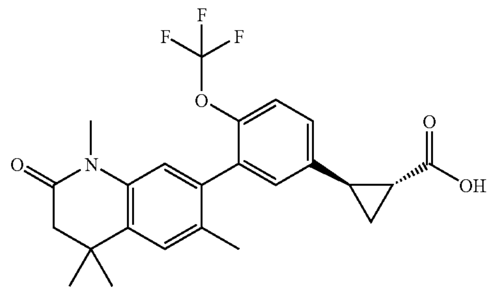 | 42 | (□)-2-[3-(1,4,4,6-Tetramethyl-2-oxo-1,2,3,4-tetrahydro-quinolin-7-yl)-4-trifluoromethoxy-phenyl]-cyclopropanecarboxylic acid |
| 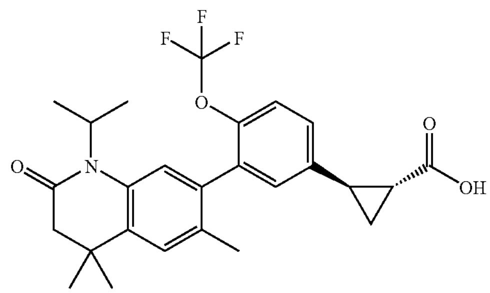 | 43 | (□)-2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid |
| 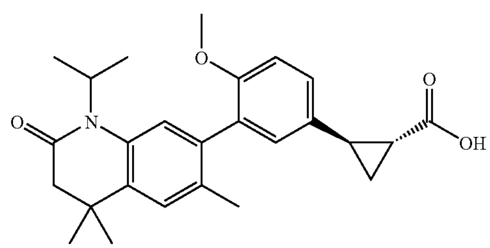 | 44 | (□)-2-[3-(1-Isopropyl-4,4,6-trimethyl-2-oxo-1,2,3,4-tetrahydro-quinolin-7-yl)-4-methoxy-phenyl]-cyclopropanecarboxylic acid |
| 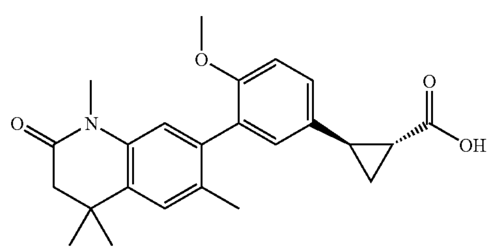 | 45 | (□)-2-[4-Methoxy-3-(1,4,4,6-tetramethyl-2-oxo-1,2,3,4-tetrahydro-quinolin-7-yl)-phenyl]-cyclopropanecarboxylic acid |
| 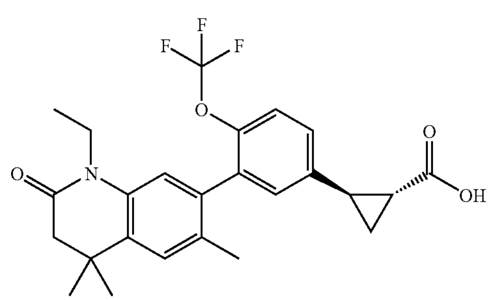 | 46 | ⁻-2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid |

-continued

| STRUCTURE | COMPOUND # | NAME |
|---|---|---|
| 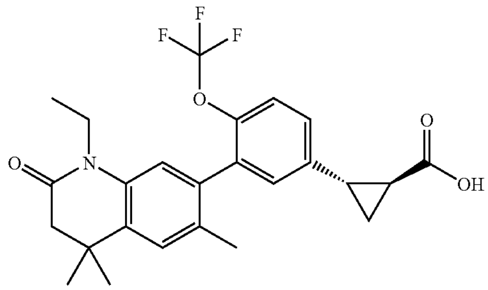 | 47 | ..-2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid |
| 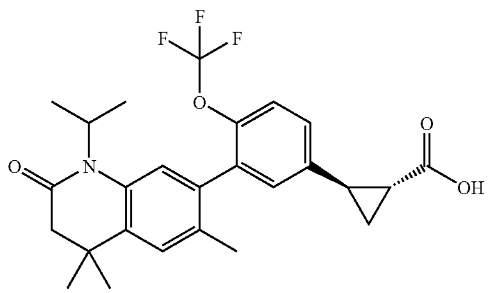 | 48 | ..-2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid |
| 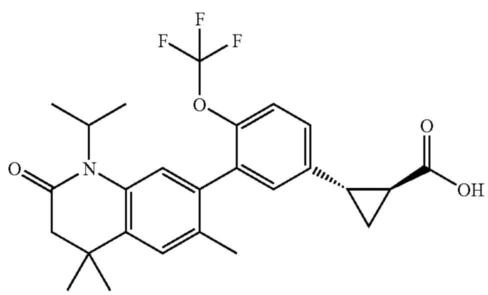 | 49 | ::-2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid |
| 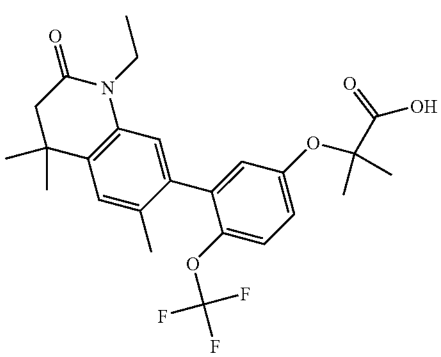 | 50 | 2-[3-(1-Ethyl-4,4,6-trimethyl-2-oxo-1,2,3,4-tetrahydro-quinolin-7-yl)-4-trifluoromethoxy-phenoxy]-2-methyl-propionic acid |
| 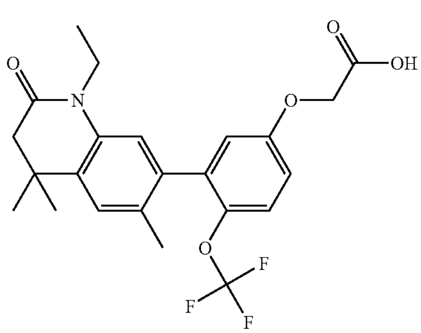 | 51 | [3-(1-Ethyl-4,4,6-trimethyl-2-oxo-1,2,3,4-tetrahydro-quinolin-7-yl)-4-trifluoromethoxy-phenoxy]-acetic acid |

-continued

| STRUCTURE | COMPOUND # | NAME |
|---|---|---|
| 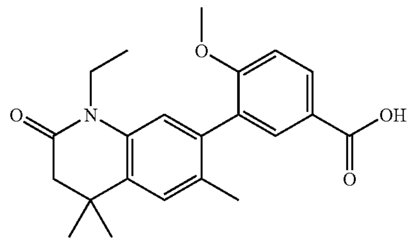 | 52 | 3-(1-Ethyl-4,4,6-trimethyl-2-oxo-1,2,3,4-tetrahydro-quinolin-7-yl)-4-methoxy-benzoic acid |
| 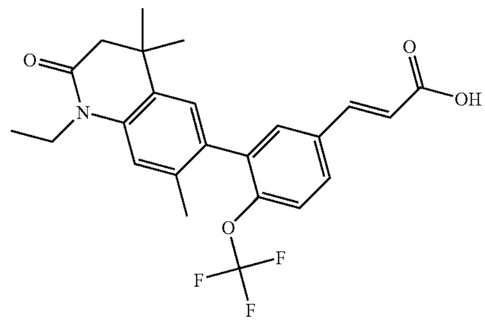 | 53 | 3-[3-(1-Ethyl-4,4,7-trimethyl-2-oxo-1,2,3,4-tetrahydro-quinolin-6-yl)-4-trifluoromethoxy-phenyl]-acrylic acid |
| 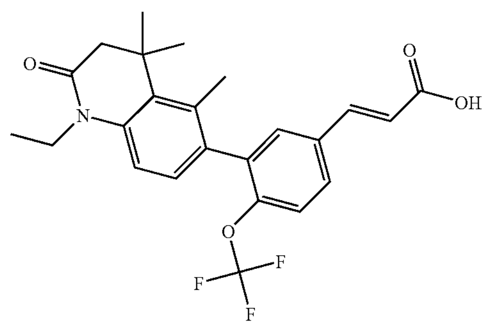 | 54 | 3-[3-(1-Ethyl-4,4,5-trimethyl-2-oxo-1,2,3,4-tetrahydro-quinolin-6-yl)-4-trifluoromethoxy-phenyl]-acrylic acid |
| 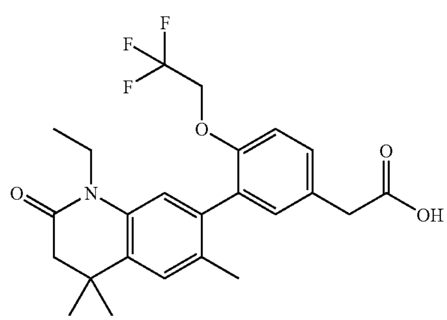 | 55 | [3-(1-Ethyl-4,4,6-trimethyl-2-oxo-1,2,3,4-tetrahydro-quinolin-7-yl)-4-(2,2,2-trifluoro-ethoxy)-phenyl]-acetic acid |
| 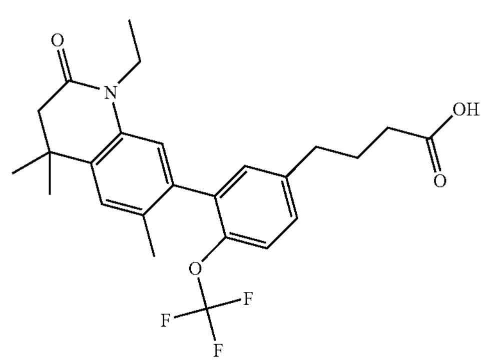 | 56 | 4-[3-(1-Ethyl-4,4,6-trimethyl-2-oxo-1,2,3,4-tetrahydro-quinolin-7-yl)-4-trifluoromethoxy-phenyl]-butyric acid |

| STRUCTURE | COMPOUND # | NAME |
|---|---|---|
| 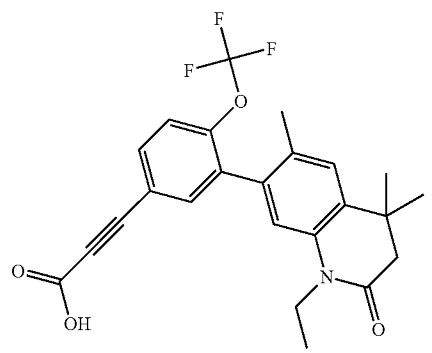 | 57 | [3-(1-Ethyl-4,4,6-trimethyl-2-oxo-1,2,3,4-tetrahydro-quinolin-7-yl)-4-trifluoromethoxy-phenyl]-propynoic acid |
| 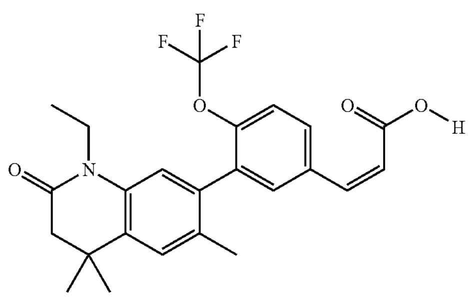 | 58 | 3-[3-(1-Ethyl-4,4,6-trimethyl-2-oxo-1,2,3,4-tetrahydro-quinolin-7-yl)-4-trifluoromethoxy-phenyl]-acrylic acid |
| 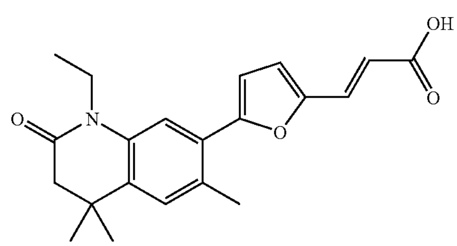 | 59 | 3-[5-(1-Ethyl-4,4,6-trimethyl-2-oxo-1,2,3,4-tetrahydro-quinolin-7-yl)-furan-2-yl]-acrylic acid |
| 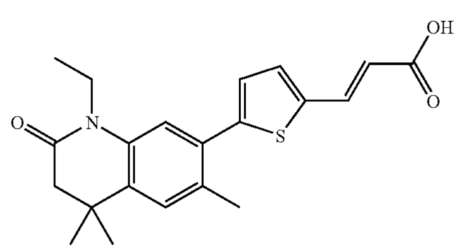 | 60 | 3-[5-(1-Ethyl-4,4,6-trimethyl-2-oxo-1,2,3,4-tetrahydro-quinolin-7-yl)-thiophen-2-yl]-acrylic acid |

C) Synthesis

The invention provides methods of making the disclosed compounds according to traditional organic synthetic methods as well as matrix or combinatorial synthetic methods. Schemes 1 through 12 describe suggested synthetic routes. Using these Schemes, the guidelines below, and the examples, a person of skill in the art may develop analogous or similar methods for a given compound that is within the invention. These methods are representative of the synthetic schemes, but are not to be construed as limiting the scope of the invention.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixtures of stereoisomers, these isomers may be separated by conventional techniques such as preparative chromatography. The compounds may be prepared in racemic form or as individual enantiomers or diasteromers by either stereospecific synthesis or by resolution.

The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers and enantiomers thereof are encompassed within the scope of the present invention.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Examples of the described synthetic routes include Examples 1 through 60 and Schemes 13-16. Compounds analogous to the target compounds of these examples can be made according to similar routes. The disclosed compounds are useful as pharmaceutical agents as described in the next section.

Abbreviations or acronyms useful herein include:

Boc (tent butyl carbamate)
BuLi (butyllithium)
DMAP (4-(dimethylamino)pyridine)
DMF (dimethylformamide)
DMPU (1,3-Dimethyl-3,4,5,6-tetrahydro-2(1H)-pyrimidinone)
DMSO (methyl sulfoxide)
EDCI (1-(3-Dimethylaminopropyl)-3-ethylcarbodiimide hydrochloride)
EtOAc (ethyl acetate)
LCMS (high pressure liquid chroatography with mass spectrometer)
LHMDS (lithium hexamethyl disilazide)
NaHMDS (sodium hexamethyl disilazide)
NaO$^t$Bu (sodium tert-butoxide)
NBS (N-Bromosuccinimide)
NMP (N-Methyl Pyrroidinone)
TEMPO (2,2,6,6-tetramethyl-1-piperidinyloxy, free radical)
TFA (trifluoroacetic acid);
SPE (solid phase extraction)
THF (tetrahydrofuran)
TLC (thin layer chromatography)

General Guidance

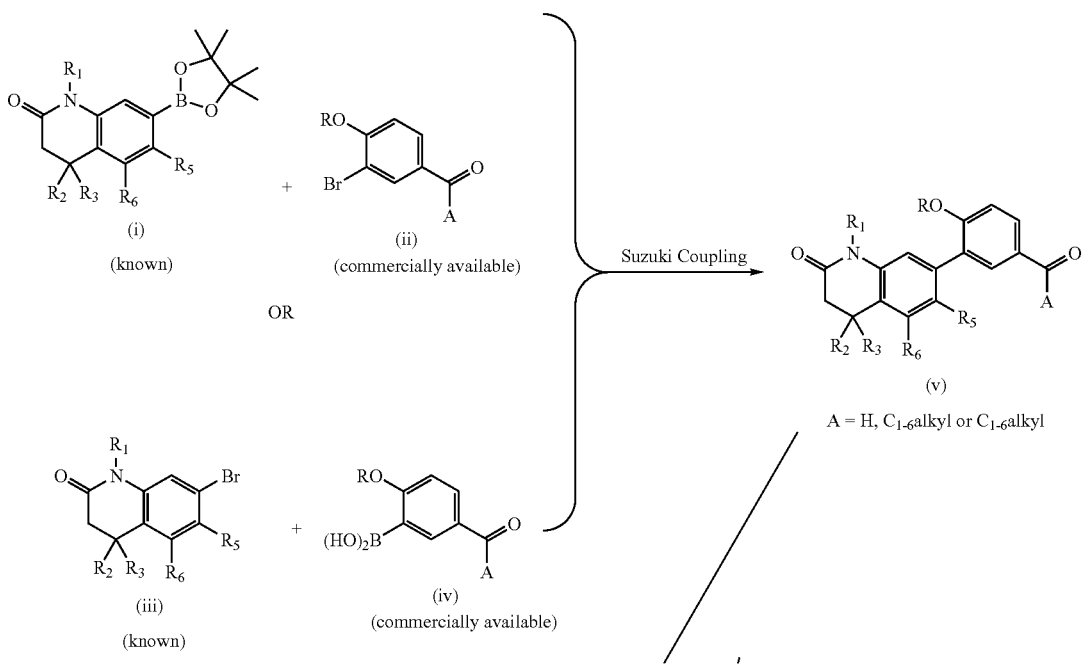

Scheme 1

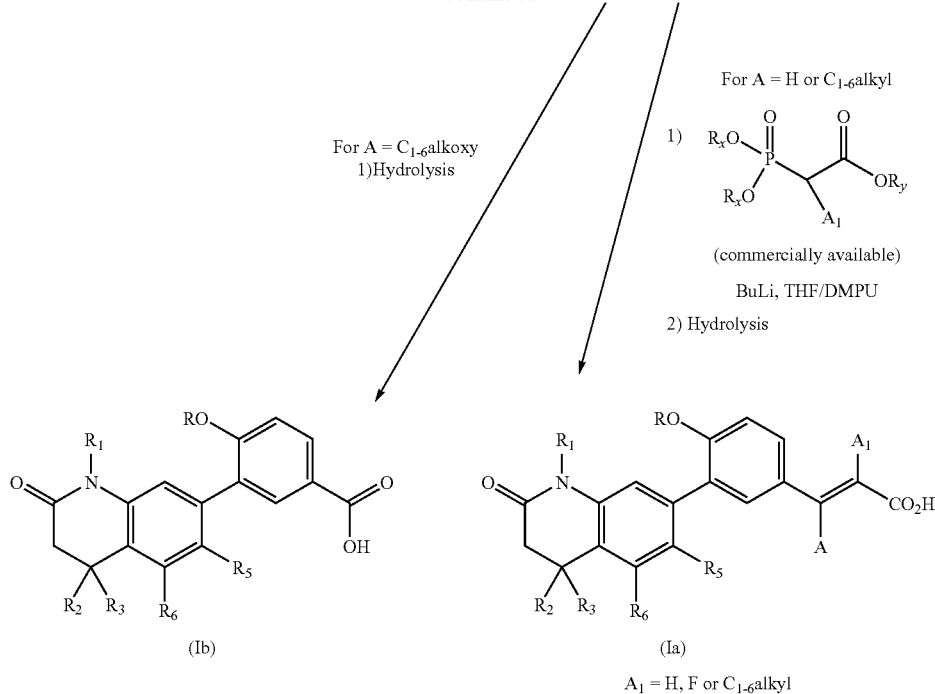

As demonstrated in Scheme 1, wherein A represents hydrogen (H), $C_{1-6}$alkyl, or $C_{1-6}$alkoxy, and $R_x$ and $R_y$ represent straight or branched $C_{1-4}$alkyl, and $A_1$ represents H, $C_{1-6}$alkyl, or halo, and $R_6$ represents H or optionally substituted $C_{1-3}$alkyl, and $R_x$ represents $C_{1-6}$alkyl, and $R_1$, $R_2$, $R_3$, and $R_6$ are as described hereinabove, a Suzuki reaction between suitable coupling partners such as an aryl boronic acid of (iv) or an aryl boronate ester (i) containing a carbonyl functionality and an aryl bromide (ii), leads to the compounds of (v). when A is hydrogen or alkyl, the compounds of (v) can be treated with an appropriate Wadsworth-Emmon's reagent (modified Witting reagent) to yield substituted phenylacrylic esters which can be hydrolyzed to corresponding substituted phenylacrylic acids (Ia) under acidic or basic conditions. Where A is alkoxy, the compounds of (v) can be hydrolyzed to synthesize the corresponding benzoic acid (Ib) as the desired product under known conditions.

Scheme 2

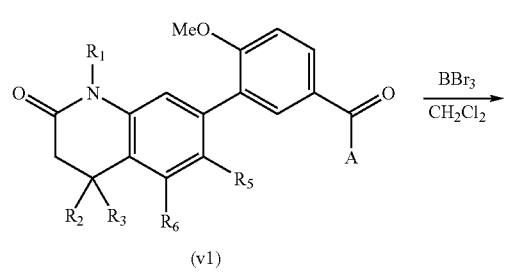

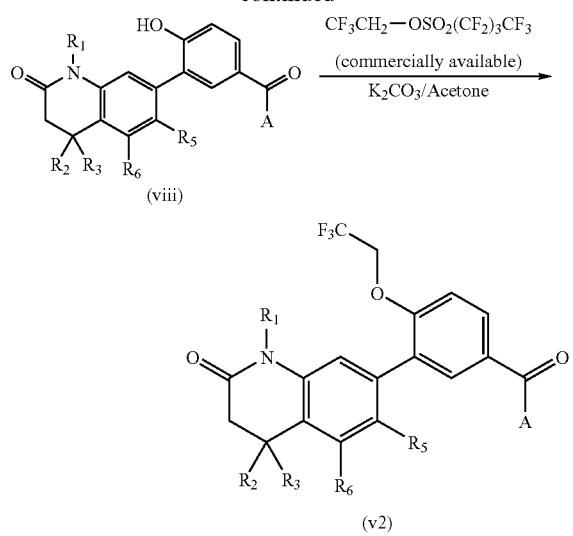

When a 2,2,2-trifluoroethoxy group is desired at the 4-position of the compounds of (Ia) and (Ib), a sequence similar to the one shown in Scheme 1 where R is $CH_3$ (Me) can be used to first make the compounds of (v1). The methoxy group can then be converted into a phenolic group in (viii) by treatment with boron tribromide as shown in Scheme 2. The compounds of (viii) can be reacted with 2,2,2-trifluoroethyl-nonafluoro-sulfonate in the presence of a base such as potassium carbonate to yield the desired product (v2), which can then be converted into the final compounds of the invention (Ia1, Ib1)

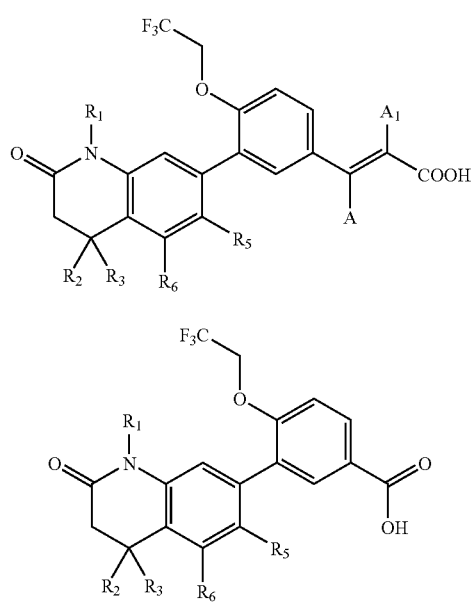

through the synthetic sequences shown in Scheme 1.

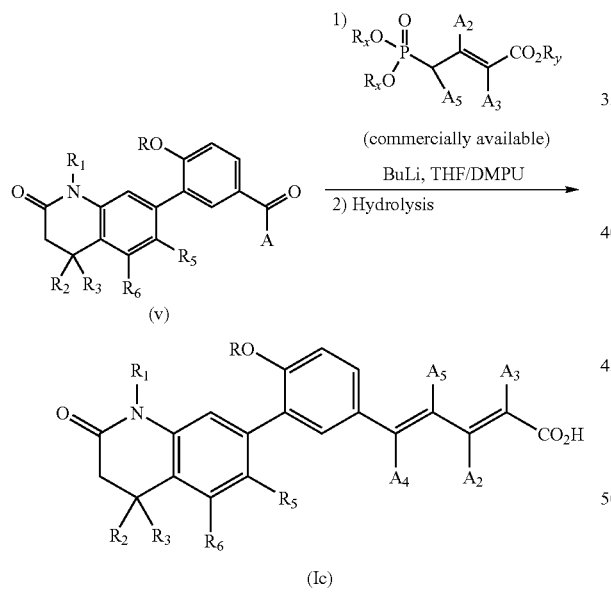

In accordance with Scheme 3 wherein $A_2$, $A_3$ $A_4$, and $A_5$ independently represent H, $CH_3$ optionally substituted by F, or F, and $R_5$ represents H or optionally substituted $C_{1-3}$alkyl, and $R_x$, $R_y$, $R_1$, $R_2$, $R_3$, and $R_6$ are as described hereinabove, compounds of (Ic) wherein 0-1 of $A_2$, $A_3$ $A_4$, and $A_5$ is $CH_3$ optionally substituted by F, can be synthesized.

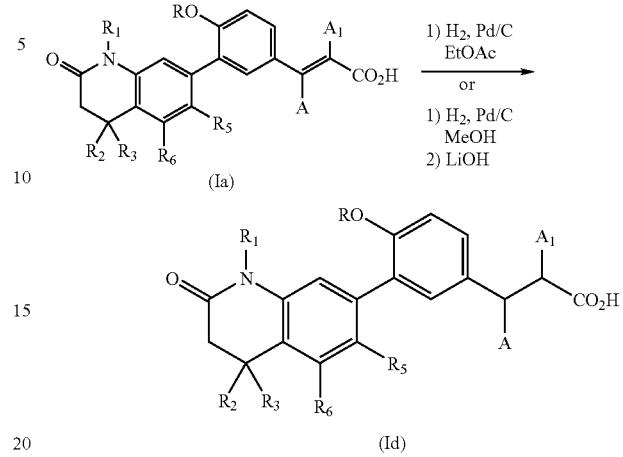

The double bonds of the phenylacrylic acids such as (Ia) synthesized by a sequence similar to the one shown in Schemes 1-3 can be reduced by hydrogenation with metal catalysts such as palladium on carbon to give corresponding carboxylic acids (Id), as shown in Scheme 4 wherein $R_5$ represents H or optionally substituted $C_{1-3}$alkyl, and A, $A_1$, $R_1$, R, $R_2$, $R_3$, and $R_6$ are as described hereinabove. The same acids can also be synthesized from the acrylic esters by hydrogenation followed by hydrolysis of the ester functionality.

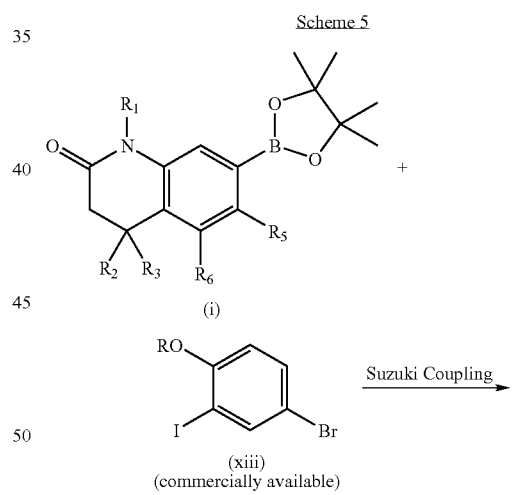

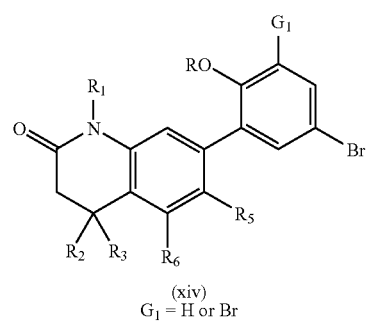

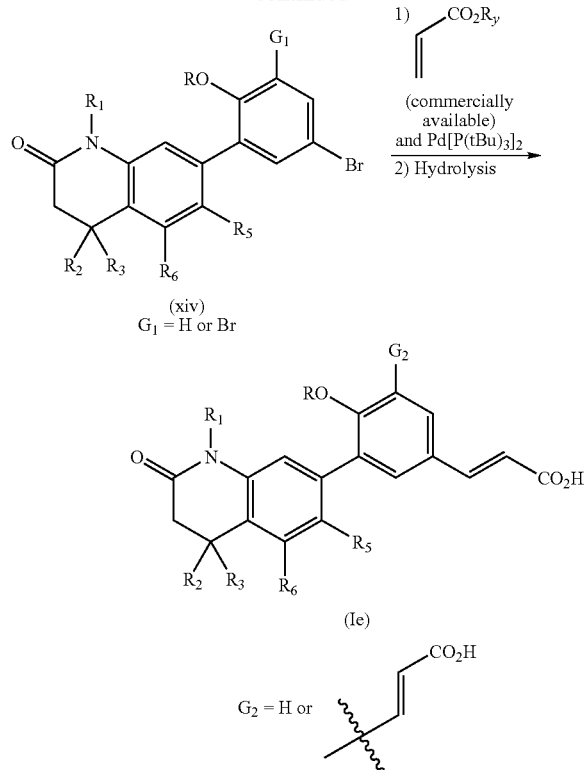

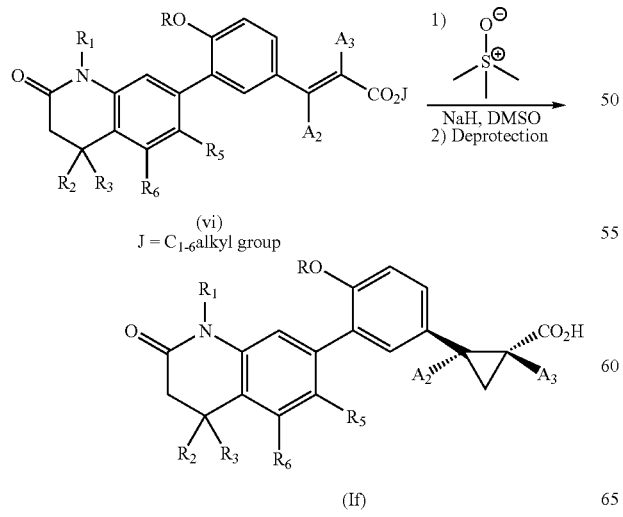

According to Scheme 5 wherein $G_1$ represents H or Br, and $G_2$ represents H or —CH=CH—CO$_2$H, and $R_5$ represents H or optionally substituted $C_{1-3}$alkyl, and R, $R_1$, $R_2$, $R_3$, and $R_6$ are as described hereinabove, the Suzuki reaction between the borinate ester such as (i) and 4-bromo-1-iodo-2-alkoxybenzene (xiii) results in the aryl bromide (xiv) which can be reacted with an acrylic ester under Heck reaction conditions using a palladium catalyst such as Pd[P(t-Bu)$_3$] to obtain acrylic esters, which upon hydrolysis can be converted into the corresponding acrylic acid (Ie).

As shown in Scheme 6 wherein J represents $C_{1-6}$alkyl, and $R_5$ represents H or optionally substituted $C_{1-3}$alkyl, and $A_2$, $A_3$, R, $R_1$, $R_2$, $R_3$, and $R_6$ are as described hereinabove, the cyclopropyl carboxylic acid (If) can be synthesized by a 1,4-addition of the ylide generated from trimethylsulfoxonium iodide and sodium hydride into the phenylacrylate ester (vi). The ester can then be hydrolyzed to give the corresponding carboxylic acid (If). Several other methods have been reported for the conversion of an acrylate ester into a cyclopropyl carboxylate ester such as the reaction of (vi) with diazomethane in the presence of a Palladium or Copper catalyst. See, for example, Denmark et al., Cyclopropanation with Diazomethane and Bis(oxazoline)palladium(II) Complexes, Journal of Organic Chemistry (1997), 62(10), 3375-3389; Charette et al., Bis(oxazoline)☐copper(I)-catalyzed enantioselective cyclopropanation of cinnamate esters with diazomethane, Tetrahedron: Asymmetry (2003), 14(7), 867-872; Eilbracht et al., Tandem silylformylation/Wittig olefination of terminal alkynes: stereoselective synthesis of 2,4-Dienoic esters, European Journal of Organic Chemistry (2000), (7), 1131-1135.

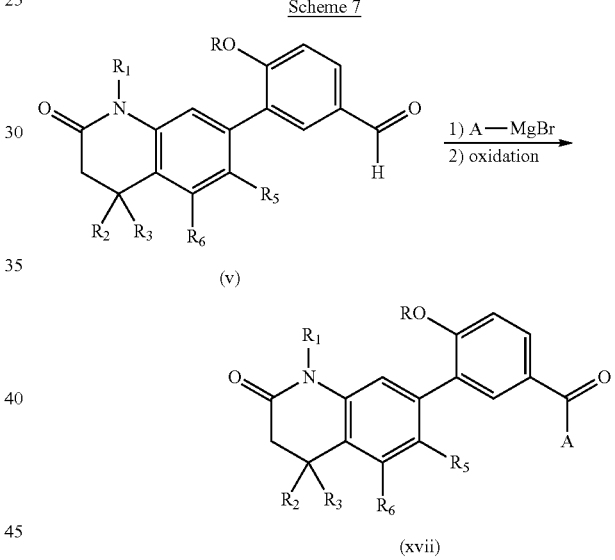

The benzaldehyde (v) can be converted into a corresponding ketone by addition of a alkyl or aryl Grignard reagent or an alkyl or aryllithium reagent into the aldehyde followed by oxidation of the corresponding secondary alcohol, as shown in Scheme 7 wherein $R_5$ represents H or optionally substituted $C_{1-3}$alkyl, and A, R, $R_1$, $R_2$, $R_3$, and $R_6$ are as described hereinabove.

Scheme 8

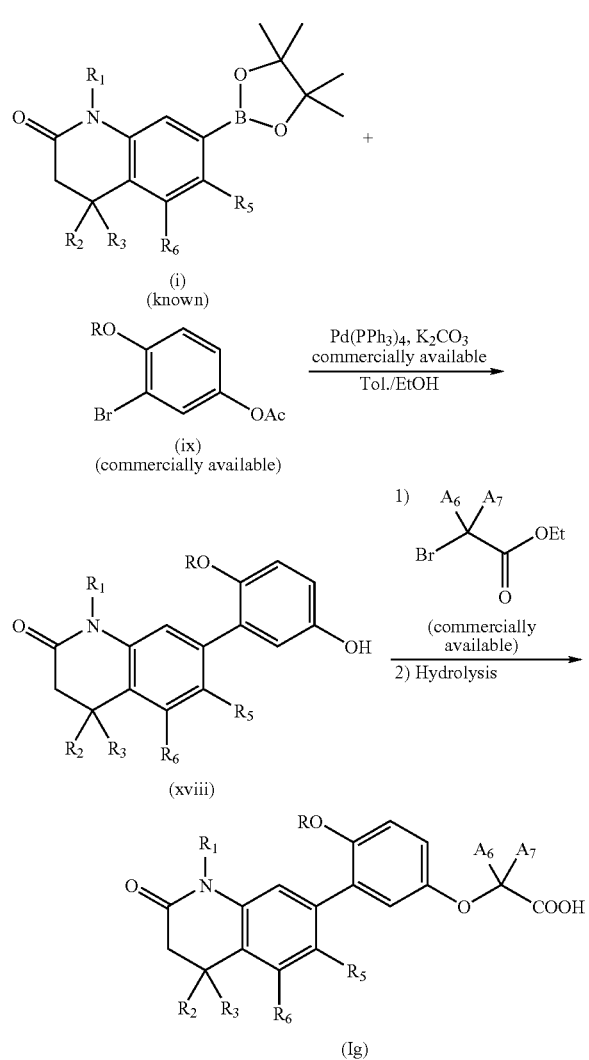

In accordance with Scheme 8 wherein $A_6$ and $A_7$ independently represent optionally substituted $C_{1-3}$alkyl, and $R_5$ represents H or optionally substituted $C_{1-3}$alkyl, and R, $R_1$, $R_2$, $R_3$, and $R_6$ are as described hereinabove, the Suzuki reaction between the borinate ester such as (i) and acetic acid-3-bromo-4-alkoxyphenyl ester (ix) results in the phenol (xviii) which can be reacted with □-bromo ester to obtain the □-phenoxy ester. The ester upon hydrolysis can be converted to the corresponding carboxylic acid (Ig).

Scheme 9

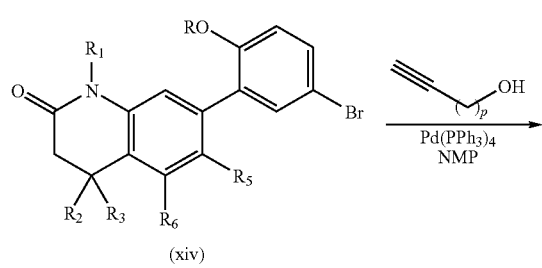

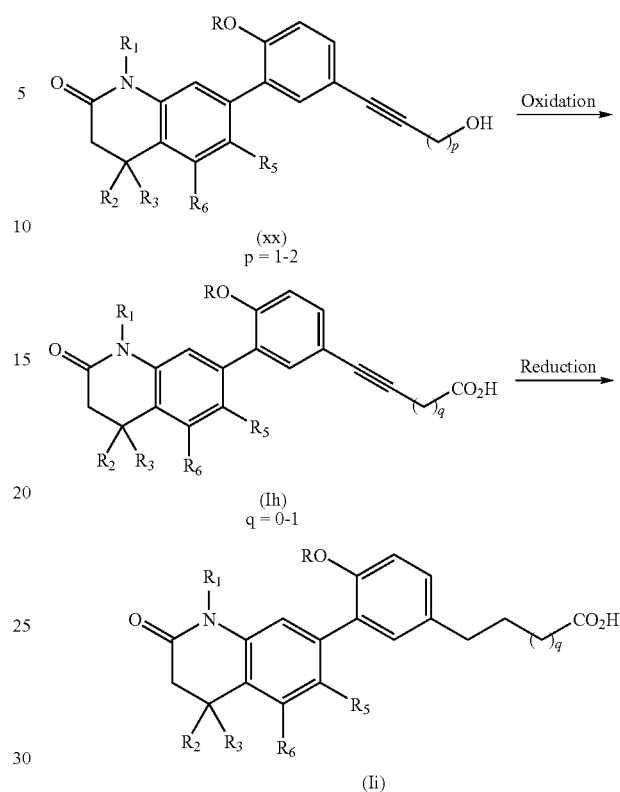

As shown in Scheme 9 wherein p is 1 or 2, and q is 0 or 1, and $R_5$ represents H or optionally substituted $C_{1-3}$alkyl, and R, $R_1$, $R_2$, $R_3$, and $R_6$ are as described hereinabove, the Sonogashira coupling between the bromide (xiv) and a substituted propargyl alcohol results in the intermediate alcohol (xx). The alcohol can be oxidized to yield the corresponding acid containing an alkyne (Ih). This alkyne containing carboxylic acid can be hydrogenated to a carboxylic acid (Ii).

Scheme 10

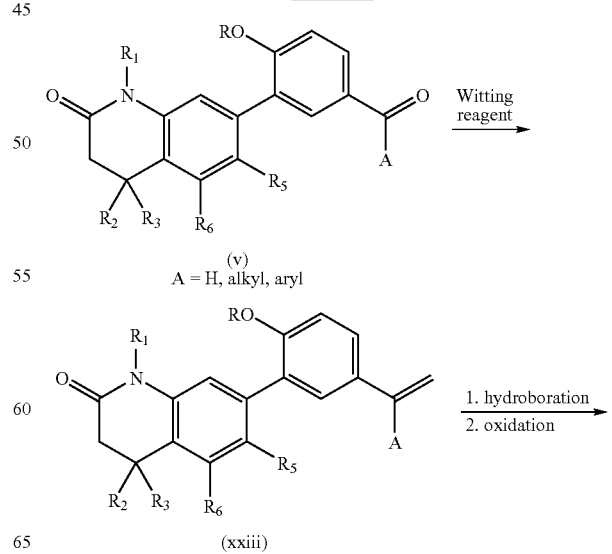

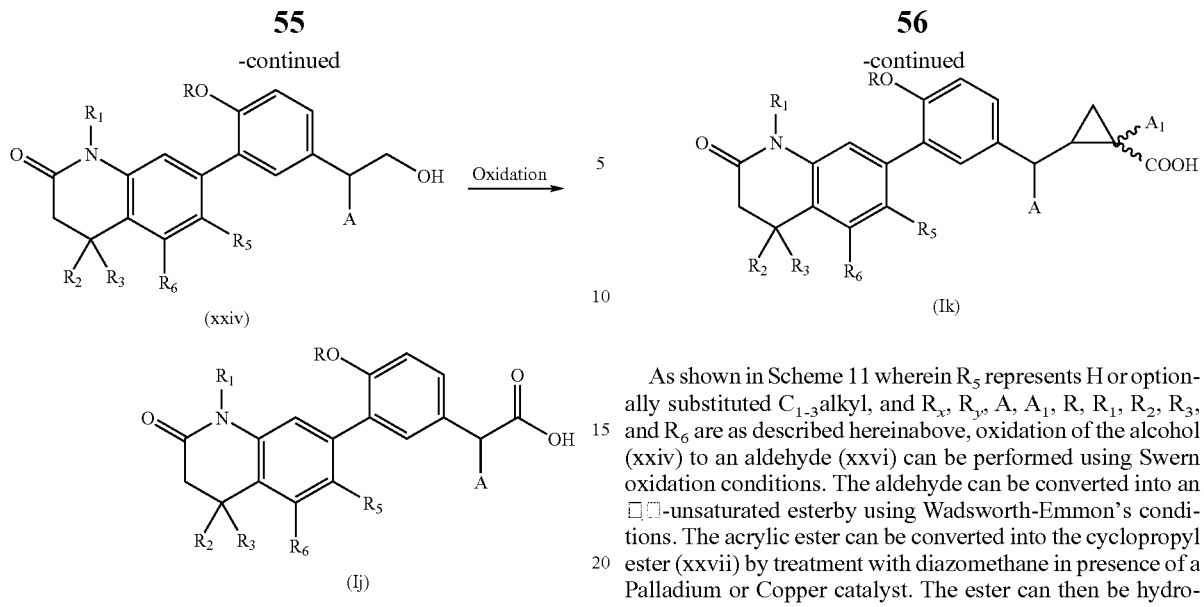

As demonstrated in Scheme 10, wherein $R_5$ represents H or optionally substituted $C_{1-3}$alkyl, and A, R, $R_1$, $R_2$, $R_3$, and $R_6$ are as described hereinabove, the compounds of (v) can be treated with a Witting reagent to yield substituted styrene (xxiii). The styrene upon hydroboration followed by oxidation yields a corresponding alcohol (xxiv) which can be further oxidized to obtain a carboxylic acid (Ij).

As shown in Scheme 11 wherein $R_5$ represents H or optionally substituted $C_{1-3}$alkyl, and $R_x$, $R_y$, A, $A_1$, R, $R_1$, $R_2$, $R_3$, and $R_6$ are as described hereinabove, oxidation of the alcohol (xxiv) to an aldehyde (xxvi) can be performed using Swern oxidation conditions. The aldehyde can be converted into an □,□-unsaturated esterby using Wadsworth-Emmon's conditions. The acrylic ester can be converted into the cyclopropyl ester (xxvii) by treatment with diazomethane in presence of a Palladium or Copper catalyst. The ester can then be hydrolyzed to give the corresponding carboxylic acid (Ik).

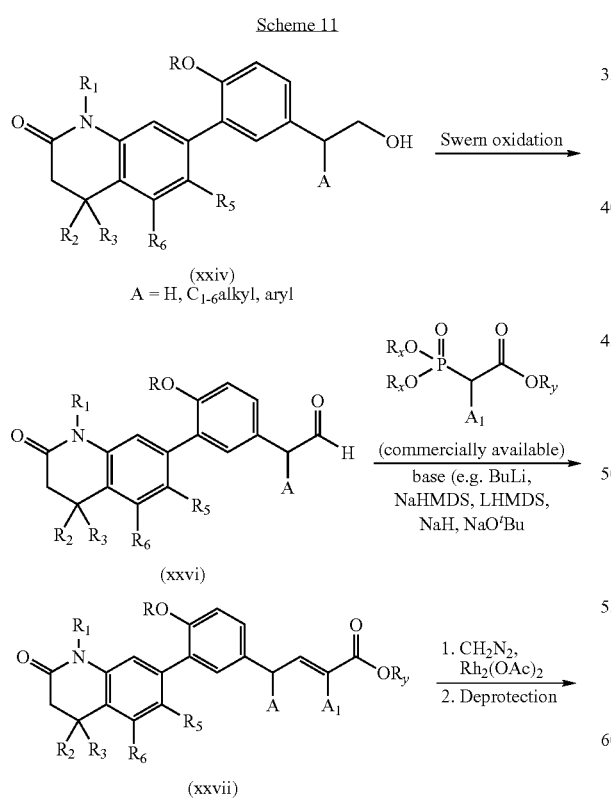

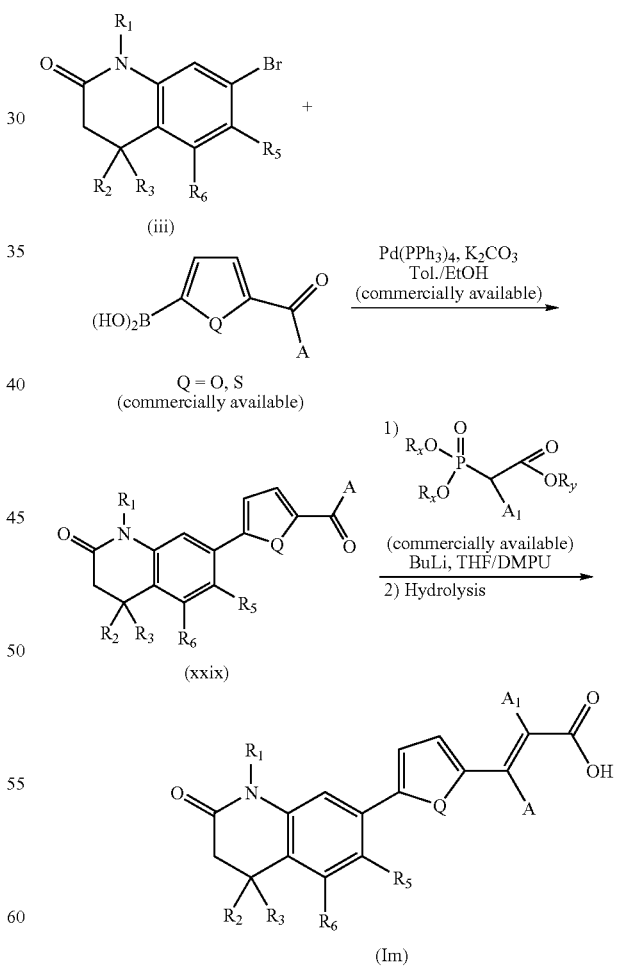

As demonstrated in Scheme 12 wherein Q represents O or S, and $R_5$ represents H or optionally substituted $C_{1-3}$alkyl, and A, $A_1$, R, $R_1$, $R_2$, $R_3$, and $R_6$ are as described hereinabove, a Suzuki reaction between a substituted thiophene-boronic acid (or a substituted 2-furanyl boronic acid) and an aryl bromide (iii), leads to the compounds of (xxix). Where A is hydrogen, the compounds of (xxix) can be treated with a Wadsworth-Emmon's reagent (modified Witting reagent) to yield substituted heteroarylacrylic esters which can be hydrolyzed to corresponding substituted heteroarylacrylic acids (Im) under acidic or basic conditions. It is obvious to one skilled in the art to make a compound similar to (Im) except that different carbon atoms in the

ring serve as the linkage points.

When $R_4$ is H or optionally substituted $C_{1-3}$ alkyl and $R_5$ is

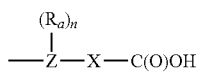

wherein Z, $R_a$, X are as described hereinabove, compounds of Formula I can be made in a similar fashion.

EXAMPLES

Example 1

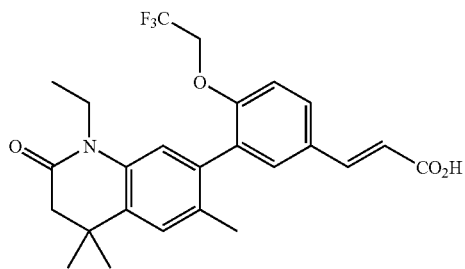

3-[3-(1-Ethyl-4,4,6-trimethyl-2-oxo-1,2,3,4-tetrahydro-quinolin-7-yl)-4-(2,2,2-trifluoro-ethoxy)-phenyl]-acrylic acid (Compound 1)

A. 7-Bromo-1-ethyl-4,4,6-trimethyl-3,4-dihydro-1H-quinolin-2-one (Compound 1A)

A solution of 8.5 g of 7-bromo-4,4,6-trimethyl-3,4-dihydro-1H-quinolin-2-one (31.7 mmol), prepared according to WO 03/075924, in 15 mL dry DMSO was added to a prestirred solution of crushed potassium hydroxide (3.56 g, 63.4 mmol) in 15 mL of dry DMSO, followed by addition of 7.68 mL (95.2 mmol) of ethyl iodide. The reaction was stirred overnight before quenching with 100 mL of water and extracted with dichloromethane (3×150 mL), the extracts were dried with sodium sulfate, filtered, stripped and purified via flash chromatography (5% EtOAc/hexanes) to afford 8.3 g of product (88%) as a white solid. MS (electrospray): mass calculated for $C_{14}H_{18}BrNO$, 295.06; m/z found 296, $[M+H]^+$.

B. 3-(1-Ethyl-4,4,6-trimethyl-2-oxo-1,2,3,4-tetrahydro-quinolin-7-yl)-4-methoxy-benzaldehyde (Compound 1B)

A round bottom flask was charged with 6.0 g of Compound 1A (20.3 mmol), 5.5 g of 2-methoxy-5-formylphenylboronic acid (30.4 mmol) and tetrakis(triphenylphosphine)palladium (0), (1.17 g, 0.10 mmol). The flask was sealed and 100 mL of toluene and 30 mL of ethanol was added. The resulting solution was stirred to dissolve the reactants and then 21 mL of 2M $K_2CO_3$ was added via syringe. The reaction mixture was heated to 80° C. for 4 hours. After cooling, the reaction mixture was partitioned between ethyl acetate (200 mL) and water (75 mL). The water layer was further extracted (2×100 mL) and the combined organic layers were washed with water (50 mL) followed by brine (50 mL), dried over magnesium sulfate, filtered and excess solvent removed on the rotary evaporator. The crude product was purified by flash chromatography (EtOAc/Hexanes; gradient 20% to 40%) to give 7.05 g (99%) of product Compound 1B as a foamy solid. MS (electrospray): mass calculated for $C_{22}H_{25}NO_3$, 351.18; m/z found 352.4, $[M+H]^+$. $^1$HNMR (300 MHz, $CDCl_3$): 9.94 (s, 1H), 7.93 (dd, J=2.1, 8.6 Hz, 1H), 7.73 (d, J=2.1 Hz, 1H), 7.18 (s, 1H), 7.12 (d, J=8.6 Hz, 1H), 6.85 (s, 1H), 4.01 (q, J=7.1 Hz, 2H), 3.90 (s, 3H), 2.52 (s, 2H), 2.10 (s, 3H), 1.33 (s, 6H), 1.23 (t, J=6.9 Hz, 3H).

C. 3-(1-Ethyl-4,4,6-trimethyl-2-oxo-1,2,3,4-tetrahydro-quinolin-7-yl)-4-hydroxy-benzaldehyde (Compound 1C)

A solution of 7.05 g of Compound 1B (20.1 mmol) in 60 mL of dry dichloromethane was treated with 40 mL of 1M $BBr_3$ in dichloromethane. The reaction flask was then equipped with a reflux condenser, nitrogen inlet and heated to reflux. After 2 hours another 20 mL of $BBr_3$ was added and refluxing continued for an additional 2 hours. The reaction mixture was allowed to cool to room temperature. The crude reaction mixture was diluted with dichloromethane and washed with water (2×50 mL) and brine (50 ml), dried over magnesium sulfate, filtered and excess solvent removed on the rotary evaporator. The crude product Compound 1C was purified by flash chromatography (EtOAc/Hexanes; gradient 15% to 30%) to give 3.6 g (53%) of product as a white solid. MS (electrospray): mass calculated for $C_{21}H_{23}NO_3$, 337.17; m/z found 338.3, $[M+H]^+$. $^1$HNMR (400 MHz, $CDCl_3$): 9.91 (s, 1H), 7.85 (dd, J=2.0, 8.5 Hz, 1H), 7.70 (d, J=1.98 Hz, 1H), 7.25 (s, 1H), 7.15 (d, J=8.4 Hz, 1H), 6.89 (s, 1H), 6.20 (s, 1H), 4.01 (q, J=7.1 Hz, 2H), 2.52 (s, 2H), 2.15 (s, 3H), 1.33 (s, 6H), 1.22 (t, J=7.09 Hz, 3H).

D. 3-(1-Ethyl-4,4,6-trimethyl-2-oxo-1,2,3,4-tetrahydro-quinolin-7-yl)-4-(2,2,2-trifluoro-ethoxy)-benzaldehyde (Compound 1D)

A solution of 3.6 g of Compound 1C (10.7 mmol) in 55 mL of acetone was treated with potassium carbonate (1.85 g, 13.4 mmol) and 2,2,2-trifluoroethyl nonafluorobutanesulfonate (2.99 mL, 12.8 mmol). The flask was equipped with a reflux condensor and heated in an oil bath to 55° C. for 4 hours. When the reaction was complete the flask was allowed to cool to room temperature and the solids were filtered off. The crude product was obtained by removal of excess solvent, followed by redissolving the product in chloroform and filtering off any remaining solids. Removal of the solvent yielded 4.4 g (100%) of product Compound 1D as a white solid. MS (electrospray): mass calculated for $C_{23}H_{24}F_3NO_3$, 419.17; m/z found 420.3, [M+H]+. 1HNMR (400 MHz, CDCl3): 9.97 (s, 1H), 7.94 (dd, J=2.01, 8.5 Hz, 1H), 7.76 (d, J=2.01 Hz, 1H), 7.18 (s, 1H), 7.11 (d, J=8.5 Hz, 1H), 6.83 (s, 1H), 4.41 (q, J=7.98 Hz, 2H), 3.99 (q, J=6.96 Hz, 2H), 2.53 (s, 2H), 2.10 (s, 3H), 1.33 (s, 6H), 1.21 (t, J=7.07 Hz, 3H).

E. 3-[3-(1-Ethyl-4,4,6-trimethyl-2-oxo-1,2,3,4-tetrahydro-quinolin-7-yl)-4-(2,2,2-trifluoro-ethoxy)-phenyl]-acrylic acid tert-butyl ester (Compound 1E)

A flask charged with 6.43 mL of dimethyl t-butoxycarbonyl-methylphosphonate (32 mmol) in 50 mL of dry THF/DMPU (10:1) was cooled to −78° C. where 12.8 mL of n-butyl lithium (2.5M hexane solution, 32 mmol) was added slowly via syringe. The reaction mixture was stirred at −78° C. for 10 minutes and then a solution of 4.4 g of Compound 1D (10.6 mmol) in 30 mL of dry THF was added. After warming to room temperature and an additional 20 minutes of stirring, the reaction was quenched with 30 mL of water and then partitioned with 30 mL of saturated ammonium chloride and 150 mL of ethyl acetate. The water layer was further extracted with ethyl acetate (2×75 mL) and the combined organic layers were then washed with brine (50 mL), dried over magnesium sulfate, filtered and excess solvent was removed on the rotary evaporator. The crude product was purified by flash chromatography (EtOAc/Hexanes; gradient 15% to 30%) to give 3.6 g (96%) of product Compound 1E as a white solid. MS (electrospray): mass calculated for $C_{29}H_{34}F_3NO_4$, 517.24; m/z found 518.4, [M+H]+. 1HNMR (300 MHz, CDCl3): 7.56 (d, J=16.5 Hz, 1H), 7.52 (dd, J=2.0, 8.5 Hz, 1H), 7.38 (d, J=2.01 Hz, 1H), 7.16 (s, 1H), 6.98 (d, J=8.5 Hz, 1H), 6.82 (s, 1H), 6.30 (d, J=16.5 Hz, 1H), 4.31 (q, J=8.0 Hz, 2H), 3.99 (q, J=5.1 Hz, 2H), 2.51 (s, 2H), 2.13 (s, 3H), 1.52 (s, 9H), 1.32 (s, 6H), 1.21 (t, J=7.07 Hz, 3H).

F. 3-[3-(1-Ethyl-4,4,6-trimethyl-2-oxo-1,2,3,4-tetrahydro-quinolin-7-yl)-4-(2,2,2-trifluoro-ethoxy)-phenyl]-acrylic acid (Compound 1)

A solution of 5.24 g of Compound 1E (10.1 mmol) in 50 mL of dichloromethane and 10 mL of trifluoroacetic acid was stirred at room temperature overnight. The reaction mixture was then concentrated on the rotary evaporator and redissolved in 30 mL of diethyl ether. To this solution, hexanes were added to give a cloudy solution from which 4.3 g (92%) of product (Compound 1) precipitated out as a white solid with a melting point range of 237-241° C. MS (electrospray): mass calculated for $C_{25}H_{26}F_3NO_4$, 461.18; m/z found 462.3, [M+H]+. 1HNMR (300 MHz, CDCl3): 7.78 (d, J=16.2 Hz, 1H), 7.6 (dd, J=2.01, 8.5 Hz, 1H), 7.44 (d, J=2.01 Hz, 1H), 7.18 (s, 1H), 7.02 (d, J=8.5 Hz, 1H), 6.85 (s, 1H), 6.39 (d, J=16.5 Hz, 1H), 4.35 (q, J=8.0 Hz, 2H), 4.02 (q, J=5.1 Hz, 2H), 2.56 (s, 2H), 2.12 (s, 3H), 1.33 (s, 6H), 1.22 (t, J=7.07 Hz, 3H). Anal. Calcd. for $C_{25}H_{26}F_3NO_4$: C, 65.07; H, 5.68; N, 3.04. Found C, 65.16; H, 5.81; N, 2.96.

Example 2

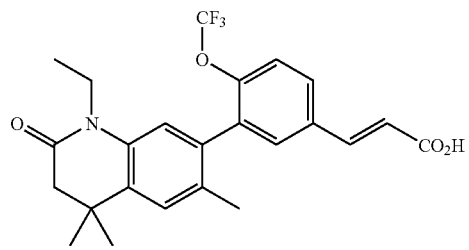

3-[3-(1-Ethyl-4,4,6-trimethyl-2-oxo-1,2,3,4-tetrahydro-quinolin-7-yl)-4-trifluoromethoxy-phenyl]-acrylic acid (Compound 2)

A. 3-(1-Ethyl-4,4,6-trimethyl-2-oxo-1,2,3,4-tetrahydro-quinolin-7-yl)-4-trifluoromethoxy-benzaldehyde (Compound 2A)

A solution of Compound 1A (1 g, 3.38 mmol) in 17 mL of toluene was added to a flask containing 2-trifluoromethoxy-5-formyl-phenyl boronic acid (0.95 g, 4.05 mmol), prepared by the procedure described in WO 03/075924, and tetrakis(triphenylphosphine)palladium(0) (195 mg, 0.17 mmol) in 4 mL of toluene. Next, 3.4 mL of a 2M solution of potassium carbonate was added and the reaction heated to reflux for four hours, after which the reaction was cooled and partitioned between ethyl acetate (100 mL) and water (50 mL). The aqueous layer was further extracted with ethyl acetate (2×100 mL) and the combined organic layers were dried with sodium sulfate, filtered, stripped and purified via flash chromatography (15% EtOAc/hexanes) to afford 890 mg of product Compound 2A (65%). MS (electrospray): mass calculated for $C_{22}H_{22}F_3NO_3$, 405.16; m/z found 406.2, [M+H]+.

B. 3-[3-(1-Ethyl-4,4,6-trimethyl-2-oxo-1,2,3,4-tetrahydro-quinolin-7-yl)-4-trifluoromethoxy-phenyl]-acrylic acid tert-butyl ester (Compound 2B)

Compound 2B was made from Compound 2A using a procedure similar to that described for Example 1E. MS (electrospray): mass calculated for $C_{28}H_{32}F_3NO_4$, 503.23; m/z found 504.1, [M+H]+. 1HNMR (400 MHz, CDCl3): 7.58 (d, J=16.7 Hz, 1H), 7.56 (dd, J=2.3, 8.6 Hz, 1H), 7.44 (d, J=2.2 Hz, 1H), 7.37 (dd, J=1.5, 8.6 Hz, 1H), 7.17 (d, J=8.5 Hz, 1H), 6.82 (s, 1H), 6.37 (d, J=16.1 Hz, 1H), 4.01 (br d, J=56.2 Hz, 2H), 2.52 (s, 2H), 2.09 (s, 3H), 1.53 (s, 9H), 1.32 (s, 6H), 1.20 (t, J=6.9 Hz, 3H).

C. 3-[3-(1-Ethyl-4,4,6-trimethyl-2-oxo-1,2,3,4-tetrahydro-quinolin-7-yl)-4-trifluoromethoxy-phenyl]-acrylic acid (Compound 2)

Compound 2 was made from Compound 2B using a procedure similar to that described in Example 1F. MS (electrospray): mass calculated for $C_{24}H_{24}F_3NO_4$, 447.17; m/z found 448.4, [M+H]+. 1HNMR (300 MHz, CDCl3): 7.79 (d, J=15.9 Hz, 1H), 7.62 (dd, 2.19, 8.6 Hz, 1H), 7.47 (d, J=2.16 Hz, 1H), 7.41 (dd, J=1.50, 8.56 Hz, 1H), 7.20 (s, 1H), 6.45 (d, J=16.0 Hz, 1H), 4.01 (br, 2H), 2.56 (s, 2H), 2.11 (s, 3H), 1.33 (s, 6H), 1.21 (t, J=6.99 Hz, 3H).

Example 3

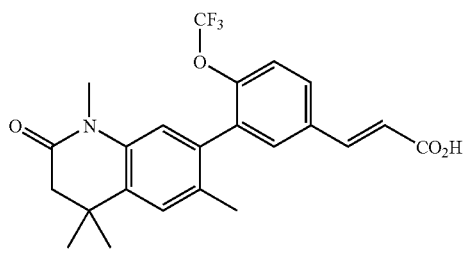

3-[3-(1,4,4,6-Tetramethyl-2-oxo-1,2,3,4-tetrahydro-quinolin-7-yl)-4-trifluoromethoxy-phenyl]-acrylic acid (Compound 3)

A. 7-Bromo-1,4,4,6-tetramethyl-3,4-dihydro-1H-quinolin-2-one (Compound 3A)

Compound 3A was prepared using a procedure similar to that described in Example 1A, except using methyl iodide as the alkylating reagent. MS (electrospray): mass calculated for $C_{13}H_{16}BrNO$, 281.04; m/z found 282 [M+H]$^+$.

B. 3-[3-(1,4,4,6-Tetramethyl-2-oxo-1,2,3,4-tetrahydro-quinolin-7-yl)-4-trifluoromethoxy-phenyl]-acrylicacid (Compound 3)

Compound 3 was prepared from Compound 3A using a procedure similar to that described for Example 2. MS (electrospray): mass calculated for $C_{23}H_{22}F_3NO_4$, 433.15; m/z found 434.2 [M+H]$^+$. $^1$HNMR (300 MHz, CDCl$_3$): 7.59 (d, J=16.2 Hz, 1H), 7.55 (dd, J=2.8, 8.5 Hz, 1H), 7.43 (d, J=2.8 Hz, 1H), 7.17 (s, 1H), 7.02 (d, J=8.5 Hz, 1H), 6.77 (s, 1H), 6.36 (d, J=16.5 Hz, 1H), 3.34 (s, 3H), 2.54 (s, 2H), 2.10 (s, 3H), 1.33 (s, 6H).

Example 4

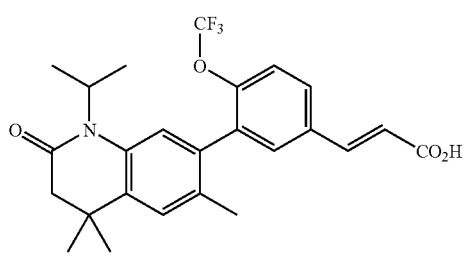

3-[3-(1-isopropyl-4,4,6-trimethyl-2-oxo-1,2,3,4-tetrahydro-quinolin-7-yl)-4-trifluoromethoxy-phenyl]-acrylic acid (Compound 4)

A. 7-Bromo-1-isopropyl-4,4,6-trimethyl-3,4-dihydro-1H-quinolin-2-one Compound 4A)

Compound 4A was prepared using a procedure similar to that described in Example 1A, except using 2-iodopropane as the alkylating reagent. MS (electrospray): mass calculated for $C_{15}H_{20}BrNO$, 309.07; m/z found 310.1 [M+H]$^+$.

B. 3-[3-(1-Isopropyl-4,4,6-trimethyl-2-oxo-1,2,3,4-tetrahydro-quinolin-7-yl)-4-trifluoromethoxy-phenyl]-acrylic acid (Compound 4)

Compound 4 was prepared from Compound 4A using a procedure similar to that described for Example 2. MS (electrospray): mass calculated for $C_{25}H_{26}F_3NO_4$, 461.18; m/z found 462.2 [M+H]$^+$. $^1$HNMR (300 MHz, CDCl$_3$): 7.78 (d, J=16.2 Hz, 1H), 7.6 (dd, J=2.01, 8.5 Hz, 1H), 7.44 (d, J=2.01 Hz, 1H), 7.18 (s, 1H), 7.13 (d, J=8.5 Hz, 1H), 6.96 (s, 1H), 6.46 (d, J=16.5 Hz, 1H), 4.68 (septet, J=7.2 Hz, 1H), 2.50 (s, 2H), 2.12 (s, 3H), 1.45 (d, J=7.2 Hz, 6H), 1.34 (s, 6H).

Example 5

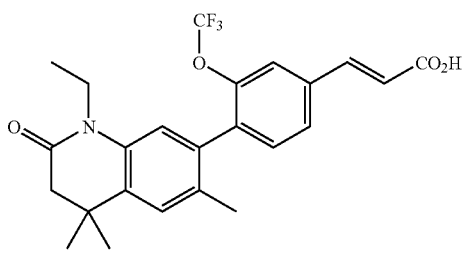

3-[4-(1-Ethyl-4,4,6-trimethyl-2-oxo-1,2,3,4-tetrahydro-quinolin-7-yl)-3-trifluoromethoxy-phenyl]-acrylic acid (Compound 5)

A. 1-Ethyl-4,4,6-trimethyl-7-(4,4,5,5-tetramethyl-[1,3,2]dioxaborolan-2-yl)-3,4-dihydro-1H-quinolin-2-one (Compound 5A)

Compound 5A was prepared according to Pfahl et al. in WO 03/075924.

B. 7-(4-Bromo-2-trifluoromethoxy-phenyl)-1-ethyl-4,4,6-trimethyl-3,4-dihydro-1H-quinolin-2-one (Compound 5B)

Compound 5B was prepared from Compound 5A and 4-bromo-1-iodo-2-trifluoromethoxy-benzene using a the conditions described for Example 1B. MS (electrospray): mass calculated for $C_{21}H_{21}BrF_3NO_2$, 455.07; m/z found 456.1 [M+H]$^+$.

C. 3-[4-(1-Ethyl-4,4,6-trimethyl-2-oxo-1,2,3,4-tetrahydro-quinolin-7-yl)-3-trifluoromethoxy-phenyl]-acrylic acid tert-butyl ester (Compound 5C)

A sealed tube was charged with Pd[P(tBu)$_3$]$_2$ (4 mg, 0.0075 mmol), tert-butyl acrylate (0.03 mL, 0.18 mmol) and Compound 5B (68 mg, 0.15 mmol) in 1 mL of dry dioxane. To this was added dicyclohexyl methyl amine (0.04 mL, 0.18 mmol) and the tube was sealed and heated to 80° C. overnight. After the reaction was cooled, 3 mL of water was added and the solution was passed through a 5 mL solid phase extraction (SPE) column. The SPE was washed with dichloromethane and the collected eluant was stripped on the roto yap to give crude product Compound 5C which was further purified by flash chromatography (25% EtOAc/Hexane) to yield 45 mg (60%) of product. MS (electrospray): mass calculated for $C_{28}H_{32}F_3NO_4$, 503.23; m/z found 504.2 [M+H]$^+$.

D. 3-[4-(1-Ethyl-4,4,6-trimethyl-2-oxo-1,2,3,4-tetrahydro-quinolin-7-0)-3-trifluoromethoxy-phenyl]-acrylic acid (Compound 5)

Compound 5 was prepared from Compound 5C using the procedure described in Example 1F. MS (electrospray): mass calculated for $C_{24}H_{24}F_3NO_4$, 447.17; m/z found 448.2 [M+H]$^+$.

Example 6

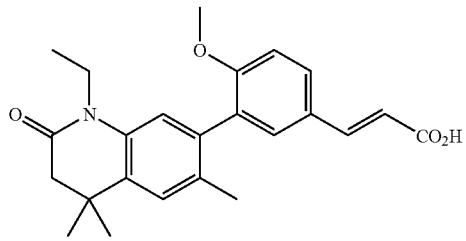

3-[3-(1-Ethyl-4,4,6-trimethyl-2-oxo-1,2,3,4-tetrahydro-quinolin-7-yl)-4-methoxy-phenyl]-acrylic acid (Compound 6)

Compound 6 was prepared using the procedures described in Example 2, except using 2-methoxy-5-formyl-phenyl boronic acid as the starting material in step 2A. MS (electrospray): mass calculated for $C_{24}H_{27}NO_4$, 393.19; m/z found, 394.2 [M+H]$^+$.

Example 7

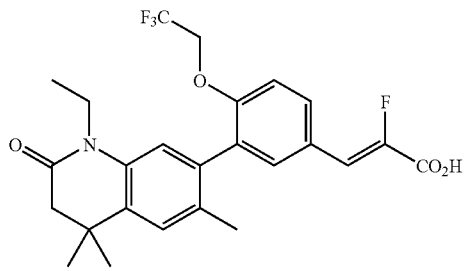

3-[3-(1-Ethyl-4,4,6-trimethyl-2-oxo-1,2,3,4-tetrahydro-quinolin-7-yl)-4-(2,2,2-trifluoro-ethoxy)-phenyl]-2-fluoro-acrylic acid (Compound 7)

Compound 7 was prepared using the procedures described in Example 1, except using triethyl-2-fluoro-2-phosphonoacetate in step 1E. MS (electrospray): mass calculated for $C_{25}H_{25}F_4NO_4$, 479.17; m/z found 480.2 [M+H]$^+$.

Example 8

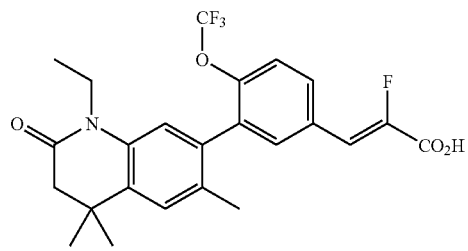

3-[3-(1-Ethyl-4,4,6-trimethyl-2-oxo-1,2,3,4-tetrahydro-quinolin-7-yl)-4-trifluoromethoxy-phenyl]-2-fluoro-acrylic acid (Compound 8)

Compound 8 was prepared using the procedure described in Example 2, except using triethyl-2-fluoro-2-phosphonoacetate in step 2B. MS (electrospray): mass calculated for $C_{24}H_{23}F_4NO_4$, 465.16; m/z found 466.2 [M+H]$^+$.

Example 9

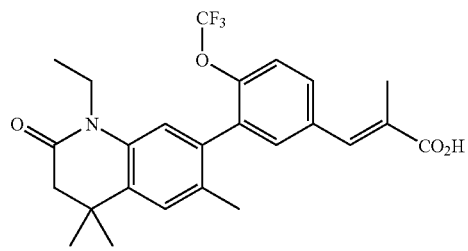

3-[3-(1-Ethyl-4,4,6-trimethyl-2-oxo-1,2,3,4-tetrahydro-quinolin-7-yl)-4-trifluoromethoxy-phenyl]-2-methyl-acrylic acid (Compound 9)

A. 1-Ethyl-4,4,6-trimethyl-7-(2-trifluoromethoxy-phenyl)-3,4-dihydro-1H-quinolin-2-one (Compound 9A)

Compound 9A was prepared from Compound 1A using the procedure described in Example 1B, except using 2-trifluoromethoxy benzene boronic acid as the starting material. MS (electrospray): mass calculated for $C_{21}H_{22}F_3NO_2$ 377.16; m/z found m/z found, 378.2 [M+H]$^+$.

B. 7-(5-Bromo-2-trifluoromethoxy-phenyl)-1-ethyl-4,4,6-trimethyl-3,4-dihydro-1H-quinolin-2-one (Compound 9B)

A solution of Compound 9A (1.31 g, 3.48 mmol) in 18 mL of nitromethane, was treated with anhydrous $FeCl_3$ (620 mg, 3.82 mmol) followed by a solution of bromine (0.18 mL, 3.48 mmol) in 4 mL of nitromethane overnight at room temperature. The reaction was then partitioned between 75 mL of water and 150 mL of dichloromethane, the aqueous layer was further extracted with 2×75 mL of dichloromethane. The combined organic layers were dried with sodium sulfate, filtered and stripped to give crude product which was purified via flash chromatography (gradient 5% to 10% EtoAc/hexanes) to yield 1.16 g (82%) of mono (para) brominated product (Compound 9B), along with 538 mg of dibrominated (ortho, para) product. MS (electrospray): mass calculated for $C_{21}H_{21}BrF_3NO_2$, 455.07; m/z found 456.1 $[M+H]^+$.

C. 3-[3-(1-Ethyl-4,4,6-trimethyl-2-oxo-1,2,3,4-tetrahydro-quinolin-7-yl)-4-trifluoromethoxy-phenyl]-2-methyl-acrylic acid tert-butyl ester (Compound 9C)

Compound 9C was prepared form Compound 9B using a procedure similar to that described for Example 5C, except that t-butyl methacrylate was used as the coupling reagent. MS (electrospray): mass calculated for $C_{26}H_{28}F_3NO_4$, 475.20; m/z found, 476.2[M+H]$^+$.

D. 3-[3-(1-Ethyl-4,4,6-trimethyl-2-oxo-1,2,3,4-tetrahydro-quinolin-7-yl)-4-trifluoromethoxy-phenyl]-2-methyl-acrylic acid (Compound 9)

Compound 9 was prepared from Compound 9C using a procedure similar to that used for Example 1F. MS (electrospray): mass calculated for $C_{25}H_{26}F_3NO_4$, 461.18; m/z found, 462.2 [M+H]$^+$.

Example 10

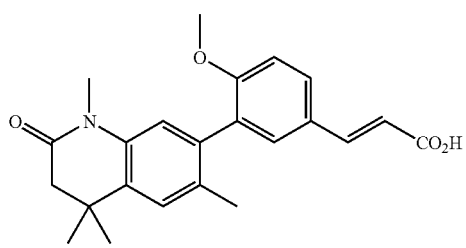

3-[4-Methoxy-3-(1,4,4,6-tetramethyl-2-oxo-1,2,3,4-tetrahydro-quinolin-7-yl)-phenyl]-acrylic acid (Compound 10)

Compound 10 was prepared from Compound 3A using a procedure similar to that described in Example 2 except using 2-methoxy-5-formyl-phenyl boronic acid as the starting material in step 2A. MS (electrospray): mass calculated for $C_{22}H_{25}NO_3$, 379.18; m/z found, 380.2 [M+H]$^+$.

Example 11

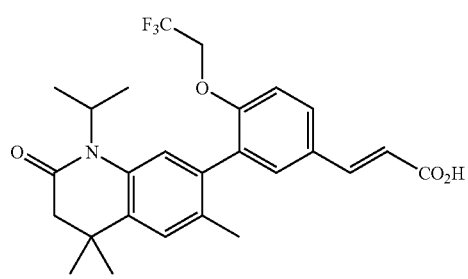

3-[3-(1-Isopropyl-4,4,6-trimethyl-2-oxo-1,2,3,4-tetrahydro-quinolin-7-yl)-4-(2,2,2-trifluoro-ethoxy)-phenyl]-acrylic acid (Compound 11)

Compound 11 was prepared from Compound 4A using a procedure similar to that described in Example 1. MS (electrospray): mass calculated for $C_{26}H_{28}F_3NO_4$, 475.20; m/z found, 476.2 [M+H]$^+$.

Example 12

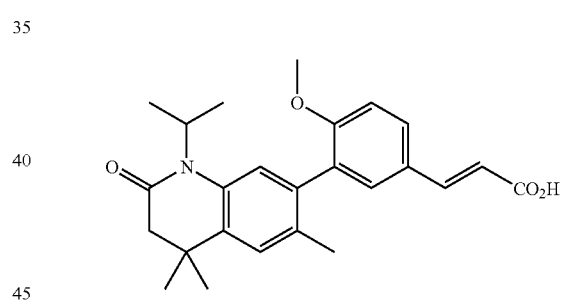

3-[3-(1-isopropyl-4,4,6-trimethyl-2-oxo-1,2,3,4-tetrahydro-quinolin-7-yl)-4-methoxy-phenyl]-acrylic acid (Compound 12)

Compound 12 was prepared from Compound 4A using a procedure similar to that described in Example 2, except using 2-methoxy-5-formyl-phenyl boronic acid as the starting material in 2A. MS (electrospray): mass calculated for $C_{25}H_{29}NO_4$, 407.21; m/z found 408 $[M+H]^+$.

Example 13

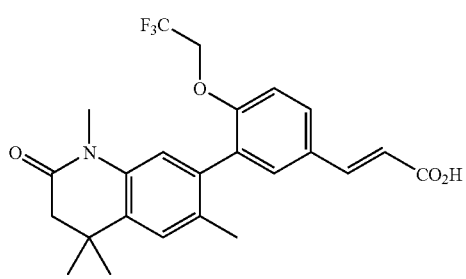

3-[3-(1,4,4,6-Tetramethyl-2-oxo-1,2,3,4-tetrahydro-quinolin-7-yl)-4-(2,2,2-trifluoro-ethoxy)-phenyl]-acrylic acid (Compound 13)

Compound 13 was prepared using a procedure similar to that described in Example 1, except using Compound 3A, as the starting material. MS (electrospray): mass calculated for $C_{24}H_{24}F_3NO_4$, 447.17; m/z found, 447.2 $[M+H]^+$.

Example 14

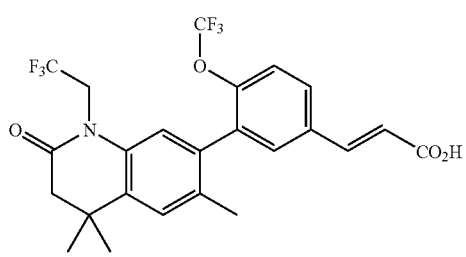

3-{4-Trifluoromethoxy-3-[4,4,6-trimethyl-2-oxo-1-(2,2,2-trifluoro-ethyl)-1,2,3,4-tetrahydro-quinolin-7-yl]-phenyl}-acrylic acid A. 7-Bromo-4,4,6-trimethyl-1-(2,2,2-trifluoro-ethyl)-3,4-dihydro-1H-quinolin-2-one (Compound 14A)

Compound 14A was prepared using a procedure similar to that described in Example 1A, except using 2,2,2-trifluoro-ethyliodide as the alkylating reagent. MS (electrospray): mass calculated for $C_{14}H_{15}BrF_3NO$, 349.03; m/z found 350 $[M+H]^+$.

B. 3-{4-Trifluoromethoxy-3-[4,4,6-trimethyl-2-oxo-1-(2,2,2-trifluoro-ethyl)-1,2,3,4-tetrahydro-quinolin-7-yl]-phenyl}-acrylic acid (Compound 14)

Compound 14 was prepared from Compound 14A using a procedure similar to that described for Example 2. MS (electrospray): mass calculated for $C_{24}H_{21}F_6NO_4$, 501.14; m/z found 502.1 $[M+H]^+$.

Example 15

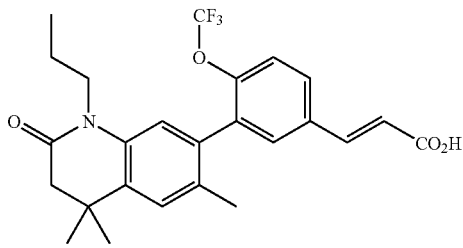

3-[4-Trifluoromethoxy-3-(4,4,6-trimethyl-2-oxo-1-propyl-1,2,3,4-tetrahydro-quinolin-7-1/1)-phenyl]-acrylic acid (Compound 15)

A. 7-Bromo-4,4,6-trimethyl-1-propyl-3,4-dihydro-1H-quinolin-2-one (Compound 15A)

Compound 15A was prepared using a procedure similar to that described in Example 1A, except using n-propyliodide as the alkylating reagent. MS (electrospray): mass calculated for $C_{15}H_{20}BrNO$, 309.07; m/z found 310 $[M+H]^+$.

B. 3-[4-Trifluoromethoxy-3-(4,4,6-trimethyl-2-oxo-1-propyl-1,2,3,4-tetrahydro-quinolin-7-yl)-phenyl]-acrylic acid (Compound 15)

This was prepared from Compound 15A using a procedure similar to that described for Example 2. MS (electrospray): mass calculated for $C_{25}H_{26}F_3NO_4$, 461.18; m/z found 462.2 $[M+H]^+$.

Example 16

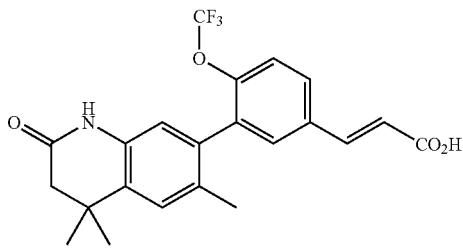

3-[4-Trifluoromethoxy-3-(4,4,6-trimethyl-2-oxo-1,2, 3,4-tetrahydro-quinolin-7-yl)-phenyl]-acrylic acid (Compound 16)

A. 7-Bromo-4,4,6-trimethyl-3,4-dihydro-1H-quinolin-2-one (Compound 16A)

Compound 16A was synthesized by the procedure described in WO 03/075924.

B. 7-Bromo-4,4,6-trimethyl-2-oxo-3,4-dihydro-2H-quinoline-1-carboxylic acid tert-butyl ester (Compound 16B), To a solution of Compound 16A (7-bromo-4,4,6-trimethyl-3,4-dihydro-1H-quinolin-2-one; 204 mg, 1.0 eq.) in 20 mL of anhydrous THF was added NaH (38 mg, 2.0 eq.). Reaction was allowed to stir for 2 hours, (Boc)$_2$O (500 mg, 3.0 eq.) was added and reaction was continued to stir overnight. The reaction was partitioned between ethyl acetate (50 mL) and ammonium chloride (50 mL). The aqueous layer was further extracted with ethyl acetate (1×50 mL) and the combined organics were dried over sodium sulfate, filtered and excess solvent was removed on the rotary evaporator. The crude product (Compound 16B) was purified by flash chromatography (90:10 hexanes/EtOAc/Hexanes) to give 274 mg (98%) of product as colorless oil. MS (electrospray): mass calculated for $C_{17}H_{22}BrNO_3$, 368.27; m/z found 391.4, [M+Na]$^+$.

C. 7-(5-Formyl-2-trifluoromethoxy-phenyl)-4,4,6-trimethyl-2-oxo-3,4-dihydro-2H-quinoline-1-carboxylic acid tert-butyl ester (Compound 16B)

This was prepared from Compound 16B using the procedure described in Example 2A. Purification by flash chromatography (95:5, 90:10 hexanes/EtOAc) afforded 158 mg (45%) of product as yellow oil. MS (electrospray): mass calculated for $C_{25}H_{26}F_3NO_5$, 477.47; m/z found 500.2, [M+Na]$^+$.

D. 3-[4-Trifluoromethoxy-3-(4,4,6-trimethyl-2-oxo-1,2,3,4-tetrahydro-quinolin-7-yl)-phenyl]-acrylic acid (Compound 16)

This was prepared from Compound 16C using the procedure described in Example 2B and 2C. Trituration of the product with $CH_2Cl_2$ afforded 25 mg of product (Compound 16) as white solid (99+% purity by LC/MS). MS (electrospray): mass calculated for $C_{22}H_{20}F_3NO_4$, 419.39; m/z found 420.3, [M+H]$^+$.

Example 17

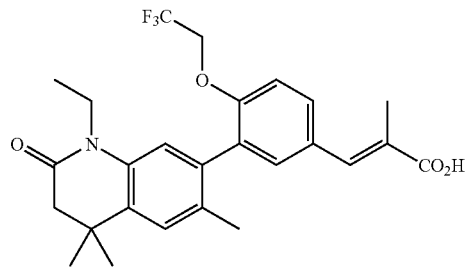

3-[3-(1-Ethyl-4,4,6-trimethyl-2-oxo-1,2,3,4-tetrahydro-quinolin-7-yl)-4-(2,2,2-trifluoro-ethoxy)-phenyl]-but-2-enoic acid (Compound 17)

Compound 17 was prepared according to the procedure similar to that described for Example 1, except that triethyl-2-phosphonopropionate was used in step 1E. MS (electrospray): mass calculated for $C_{26}H_{28}F_3NO_4$, 47520; m/z found, 476.2 [M+H]$^+$.

Example 18

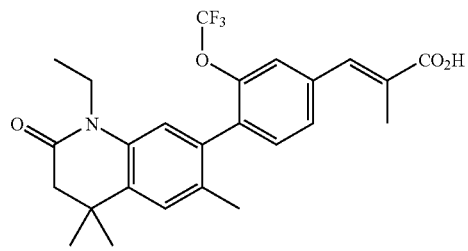

3-[4-(1-Ethyl-4,4,6-trimethyl-2-oxo-1,2,3,4-tetrahydro-quinolin-7-yl)-3-trifluoromethoxy-phenyl]-2-methyl-acrylic acid (Compound 18)

Compound 18 was prepared using a procedure similar to that described for Example 5 except that t-butyl methacrylate was used as the coupling reagent in step 5C. MS (electrospray): mass calculated for $C_{25}H_{26}F_3NO_4$, 461.18; m/z found 462.2 $[M+H]^+$.

Example 19

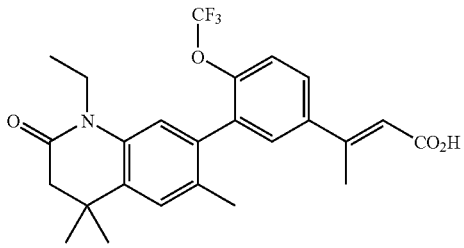

3-[3-(1-Ethyl-4,4,6-trimethyl-2-oxo-1,2,3,4-tetrahydro-quinolin-7-yl)-4-trifluoromethoxy-phenyl]-but-2-enoic acid (Compound 19)

A. 7-(5-Acetyl-2-trifluoromethoxy-phenyl)-1-ethyl-4,4,6-trimethyl-3,4-dihydro-1H-quinolin-2-one (Compound 19A)

A solution of Compound 2A (270 mg, 0.66 mmol) in 3 mL of dry THF was cooled to −78° C. and treated with a 3M solution of methyl magnesium bromide in ether (0.24 mL, 0.73 mmol). The reaction mixture was allowed to slowly warm to room temperature where it was quenched with 10 mL of a saturated ammonium chloride solution. The reaction mixture was then passed through a 10 mL SPE (solid phase extraction) column which was further washed with dichloromethane. The eluant was collected and stripped to give crude alcohol which was then dissolved in dichloromethane and treated with Dess-Martin reagent (336 mg, 0.79 mmol) and stirred at room temperature overnight. The reaction was quenched with 4 mL of saturated sodium thiosulfate solution and 4 mL of saturated sodium bicarbonate solution, the reaction mixture was stirred until clear. The reaction mixture was passed through another SPE and eluted with dichloromethane, removal of solvent yielded crude ketone which was purified with flash chromatography (25% EtOAc/hexane) to yield 207 mg (75%) of the desired product (Compound 19A) and a white solid. MS (electrospray): mass calculated for $C_{23}H_{24}F_3NO_3$, 419.17; m/z found 420.2 $[M+H]^+$.

B. 3-[3-(1-Ethyl-4,4,6-trimethyl-2-oxo-1,2,34-tetrahydro-quinolin-7-yl)-4-trifluoromethoxy-phenyl]-but-2-enoic acid (Compound 19)

This was prepared from Compound 19A using procedure described for Example 1, steps E and F. MS (electrospray): mass calculated for $C_{25}H_{26}F_3NO_4$, 461.18; m/z found 462.2 $[M+H]^+$.

Example 20

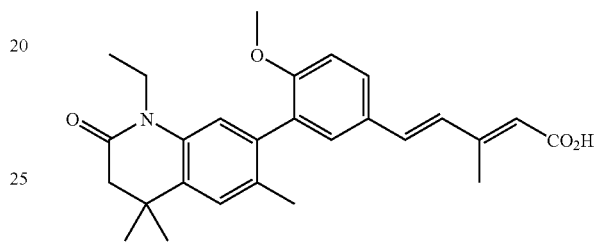

5-[3-(1-Ethyl-4,4,6-trimethyl-2-oxo-1,2,3,4-tetrahydro-quinolin-7-yl)-4-methoxy-phenyl]-3-methyl-penta-2,4-dienoic acid (Compound 20)

A. 3-(1-Ethyl-4,4,6-trimethyl-2-oxo-1,2,3,4-tetrahydro-quinolin-7-yl)-4-methoxy-benzaldehyde (Compound 20A)

Compound 20A was prepared using the procedure described for Example 2, except using 2-methoxy-5-formylphenyl boronic acid as the starting material in step 2A. MS (electrospray): mass calculated for $C_{22}H_{25}NO_3$, 351.18; m/z found 352.2 $[M+H]^+$.

B. 3-[3-(1-Ethyl-4,4,6-trimethyl-2-oxo-1,2,3,4-tetrahydro-quinolin-7-yl)-4-methoxy-phenyl]-acrylic acid ethyl ester (Compound 20B)

This was prepared from Compound 20A using the procedure described for Example 1E, except using triethyl-3-methyl phosphonocrotonate as the starting material. MS (electrospray): mass calculated for $C_{29}H_{35}NO_4$, 461.26; m/z found 462.3 $[M+H]^+$.

C. 3-[3-(1-Ethyl-4,4,6-trimethyl-2-oxo-1,2,3,4-tetrahydro-quinolin-7-yl)-4-methoxy-phenyl]-acrylic acid (Compound 20)

A solution of Compound 20B (30 mg, 0.065 mmol) in 2 mL of THF/water (10:1) was treated with lithium hydroxide (3 mg 0.13 mmol) and heated to 60° C. overnight, cooled, acidified with 5 mL of 1M HCl and extracted with dichloromethane. Removal of solvent yielded 25 mg (89%) of product (Compound 20) as a white solid. MS (electrospray): mass calculated for $C_{27}H_{31}$, $NO_4$, 433.23; m/z found 4342 [M+H]$^+$.

Example 21

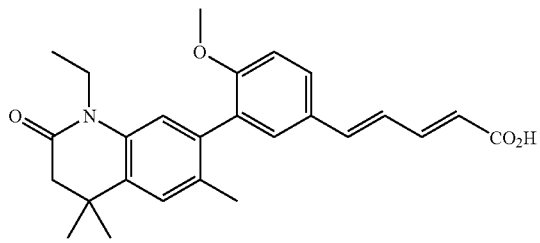

5-[3-(1-Ethyl-4,4,6-trimethyl-2-oxo-1,2,3,4-tetrahydro-quinolin-7-yl)-4-methoxy-phenyl]-penta-2,4-dienoic acid (Compound 21)

Compound 21 was prepared using the procedure described in Example 20, except using triethyl-4-phosphonocrotonate in step 20B. MS (electrospray): mass calculated for $C_{26}H_{29}NO_4$, 419.21; m/z found 420.2 [M+H]$^+$.

Example 22

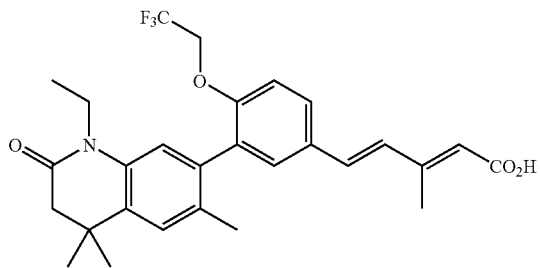

5-[3-(1-Ethyl-4,4,6-trimethyl-2-oxo-1,2,3,4-tetrahydro-quinolin-7-yl)-4-(2,2,2-trifluoro-ethoxy)-phenyl]-3-methyl-penta-2,4-dienoic acid (Compound 22)

Compound 22 was prepared from Compound 1D using procedures similar to those described for Examples 20B and 20C. MS (electrospray): mass calculated for $C_{28}H_{30}F_3NO_4$, 501.21; m/z found 502.2 [M+H]$^+$.

Example 23

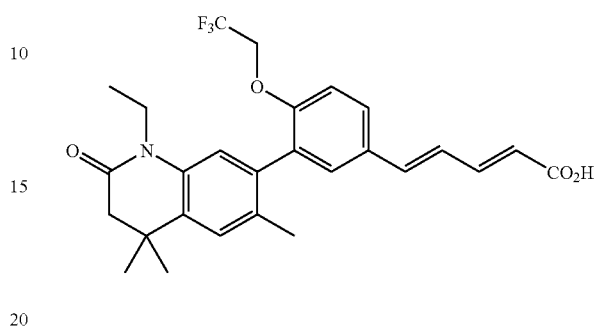

5-[3-(1-Ethyl-4,4,6-trimethyl-2-oxo-1,2,3,4-tetrahydro-quinolin-7-yl)-4-(2,2,2-trifluoro-ethoxy)-phenyl]-penta-2,4-dienoic acid (Compound 23)

Compound 23 was prepared from Compound 1D using procedures similar to those described for Example 20B and 20C, except using triethyl-4-phosphonocrotonate in step 20B. MS (electrospray): mass calculated for $C_{27}H_{28}F_3NO_4$, 487.20; m/z found 488.2 [M+H]$^+$.

Example 24

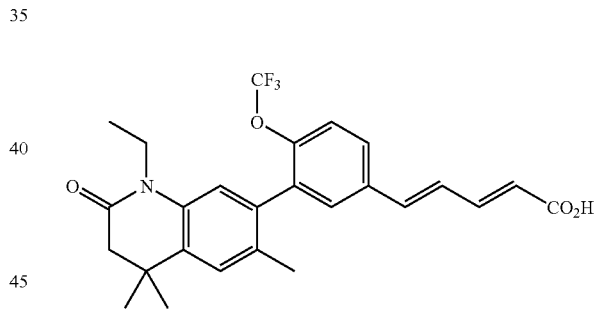

5-[3-(1-Ethyl-4,4,6-trimethyl-2-oxo-1,2,3,4-tetrahydro-quinolin-7-yl)-4-trifluoromethoxy-phenyl]-penta-2,4-dienoic acid (Compound 24)

Compound 24 was prepared from Compound 2A using procedures similar to those described for Example 20B and 20C, except using triethyl-4-phosphonocrotonate in step 20B. MS (electrospray): mass calculated for $C_{26}H_{26}F_3NO_4$, 473.18; m/z found 474.2 $[M+H]^+$.

Example 25

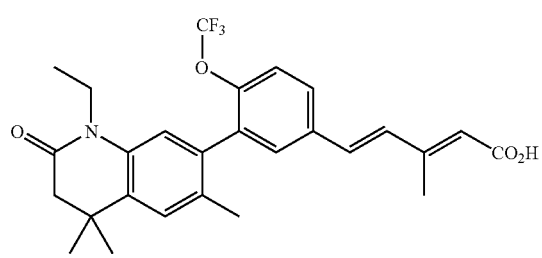

5-[3-(1-Ethyl-4,4,6-trimethyl-2-oxo-1,2,3,4-tetrahydro-quinolin-7-yl)-4-trifluoromethoxy-phenyl]-3-methyl-penta-2,4-dienoic acid (Compound 25)

Compound 25 was prepared from Compound 2A using procedures similar to those described for Example 20B and 20C. MS (electrospray): mass calculated for $C_{27}H_{28}F_3NO_4$, 487.20; m/z found 488.2 $[M+H]^+$.

Example 26

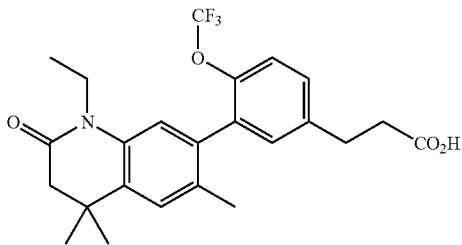

3-[3-(1-Ethyl-4,4,6-trimethyl-2-oxo-1,2,3,4-tetrahydro-quinolin-7-0)-4-trifluoromethoxy-phenyl]-Propionic acid (Compound 26)

Compound 2C was dissolved in EtOAc (use of MeOH produces significant amounts of methyl ester) and hydrogenated with 10% Pd/C and $H_2$ balloon for 4 hours. Pd/C was then filtered off and solvent was evaporated to afford product as colorless oil. Evaporation from hexane or ether afforded product (1.1 g, 100%) as white sticky foam. Product was further dried under high vacuum. MS (electrospray): mass calculated for $C_{24}H_{26}F_3NO_4$, 449.18; m/z found 450.1, $[M+H]^+$. $^1H$ NMR (400 MHz; $CDCl_3$): 1.19 (t, J=8.0 Hz, 3H), 1.31 (s, 6H), 2.09 (s, 3H), 2.52 (s, 2H), 2.72 (t, J=8.0 Hz, 2H), 3.00 (t, J=8.0 Hz, 2H), 3.92 (br s, 1H), 4.08 (br s, 1H), 6.82 (s, 1H), 7.13 (s, 1H), 7.16 (s, 1H), 7.24-7.30 (m, 2H).

Example 27

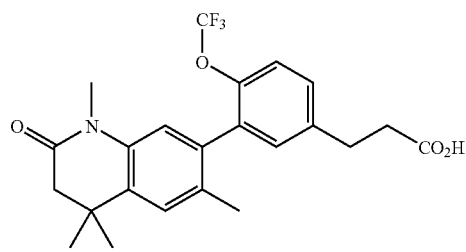

3-[3-(1,4,4,6-Tetramethyl-2-oxo-1,2,3,4-tetrahydro-quinolin-7-yl)-4-trifluoromethoxy-phenyl]-propionic acid (Compound 27)

Compound 27 was prepared from Compound 3 using the procedure described in Example 26. MS (electrospray): mass calculated for $C_{23}H_{24}F_3NO_4$, 435.17; m/z found 436.2 $[M+H]^+$.

Example 28

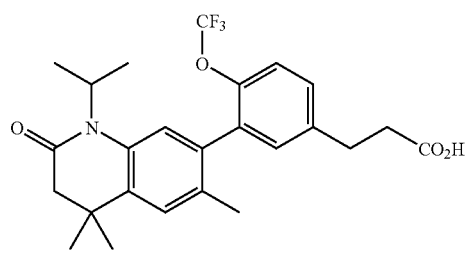

3-[3-(1-Isopropyl-4,4,6-trimethyl-2-oxo-1,2,3,4-tetrahydro-quinolin-7-yl)-4-trifluoromethoxy-phenyl]-propionic acid (Compound 28)

Compound 28 was prepared from Compound 4 using the procedure described in Example 26. MS (electrospray): mass calculated for $C_{25}H_{28}F_3NO_4$, 463.20; m/z found 464.20 $[M+H]^+$.

Example 29

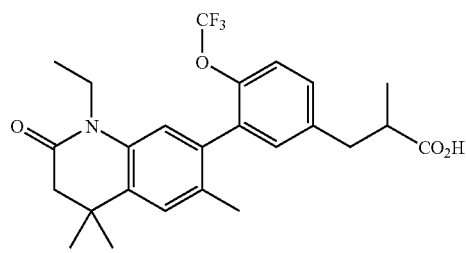

3-[3-(1-Ethyl-4,4,6-trimethyl-2-oxo-1,2,3,4-tetrahydro-quinolin-7-yl)-4-trifluoromethoxy-phenyl]-2-methyl-propionic acid (Compound 29)

Compound 29 was prepared from Compound 9D using the procedure described in Example 26. MS (electrospray): mass calculated for $C_{25}H_{28}F_3NO_4$, 463.20; m/z found 464.2 [M+H]$^+$.

Example 30

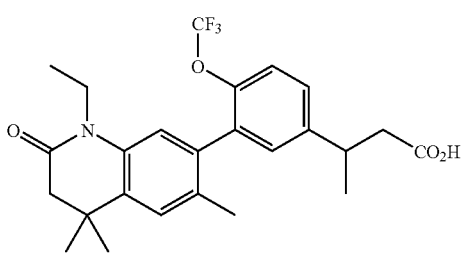

3-[3-(1-Ethyl-4,4,6-trimethyl-2-oxo-1,2,3,4-tetrahydro-quinolin-7-yl)-4-trifluoromethoxy-phenyl]-butyric acid (Compound 30)

Compound 30 was prepared from Compound 19 using the procedure described in Example 26. MS (electrospray): mass calculated for $C_{25}H_{28}F_3NO_4$, 463.20; m/z found 464.2 [M+H]$^+$.

Example 31

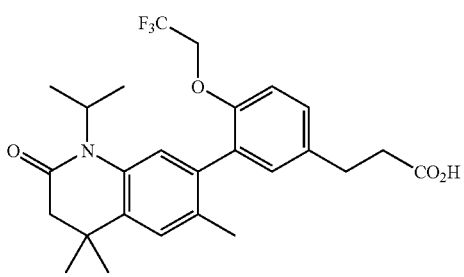

3-[3-(1-Isopropyl-4,4,6-trimethyl-2-oxo-1,2,3,4-tetrahydro-quinolin-7-yl)-4-(2,2,2-trifluoro-ethoxy)-phenyl]-propionic acid (Compound 31)

Compound 31 was prepared from Compound 11 using the procedure described in Example 26. MS (electrospray): mass calculated for $C_{26}H_{30}F_3NO_4$, 477.21; m/z found 478.2 [M+H]$^+$.

Example 32

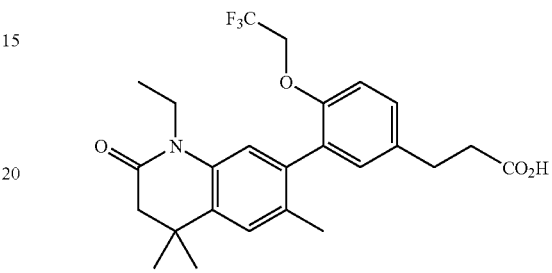

3-[3-(1-Ethyl-4,4,6-trimethyl-2-oxo-1,2,3,4-tetrahydro-quinolin-7-yl)-4-(2,2,2-trifluoro-ethoxy)-phenyl]-propionic acid (Compound 32)

Compound 32 was prepared from Compound 1F using the procedure described in Example 26. MS (electrospray): mass calculated for $C_{24}H_{26}F_3NO_4$, 449.18; m/z found 450.1, [M+H]$^+$. $^1$H NMR (400 MHz; CDCl$_3$): 1.19 (t, J=8.0 Hz, 3H), 1.31 (s, 6H), 2.09 (s, 3H), 2.52 (s, 2H), 2.72 (1, J=8.0 Hz, 2H), 3.00 (t, J=8.0 Hz, 2H), 3.92 (br s, 1H), 4.08 (br s, 1H), 6.82 (s, 1H), 7.13 (s, 1H), 7.16 (s, 1H), 7.24-7.30 (m, 2H).

Example 33

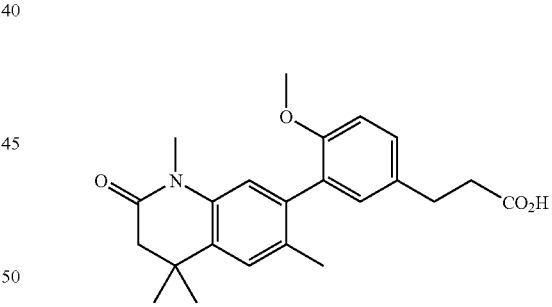

3-[4-Methoxy-3-(1,4,4,6-tetramethyl-2-oxo-1,2,3,4-tetrahydro-quinolin-7-yl)-phenyl]-propionic acid (Compound 33)

To a cooled suspension of 10% Pd—C (20 mg) in 2 mL MeOH, was added a solution of Compound 10 (0.16 mmol, 0.06 g). A balloon filled with H$_2$ gas was placed and the reaction mixture was stirred at r.t. for 3 days. The $^1$H NMR and the mass spectra indicated that the product was mainly 3-[4-methoxy-3-(1,4,4,6-tetramethyl-2-oxo-1,2,3,4-tetrahydro-quinolin-7-yl)-phenyl]-propionic acid methyl ester instead of the desired carboxylic acid product. The methyl ester (0.2 mmol, 0.076 g) was then dissolved in a 4:1:1 mixture of THF-MeOH—H$_2$O and LiOH (0.35 mmol, 0.008 g)

was added. The reaction mixture was allowed to stir overnight. The solvent was removed in vacuo. The milky white residue was dissolved in water and was then acidified with conc. HCl. The white precipitate that was obtained was filtered and washed with cold water to afford the desired product (Compound 33) as a white solid (0.045 g, 59% yield). MS (electrospray): mass calculated for $C_{23}H_{27}NO_4$, 381.19; m/z found 382 $[M+H]^+$.

Example 34

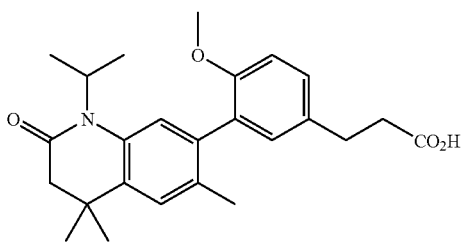

3-[3-(1-Isopropyl-4,4,6-trimethyl-2-oxo-1,2,3,4-tetrahydro-quinolin-7-yl)-4-methoxy-phenyl]-propionic acid (Compound 34)

Compound 34 was prepared from Compound 12 using the procedure described in Example 33. MS (electrospray): mass calculated for $C_{25}H_{29}NO_4$, 407.21; m/z found 408 $[M+H]^+$.

Example 35

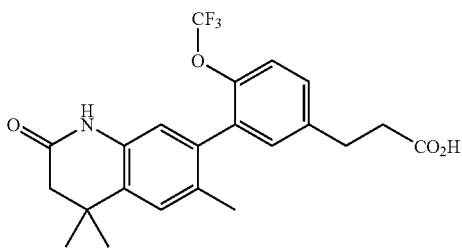

3-[4-Trifluoromethoxy-3-(4,4,6-trimethyl-2-oxo-1,2,3,4-tetrahydro-quinolin-7-yl)-phenyl]-propionic acid (Compound 35)

Compound 35 was prepared from Compound 16D using the procedure described in Example 26. MS (electrospray): mass calculated for $C_{22}H_{22}F_3NO_4$, 421.41; m/z found 422.5, $[M+H]^+$.

Example 36

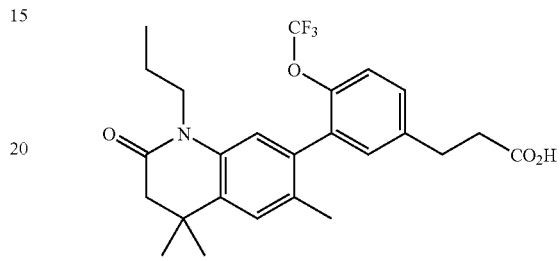

3-[4-Trifluoromethoxy-3-(4,4,6-trimethyl-2-oxo-1-propyl-1,2,3,4-tetrahydro-quinolin-7-1/1)-phenyl]-propionic acid (Compound 36)

Compound 36 was prepared from Compound 15B using the procedure described in Example 26. MS (electrospray): mass calculated for $C_{25}H_{28}F_3NO_4$, 463.20; m/z found 464.2 $[M+H]^+$.

Example 37

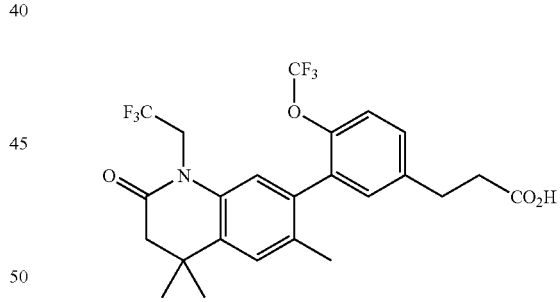

3-{4-Trifluoromethoxy-3-[4,4,6-trimethyl-2-oxo-1-(2,2,2-trifluoro-ethyl)-1,2,3,4-tetrahydro-quinolin-7-yl]-phenyl}-propionic acid (Compound 37)

Compound 37 was prepared from Compound 14B using the procedure described in Example 26. MS (electrospray): mass calculated for $C_{24}H_{23}F_6NO_4$, 503.15; m/z found 504.1 $[M+H]^+$.

Example 38

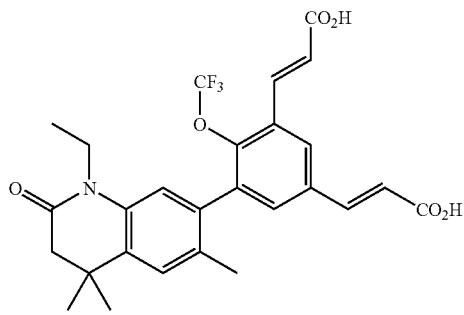

3-[3-(2-Carboxy-vinyl)-5-(1 methyl-2-oxo-1,2,3,4-tetrahydro-quinolin-7-yl)-4-trifluoromethoxy-phenyl]-acrylic acid (Compound 381

Compound 38 was prepared from the dibrominated product obtained from Example 9C using a procedure similar to that described for Example 5C and 5D. MS (electrospray): mass calculated for $C_{27}H_{26}F_3NO_6$, 517.17; m/z found 518.2 $[M+H]^+$.

Example 39

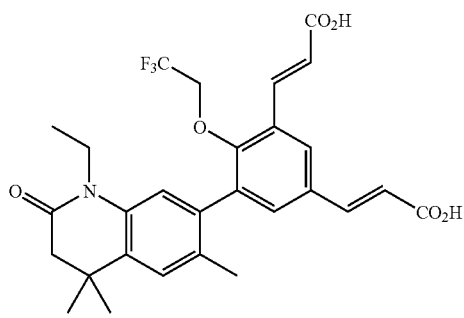

3-[3-(2-Carboxy-vinyl)-5-(1-ethyl-4,4,6-trimethyl-2-oxo-1,2,3,4-tetrahydro-quinolin-7-yl)-4-(2,2,2-trifluoro-ethoxy)-phenyl]-acrylic acid (Compound 39)

A. 1-Ethyl-7-(2-methoxy-phenyl)-4,4,6-trimethyl-3,4-dihydro-1H-quinolin-2-one (Compound 39A)

Compound 39A was prepared from Compound 1A using a procedure similar to that described in Example 1B, except using 2-methoxy phenylboronic acid as the starting material. MS (electrospray): mass calculated for $C_{21}H_{25}NO_2$, 323.19; m/z found 324.2 $[M+H]^+$.

B. 1-Ethyl-7-(2-hydroxy-phenyl)-4,4,6-trimethyl-3,4-dihydro-1H-quinolin-2-one (Compound 39B)

This was prepared from Compound 39A, using the procedure described for Example 1C. MS (electrospray): mass calculated for $C_{20}H_{23}NO_2$, 309.17; m/z found 310.2 $[M+H]^+$.

C. 7-(3,5-Dibromo-2-hydroxy-phenyl)-1-ethyl-4,4,6-trimethyl-3,4-dihydro-1H-quinolin-2-one (Compound 39C)

A solution of Compound 39B (200 mg, 0.65 mmol) in 3 mL of chloroform with 0.1 mL of methanol, was treated with 126 mg of NBS (0.72 mmol) overnight at room temperature, after which a saturated solution of sodium thiosulfate (15 mL) was used to quench the reaction. The reaction was then extracted with chloroform (2×50 mL), the combined organic layers were dried with sodium sulfate, filtered and stripped to afford a crude mixture of mono and di-brominated product which was purified using flash chromatography (5% EtOAc/hexanes) to afford 174 mg (58%) dibromo product and 125 mg (42%) mono brominated product (Compound 39C). MS (electrospray): mass calculated for $C_{20}H_{21}Br_2NO_2$, 464.99; m/z found 466 $[M+H]^+$.

D. 3-[3-(2-Carboxy-vinyl)-5-(1-ethyl-4,4,6-trimethyl-2-oxo-1,2,3,4-tetrahydro-quinolin-7-yl)-4-(2,2,2-trifluoro-ethoxy)-phenyl]-acrylic acid (Compound 39)

Compound 39 was prepared from Compound 39C, using the procedures described for Examples 5C and 5D. MS (electrospray): mass calculated for $C_{28}H_{28}F_3NO_6$, 531.19; m/z found 532.2 $[M+H]^+$.

Example 40

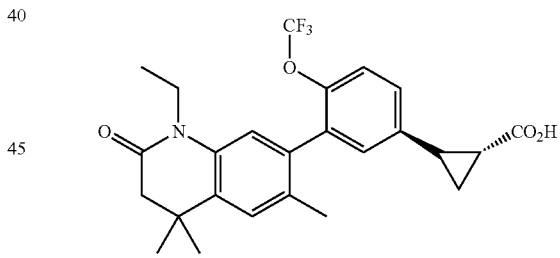

(□)-2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid (Compound 40)

A. 2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid tert-butyl ester (Compound 40A)

To a round bottom flask was added trimethylsulfoxonium iodide (2.8 mmol, 0.37 g) and 60% NaH (2.8 mmol, 0.07 g) and the flask was cooled to −10° C. with an ice-water bath. DMSO 92 ML) was then added dropwise. Initially some foamy suspension was observed. The cooling bath was removed and the reaction mixture was allowed to stir at r.t. for 30-40 min till the reaction mixture became a turbid solution.

Compound 2B (0.17 mmol, 0.085 g) was then dissolved in 1.5 mL DMSO and was added to the reaction mixture. The golden yellow solution was stirred at 50° C. (oil bath) for 2 h. After cooling to r.t., the reaction mixture was poured into 50 mL of ice-water. It was extracted with EtOAc (3×15 mL). The organic layer was washed with water followed by brine and was then dried over $Na_2SO_4$. The solvent was filtered and evaporated in vacuo to obtain 2-[3-(1-ethyl-4,4,6-trimethyl-2-oxo-1,2,3,4-tetrahydro-quinolin-7-yl)-4-trifluoromethoxy-phenyl]-cyclopropanecarboxylic acid tert-butyl ester as a colorless oil. It was purified by preparative TLC with 3.5:1 hexanes-EtOAc as the eluting system to obtain 0.04 g of the product as a white foam. The product has the same Rf as the starting material. However, the product does not stain with $KMnO_4$ stain indicating the disappearance of the double bond while the starting material does.

B. 2-(3-(1-Ethyl-4,4,6-trimethyl-2-oxo-1,2,3,4-tetrahydro-quinolin-7-yl)-4-trifluoromethoxy-phenyl)-cyclopropanecarboxylic acid (Compound 40)

A solution of Compound 40A in $CH_2Cl_2$ (2 mL) and TFA (1 mL) was stirred at r.t. overnight afterwhich the solvent was removed in vacuo to obtain the desired product (Compound 40) as pale yellow powder (0.036 g). The compound is racemic (i.e. mixture of both enantiomers). The designated "trans" stereochemistry merely describes the relative stereochemistry for the two substituents on the cyclopropane ring. MS (electrospray): mass calculated for $C_{25}H_{26}F_3NO_4$, 461.18; m/z found 462 $[M+H]^+$.

Example 41

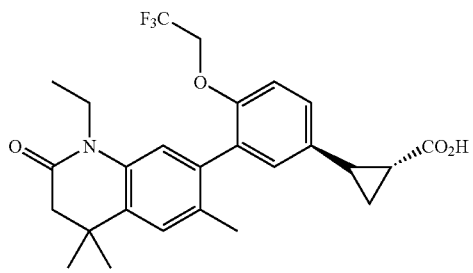

(□)-2-[3-(1-Ethyl-4,4,6-trimethyl-2-oxo-1,2,3,4-tetrahydro-quinolin-7-yl)-4-(2,2,2-trifluoro-ethoxy)-phenyl]-cyclopropanecarboxylic acid (Compound 41)

Compound 41 was prepared from Compound 1E using the procedure described in Example 40. The compound is racemic (i.e. mixture of both enantiomers). The designated "trans" stereochemistry merely describes the relative stereochemistry for the two substituents on the cyclopropane ring. MS (electrospray): mass calculated for $C_{26}H_{28}F_3NO_4$, 475.2; m/z found 476 $[M+H]^+$.

Example 42

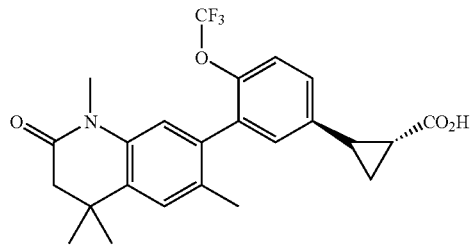

(□)-2-[3-(1,4,4,6-Tetramethyl-2-oxo-1,2,3,4-tetrahydro-quinolin-7-yl)-4-trifluoromethoxy-phenyl]-cyclopropanecarboxylic acid (Compound 42)

Compound 42 was prepared from Compound 3 using the procedure described in Example 40. The compound is racemic (i.e. mixture of both enantiomers). The designated "trans" stereochemistry merely describes the relative stereochemistry for the two substituents on the cyclopropane ring, MS (electrospray): mass calculated for $C_{24}H_{24}F_3NO_4$, 447.17; m/z found 448 $[M+H]^+$.

Example 43

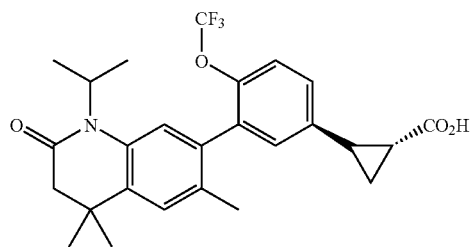

(□)-2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid (Compound 43)

Compound 43 was prepared from Compound 4 using the procedure described in Example 40. The compound is racemic (i.e. mixture of both enantiomers). The designated "trans" stereochemistry merely describes the relative stereochemistry for the two substituents on the cyclopropane ring.

MS (electrospray): mass calculated for $C_{26}H_{28}F_3NO_4$, 475.20; m/z found 476 $[M+H]^+$.

Example 44

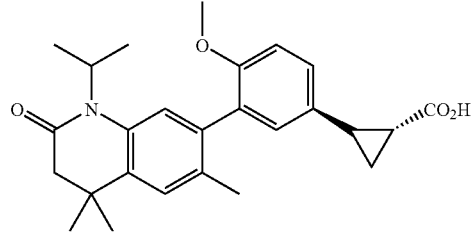

(□)-2-[3-(1-Isopropyl-4,4,6-trimethyl-2-oxo-1,2,3,4-tetrahydro-Quinolin-7-O-4-methoxy-phenyl]-cyclopropanecarboxylic acid (Compound 44)

Compound 44 was prepared from Compound 11 using the procedure described in Example 40. The compound is racemic (i.e. mixture of both enantiomers). The designated "trans" stereochemistry merely describes the relative stereochemistry for the two substituents on the cyclopropane ring. MS (electrospray): mass calculated for $C_{26}H_{31}NO_4$, 421.23; m/z found 422 $[M+H]^+$.

Example 45

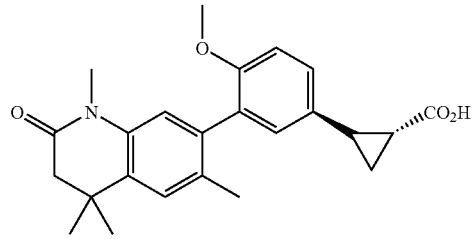

(□)-2-[4-Methoxy-3-(1,4,4,6-tetramethyl-2-oxo-1,2,3,4-tetrahydro-quinolin-7-yl-phenyl]-cyclopropanecarboxylic acid (Compound 45)

Compound 45 was prepared from Compound 10 using the procedure described in Example 40. The compound is racemic (i.e. mixture of both enantiomers). The designated "trans" stereochemistry merely describes the relative stereochemistry for the two substituents on the cyclopropane ring. MS (electrospray): mass calculated for $C_{25}H_{29}NO_4$, 407.20; m/z found 408 $[M+H]^+$.

Scheme 13: Separation of Enantiomers 46 and 47

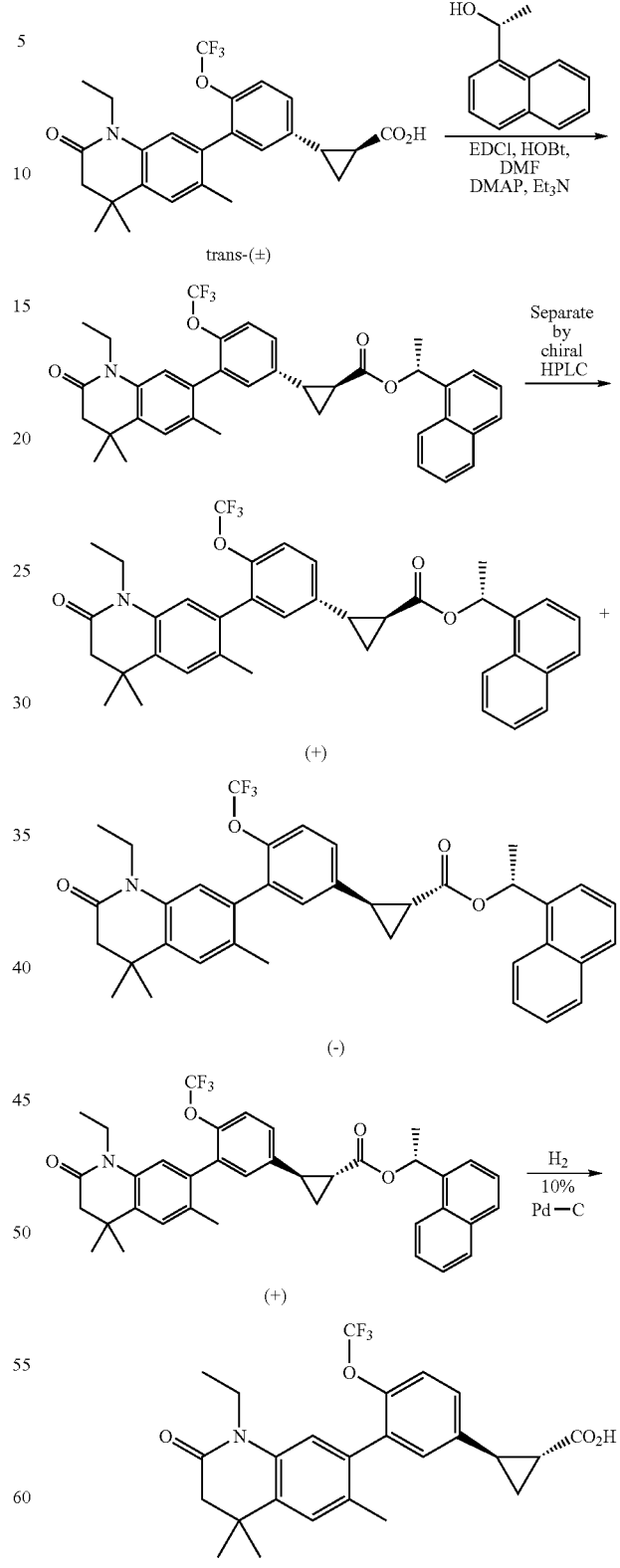

-continued

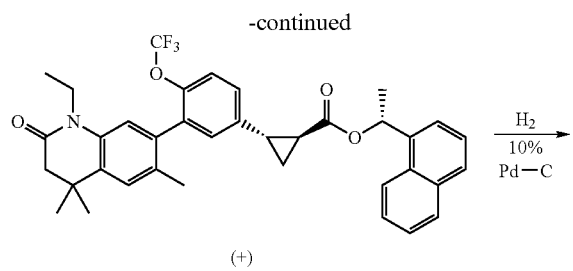

(+)

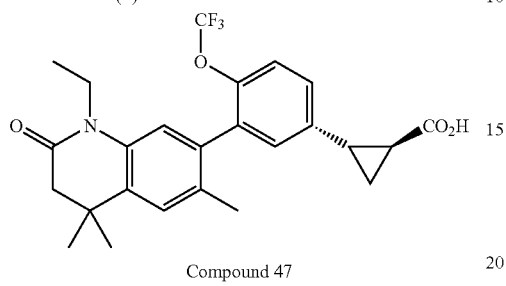

Compound 47

Example 46

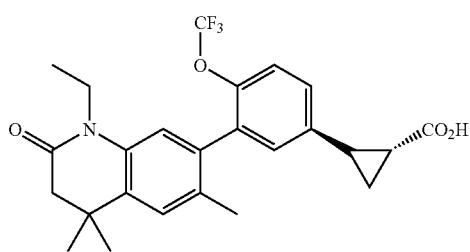

(−)-2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid (Compound 46)

In accordance with Scheme 10, to a solution of Compound 40B (0.1 mmol, 0.046 g), (R)-(+)-methyl-2-naphthalene methanol (0.15 mmol, 0.026 g), HOBt (0.1 mmol, 0.014 g), EDCI (0.15 mmol, 0.03 g) and DMAP (2 crystals) in DMF (1 mL) was added Et₃N (0.04 mL) at r.t. for 12 h. The reaction mixture was extracted with EtOAc and the organic layer was washed with water, sat. NH₄Cl solution followed by brine. The organic layer was separated, dried over Na₂SO₄ and filtered through a sintered glass funnel. The solvent was removed in vacuo. The crude residue was purified by preparative TLC with 6:1 hexanes-EtOAc as the eluting system to obtain 0.025 g of the mixture of diastereomers as a white foam. The diastereomers were separated by using a Varian Prep Star 218 HPLC instrument with Chiralpak-AD (21.2× 250 mL) column as the stationary phase and 80% n-hexane-20% EtOH with 0.05% TFA as the eluent. With the flow rate of 5 mL/min, injection volume of 0.5 mL, the retention times (detector at 254 nm) for the two diastereomers were 18.3 min and 21.4 min respectively. In Scheme 13 the designated "trans" stereochemistry merely describes the relative stereochemistry for the two substituents on the cyclopropane ring. The first isomer (70 mg) was dissolved in 8 mL EtOAc and was added to a suspension of 10% Pd—C (15 mg) in 2 mL EtOAc. Hydrogen gas was introduced via a balloon and the reaction mixture was stirred overnight and then filtered through a pad of celite. Some starting material was observed by ¹H NMR. The residue was purified by preparative TLC (15:1 CH₂Cl₂-MeOH) to obtain 2-[3-(1-ethyl-4,4,6-trimethyl-2-oxo-1,2,3,4-tetrahydro-quinolin-7-yl)-4-trifluoromethoxy-phenyl]-cyclopropanecarboxylic acid as a white solid (0.02 g). The absolute stereochemistry at the chiral centers was not determined. MS (electrospray): mass calculated for $C_{25}H_{26}F_3NO_4$, 461.18; m/z found 462 [M+H]⁺. $[\alpha]_D = -119.5$, (c=0.009, CHCl₃)

Example 47

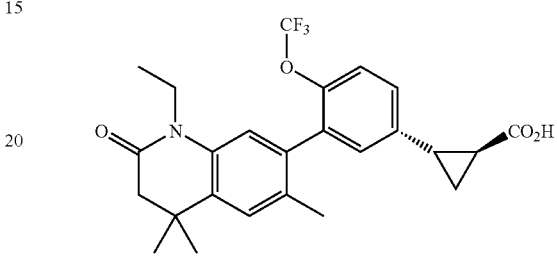

(+)-2-[3-(1-Ethyl-4,4,6-trimethyl-2-oxo-1,2,3,4-tetrahydro-quinolin-7-yl)-4-trifluoromethoxy-phenyl]-cyclopropanecarboxylic acid (Compound 47)

The second isomer (66 mg) was dissolved in 8 mL EtOAc and was added to a suspension of 10% Pd—C (15 mg) in 2 mL EtOAc. Hydrogen gas was introduced via a balloon and the reaction mixture was stirred overnight and then filtered through a pad of celite. Some starting material was observed by ¹H NMR. The residue was purified by preparative TLC (15:1 CH₂Cl₂-MeOH) to obtain 2-[3-(1-ethyl-4,4,6-trimethyl-2-oxo-1,2,3,4-tetrahydro-quinolin-7-yl)-4-trifluoromethoxy-phenyl]-cyclopropanecarboxylic acid as a white solid (0.02 g). The absolute stereochemistry at the chiral centers was not determined. MS (electrospray): mass calculated for $C_{25}H_{26}F_3NO_4$, 461.18; m/z found 462 [M+H]⁺. $[\alpha]_D = +96.4$ (c=0.01, CHCl₃)

Scheme 14: Separation of Enantiomers 48 and 49

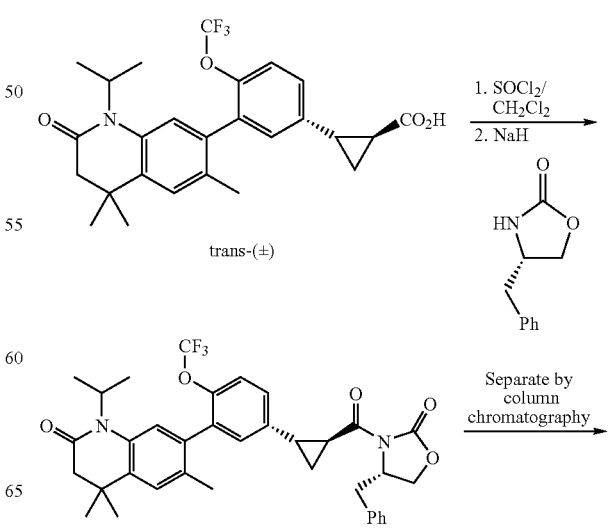

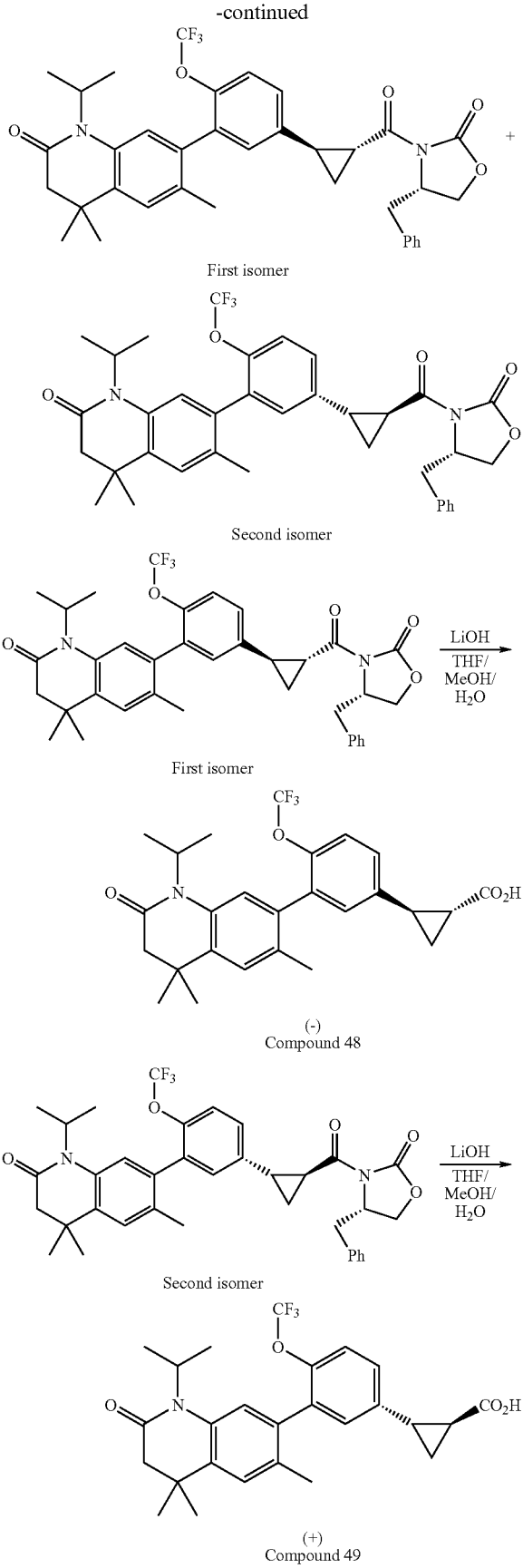

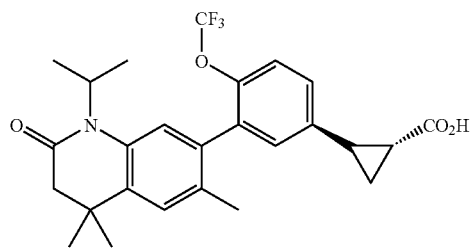

Example 48

(+)-2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid (Compound 48)

In accordance with Scheme 14, to a solution of racemic Compound 43 (0.5 mmol, 0.23 g) in 10 mL CH$_2$Cl$_2$ was added thionyl chloride (9.4 mmol, 0.68 mL) and the solution was stirred at r.t. overnight. The solvent was removed in vacuo to obtain 2-[3-(1-isopropyl-4,4,6-trimethyl-2-oxo-1,2,3,4-tetrahydro-quinolin-7-yl)-4-trifluoromethoxy-phenyl]-cyclopropanecarbonyl chloride as a yellow thick oil. It was used in the next step without purification.

To a solution of (S)-(−)-4-benzyl-2-oxazolidinone (0.6 mmol, 0.11 g) in 3 mL THF was added 60% NaH (0.72 mmol, 0.03 g) in one portion at r.t. The white suspension was stirred at r.t. for 30 min and was then cooled to −78° C. with a dry ice bath. A solution of 2-[3-(1-isopropyl-4,4,6-trimethyl-2-oxo-1,2,3,4-tetrahydro-quinolin-7-yl)-4-trifluoromethoxy-phenyl]-cyclopropanecarbonyl chloride (0.5 mmol) in 5 mL THF was then added and the reaction mixture was stirred at −78° C. for 15 min followed by stirring at r.t. for 1 h. The clear solution was quenched with a few drops of H$_2$O. The solvent was removed in vacuo and the residue was purified by column chromatography with a gradient of 3:1 hexane/EtOAc to 3:2 hexane/EtOAc. The solvent was removed and the product was then purified by preparative TLC with 3:1 hexanes/EtOAc as the eluting system. In Scheme 14 the designated "trans" stereochemistry merely describes the relative stereochemistry for the two substituents on the cyclopropane ring.

The first isomer of 7-{5-[2-(4-benzyl-2-oxo-oxazolidine-3-carbonyl)-cyclopropyl]-2-trifluoromethoxy-phenyl}-1-isopropyl-4,4,6-trimethyl-3,4-dihydro-1H-quinolin-2-one that eluted has a Rf=0.45 (0.08 g) and the second isomer eluted with Rf=0.41 (0.06 g). The chiral auxilary was removed by hydrolysis of each isomer with LiOH (0.25 mmol, 0.006 g) in 4:1:1 mixture of THF/MeOH/H$_2$O. Each carboxylic acid was further purified by preparative TLC (15:1 CH$_2$Cl$_2$/MeOH). The first isomer from the column yielded 6 mg of 2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid. The absolute stereochemistry at the chiral centers was not determined. MS (electrospray): mass calculated for $C_{26}H_{28}F_3NO_4$, 475.20; m/z found 476 [M+H]$^+$ [□]$_D$=+102.7 (c=0.5, CHCl$_3$)

Example 49

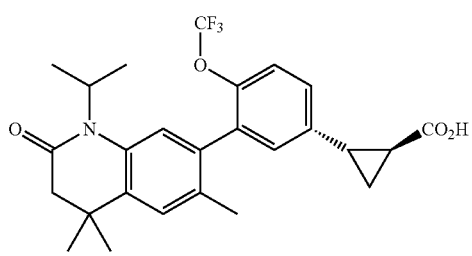

(−)-2-[3-(1-Isopropyl-4,4,6-trimethyl-2-oxo-1,2,3,4-tetrahydro-quinolin-7-yl)-4-trifluoromethoxy-phenyl]-cyclopropanecarboxylic acid (Compound 49)

The second isomer from the column yielded 7.2 mg of 2-[3-(1-isopropyl-4,4,6-trimethyl-2-oxo-1,2,3,4-tetrahydro-quinolin-7-yl)-4-trifluoromethoxy-phenyl]-cyclopropanecarboxylic acid. The absolute stereochemistry at the chiral centers was not determined. MS (electrospray): mass calculated for $C_{26}H_{28}F_3NO_4$, 475.20; m/z found 476 [M+H]$^+$. [□]$_D$=−79.9, (c=0.5, CHCl$_3$).

Example 50

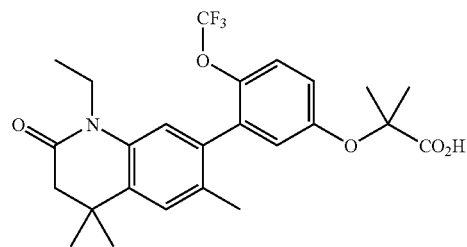

2-[3-(1-Ethyl-4,4,6-trimethyl-2-oxo-1,2,3,4-tetrahydro-quinolin-7-yl)-4-trifluoromethoxy-phenoxy]-2-methyl-propionic acid (Compound 50)

A. 7-Bromo-1-ethyl-4,4,6-trimethyl-3,4-dihydro-1H-quinolin-2-one (Compound 50A)

Compound 50A was synthesized by the procedure described in WO 03/075924.

B. 1-Ethyl-4,4,6-trimethyl-7-(4,4,5,5-tetramethyl-[1,3,2]dioxaborolan-2-O-3,4-dihydro-1H-quinolin-2-one (Compound 50B)

To a solution of Compound 50A (2.0 g, 1.0 eq.), palladium acetate (76 mg, 0.05 eq.) and 2-(dicyclohexylphosphino)biphenyl (474 mg, 0.2 eq.) in 20 mL of anhydrous dioxane was added triethyl amine (3.8 mL, 4 eq.) followed by pinacolborane (3.0 mL, 3 eq.). The reaction mixture was heated to 85° C. for 4 hours. After cooling, reaction was quenched with water dropwise and partitioned between ethyl acetate and ammonium chloride. The aqueous layer was further extracted (1×50 mL) with ethyl acetate and the combined organic layers were dried over sodium sulfate, filtered and adsorbed on silica. Purification by flash chromatography (90:10, 80:20 hexanes/EtOAc) afforded 1.4 g (60%) of product (Compound 50B) as yellow oil. MS (electrospray): mass calculated for $C_{20}H_{30}BNO_3$, 343.27; m/z found 344.1, [M+H]$^+$.

C. 1-Ethyl-7-(5-hydroxy-2-trifluoromethoxy-phenyl)-4,4,6-trimethyl-3,4-dihydro-1H-quinolin-2-one (Compound 50C)

This was prepared from Compound 50B and acetic acid 3-bromo-4-trifluoromethoxy-phenyl ester using a procedure similar to that used for Example 1B. Purification by flash chromatography (80:20, 70:30 hexanes/EtOAc) afforded 294 mg (54%) of product (Compound 50C) as colorless oil. MS (electrospray): mass calculated for $C_{21}H_{22}F_3NO_3$, 393.40; m/z found 393.2, [M]$^+$.

D. 2-[3-(1-Ethyl-4,4,6-trimethyl-2-oxo-1,2,3,4-tetrahydro-quinolin-7-yl)-4-trifluoromethoxy-phenoxy]-2-methyl-propionic acid (Compound 50)

To a solution of Compound 50C (93 mg, 1.0 eq.) and ethyl 2-bromoisobutyrate (0.18 ml, 5.0 eq.) in 3 mL of anhydrous acetonitrile was added cesium carbonate (231 mg, 3.0 eq.). The reaction mixture was heated to 80° C. overnight. After cooling, reaction was partitioned between $CH_2Cl_2$ and ammonium chloride. The aqueous layer was further extracted (1×20 mL) with $CH_2Cl_2$ and the combined organic layers were dried over sodium sulfate and solvent was evaporated. Purification by flash chromatography (70:30 hexanes/EtOAc) afforded 66 mg of ethyl ester as colorless oil. Oil was dissolved in 2 mL of THF, 4 mL of MeOH and 2 mL of 3 M NaOH and stirred overnight. Reaction was acidified with 3 M HCl and product was extracted with $CH_2Cl_2$. Organics were evaporated to afford 45 mg (40%) of product Compound 50 as white solid. MS (electrospray): mass calculated for $C_{25}H_{28}F_3NO_5$, 479.49; m/z found 480.6, [M+H]$^+$.

Example 51

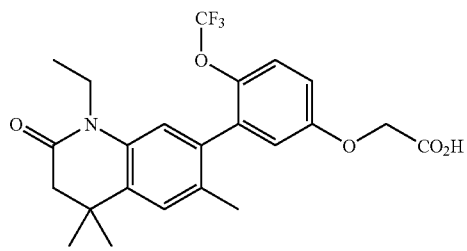

[3-(1-Ethyl-4,4,6-trimethyl-2-oxo-1,2,3,4-tetrahydro-quinolin-7-yl)-4-trifluoromethoxy-phenoxy]-acetic acid (Compound 51)

Compound 51 was prepared using a procedure similar to that used for Example 50, except using ethyl bromoacetate as Example 52

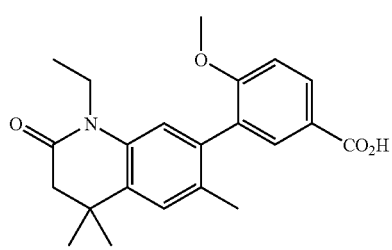

3-(1-Ethyl-4,4,6-trimethyl-2-oxo-1,2,3,4-tetrahydro-quinolin-7-yl)-4-methoxy-benzoic acid (Compound 52)

A. 3-(1-Ethyl-4,4,6-trimethyl-2-oxo-1,2,3,4-tetrahydro-quinolin-7-yl)-4-methoxy-benzoic acid methyl ester (Compound 52A)

Compound 52A was prepared from Compound 5A using a procedure similar to the one described for Example 5B, except 3-bromo-4-methoxy-methyl benzoate was used a starting material. MS (electrospray): mass calculated for $C_{23}H_{27}NO_4$, 381.19; m/z found 382.2 $[M+H]^+$.

B. 3-(1-Ethyl-4,4,6-trimethyl-2-oxo-1,2,3,4-tetrahydro-quinolin-7-yl)-4-methoxy-benzoic acid (Compound 52)

Compound 52 was prepared from Compound 52A using the procedure described for Example 20C. MS (electrospray): mass calculated for $C_{22}H_{25}NO_4$, 367.18; m/z found 368.2 $[M+H]^+$.

Scheme 15: Synthesis of Intermediates for Compounds 53 & 54

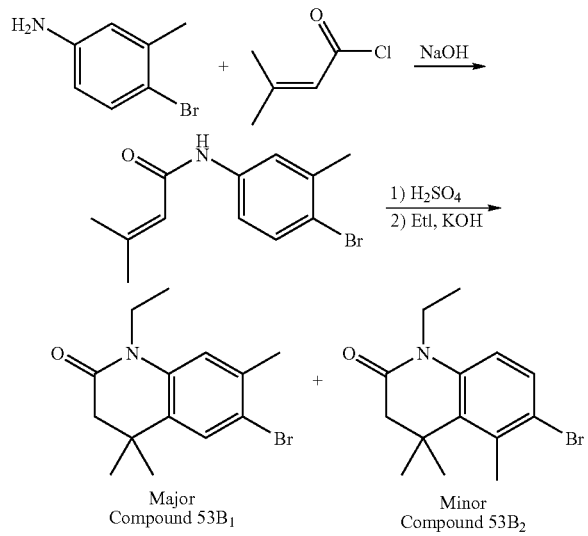

Example 53

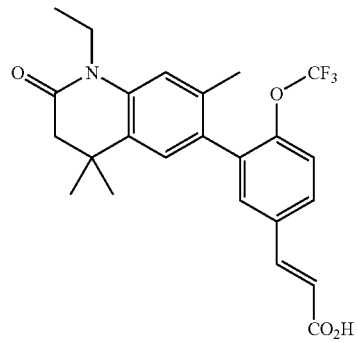

3-[3-(1-Ethyl-4,4,7-trimethyl-2-oxo-1,2,3,4-tetrahydro-quinolin-6-yl)-4-trifluoromethoxy-phenyl]-acrylic acid (Compound 53)

A. 3-Methyl-but-2-enoic acid (4-bromo-3-methyl-phenyl)-amide (Compound 53A)

In accordance with Scheme 15, to the solution of 4-bromo-3-methyl-phenylamine (2 g, 1 eq.) in 5 mL of $CH_2Cl_2$ was added 10 mL of 2 M NaOH followed by dropwise addition of 3,3-dimethylacryloyl chloride (1.32 mL, 1.1 eq.) in 5 mL of $CH_2Cl_2$. The reaction was allowed to stir overnight and then partitioned between EtOAc and brine. The organic layer was separated, dried over $Na_2SO_4$, filtered and the solvent was removed in vacuo to afford 2.84 g (98.6%) of product Compound 53A as beige solid. Crude product was used for the next step.

B. 6-Bromo-1-ethyl-4,4,7-trimethyl-3,4-dihydro-1H-quinolin-2-one (Compound 53B)

Compound 53A (2.84 g) in 15 mL of conc. $H_2SO_4$ was heated to 90° C. for 2 hours. Reaction was then poured onto 200 mL of ice/water mixture, stirred for 30 min and white precipitate was collected by vacuum filtration. Crude mixture of isomers was used in the next step.

Solution of mixture of isomers (1.3 g, 1 eq.) and ethyl iodide (2.0 mL, 5 eq.) in 10 mL of anhydrous DMSO was cooled on ice and crushed into powder KOH (0.54 g, 2.0 eq.) was added slowly. Reaction was stirred on ice for 1 hour and at rt for another hour. Reaction was then partitioned between $CH_2Cl_2$ and water. The organic layer was separated, dried over $Na_2SO_4$, filtered and the solvent was removed in vacuo. The mixture of isomers (Compound 53B) was purified by column chromatography (90:10 hexane/EtOAc) to obtain 0.55 g of pure 6-bromo-1-ethyl-4,4,7-trimethyl-3,4-dihydro-1H-quinolin-2-one (Compound $53B_1$) as the major isomer (eluting first) and 0.21 g of pure 6-bromo-1-ethyl-4,4,5-trimethyl-3,4-dihydro-1H-quinolin-2-one (Compound $53B_2$) as the minor isomer. Overlapping fractions were not separated.

MS (electrospray): mass calculated for $C_{14}H_{18}BrNO$, 295.06; m/z found 296.2, $[M+H]^+$.

C. 3-[3-(1-Ethyl-4,4,7-trimethyl-2-oxo-1,2,3,4-tetrahydro-quinolin-6-yl)-4-trifluoromethoxy-phenyl]-acrylic acid (Compound 53)

Compound 53 was made from Compound 53B$_1$ using a procedure similar to that described in Example 2. MS (electrospray): mass calculated for $C_{24}H_{24}F_3NO_4$, 447.17; m/z found 448.3, $[M+H]^+$.

Example 54

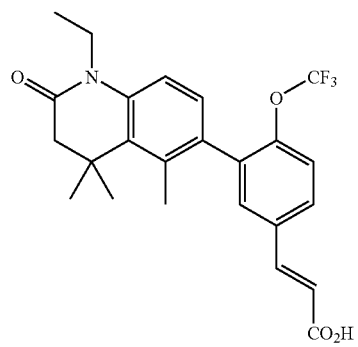

3-[3-(1-Ethyl-4,4,5-trimethyl-2-oxo-1,2,3,4-tetrahydro-quinolin-6-yl)-4-trifluoromethoxy-phenyl]-acrylic acid (Compound 54)

This was made from Compound 53B$_2$ using a procedure similar to that described in Example 2. MS (electrospray): mass calculated for $C_{24}H_{24}F_3NO_4$, 447.17; m/z found 448.3, $[M+H]^+$.

Example 55

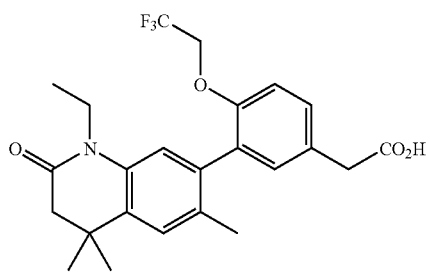

[3-(1-Ethyl-4,4,6-trimethyl-2-oxo-1,2,3,4-tetrahydro-quinolin-7-yl)-4-(2,2,2-trifluoro-ethoxy)-phenyl]-acetic acid (Compound 55)

Scheme 16: Synthesis of Compound 55

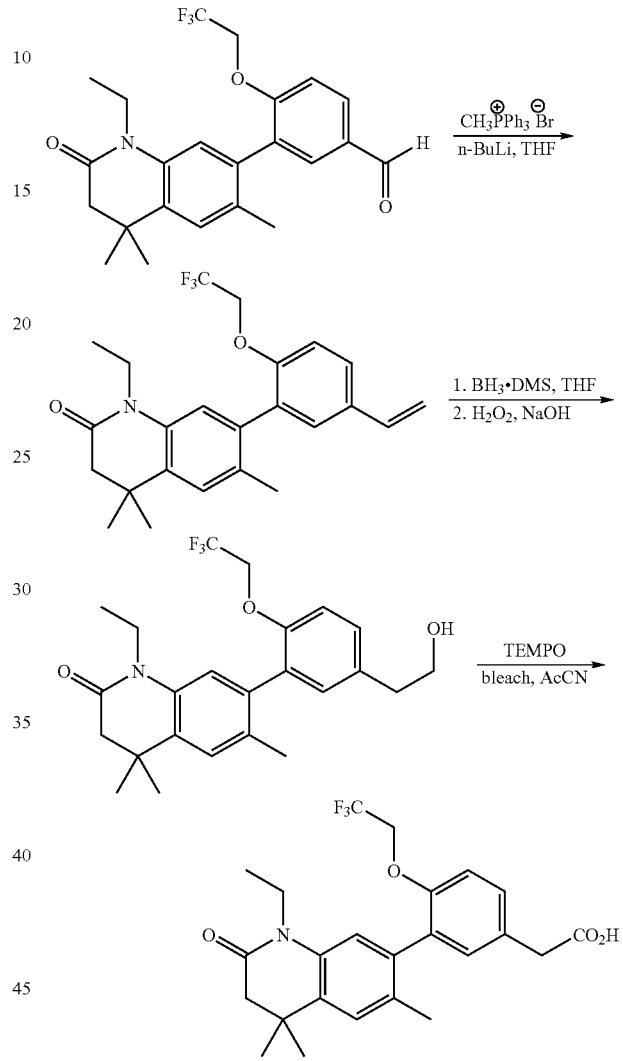

A. 1-Ethyl-4,4,6-trimethyl-7-[2-(2,2,2-trifluoro-ethoxy)-5-vinyl-phenyl]-3,4-dihydro-1H-quinolin-2-one (Compound 55A)

In accordance with Scheme 16, to a suspension of methyltriphenylphosphonium bromide (3.27 mmol, 1.17 g) in 7.5 mL THF was added a solution of n-butyllithium in hexanes (1.6 M, 3.27 mmol, 2.04 mL) at −40° C. The reaction was warmed to −10° C. and stirred for 30 min. The reaction mixture was cooled to −60° C. and then Compound 10 (0.14 mmol, 0.06 g), in THF, was added dropwise. The yellow suspension was allowed to stir at r.t. overnight and then quenched by adding 1 mL H$_2$O. It was extracted with EtOAc and was washed with brine. The organic layer was separated, dried over Na$_2$SO$_4$, filtered and the solvent was removed in vacuo. The yellow oil thus obtained was then purified by column chromatography (3.5:1 hexanes/EtOAc) to obtain 1-ethyl-4,4,6-trimethyl-7-[2-(2,2,2-trifluoro-ethoxy)-5-vinyl-phenyl]-3,4-dihydro-1H-quinolin-2-one as a colorless thick gum (0.61 g, 94% yield).

B. 1-ethyl-7-[5-hydroxymethyl-2-(2,2,2-trifluoro-ethoxy)-phenyl]-4,4,6-trimethyl-3,4-dihydro-1H-quinolin-2-one (Compound 55B)

To a solution of Compound 55A (0.24 mmol, 0.1 g) in 2 mL THF was added a solution of borane dimethylsulfide in THF (0.36 mmol, 0.03 mL) at 0° C. and the reaction mixture was stirred overnight. A solution of 2M NaOH (1 mL) was then added followed by a dropwise addition of hydrogen peroxide (30%, 1 mL). The solution was stirred at r.t. for 3 h. It was extracted with EtOAc, washed with water and brine, dried over $Na_2SO_4$, filtered and concentrated. The LCMS indicated the presence of the desired product (m/z found 436) and a byproduct where the amide carbonyl group was reduced to a methylene group (m/z found 422). The residue was purified by column chromatography (3:1 hexane/EtOAc followed by 1:1 hexane/EtOAc) to obtain 1-ethyl-7-[5-hydroxymethyl-2-(2,2,2-trifluoro-ethoxy)-phenyl]-4,4,6-trimethyl-3,4-dihydro-1H-quinolin-2-one as a colorless oil (0.073 g).

C. [3-(1-Ethyl-4,4,6-trimethyl-2-oxo-1,2,3,4-tetrahydro-quinolin-7-yl)-4-(2,2,2-trifluoro-ethoxy)-phenyl]-acetic acid (Compound 55)

To a solution of 1-ethyl-7-[5-hydroxymethyl-2-(2,2,2-trifluoro-ethoxy)-phenyl]-4,4,6-trimethyl-3,4-dihydro-1H-quinolin-2-one (Compound 55B, 0.14 mmol, 0.06 g) in 1 mL acetonitrile was added TEMPO (0.01 mmol, 1.5 mg)) and sodium chlorite in $H_2O$. Phosphate buffer was then added and the reaction mixture was heated to 35° C. in an oil bath. A dilute solution of commercial bleach (1 mL in 20 mL $H_2O$) was added. The color of the reaction changed from colorless to golden brown. The reaction mixture was stirred at 35° C. for 4 h and then at r.t. overnight. The reaction was quenched with a solution of sodium thiosulfate. Extracted with EtOAc, washed with $H_2O$, brine, dried over $Na_2SO_4$, filtered and concentrated. The residue was dissolved in dilute NaOH and was extracted with $Et_2O$. The aquous layer was acidified with conc. HCl and was extracted with EtOAc. The organic layer was dried over $MgSO_4$, filtered and was the solvent was removed in vacuo. Compound 55, [3-(1-Ethyl-4,4,6-trimethyl-2-oxo-1,2,3,4-tetrahydro-quinolin-7-yl)-4-(2,2,2-trifluoro-ethoxy)-phenyl]-acetic acid, was obtained as a white solid (0.046 g). MS (electrospray): mass calculated for $C_{26}H_{28}F_3NO_4$, 449.18; m/z found 450 $[M+H]^+$. $^1$HNMR (400 MHz, $CDCl_3$): 7.23 (dd, J=2.01, 8.5 Hz, 1H), 7.07 (d, J=2.5 Hz, 2H), 6.89 (d, J=8.5 Hz, 1H), 6.78 (s, 1H), 4.16 (q, J=8.0 Hz, 2H), 3.92 (br, 2H), 3.59 (s, 2H), 2.45 (s, 2H), 2.02 (s, 3H), 1.24 (s, 6H), 1.12 (t, J=7.07 Hz, 3H).

Example 56

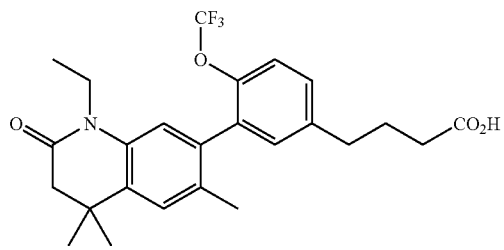

4-(3-(1-Ethyl-4,4,6-trimethyl-2-oxo-1,2,3,4-tetrahydro-quinolin-7-yl)-4-trifluoromethoxy-phenyl)-butyric acid (Compound 56)

A. 1-Ethyl-7-[5-(4-hydroxy-but-1-ynyl)-2-trifluoromethoxy-phenyl]-4,4,6-trimethyl-3,4-dihydro-1H-quinolin-2-one (Compound 56A)

To a solution of Compound 9B (52 mg, 1.0 eq.) and 3-butyn-1-ol (0.1 mL, 12.0 eq.) in 0.6 mL of NMP was added 13 mg (0.1 eq.) of tetrakis(triphenylphosphine)palladium(0) (from Strem). The reaction mixture was heated to 120° C. for 15 min in microwave. After cooling, reaction was partitioned between ammonium chloride and $CH_2Cl_2$. The aqueous layer was further extracted (2×20 mL) with $CH_2Cl_2$ and the combined organic layers were dried over sodium sulfate, filtered and concentrated. Purification by preparative chromatography (50:50 hexanes/EtOAc) afforded 13 mg (26%) of product (Compound 56A) as colorless oil. MS (electrospray): mass calculated for $C_{25}H_{26}F_3NO_3$, 445.47; m/z found 446.3, $[M+H]^+$.

B. 4-[3-(1-Ethyl-4,4,6-trimethyl-2-oxo-1,2,3,4-tetrahydro-quinolin-7-yl)-4-trifluoromethoxy-phenyl]-butyric acid (Compound 56)

Compound 56A was dissolved in MeOH and hydrogenated with 10% Pd/C and $H_2$ balloon overnight. Pd/C was then filtered off and solvent was evaporated to afford intermediate as colorless oil. Oil was then dissolved in acetone and treated with a few drops of Jones reagent for 5 min. Reaction was then partitioned between $CH_2Cl_2$ and brine. Organic layer was dried over sodium sulfate, filtered and concentrated. Purification by preparative chromatography (95:5 $CH_2Cl_2$/MeOH) afforded 14 mg (100%) of product (Compound 56) as white solid. MS (electrospray): mass calculated for $C_{25}H_{28}F_3NO_4$, 463.49; m/z found 464.6, [M+H]⁺.

Example 57

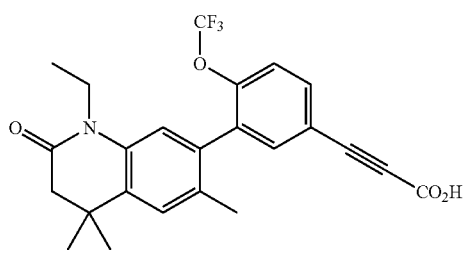

[3-(1-Ethyl-4,4,6-trimethyl-2-oxo-1,2,3,4-tetrahydro-quinolin-7-yl)-4-trifluoromethoxy-phenyl]-propynoic acid (Compound 57)

A. 1-Ethyl-7-[5-(3-hydroxy-prop-1-ynyl)-2-trifluoromethoxy-phenyl]-4,4,6-trimethyl-3,4-dihydro-1H-quinolin-2-one (Compound 57A)

Compound 57A was prepared from Compound 9B using a procedure similar to that described for Example 56A except that propargyl alcohol was used as the coupling partner. MS (electrospray): mass calculated for $C_{24}H_{24}F_3NO_3$, 431.45; m/z found 432.2, [M+H]⁺.

B. [3-(1-Ethyl-4,4,6-trimethyl-2-oxo-1,2,3,4-tetrahydro-quinolin-7-yl)-4-trifluoromethoxy-phenyl]-propynoic acid A solution of Compound 57A (74 mg, 1 eq.) and TEMPO (5.6 mg, 0.21 eq.) in 2 mL of acetonitrile and 1.5 mL of phosphate buffer was heated to 40° C. and sodium chlorite (117 mg, 6 eq., 80%) followed by bleach (0.3 mL, 0.06 eq., 0.3% solution in water) were added. Reaction was left to stir at 40° C. overnight. After cooling, reaction was diluted with water and pH was adjusted to −8-9 with 2 M NaOH. Sodium sulfite (159 mg dissolved in 3 ml of water) was added and reaction was stirred for 30 min, after which it was acidified with 3 M HCl. Reaction was then extracted with $CH_2Cl_2$ (2×50 mL), organic layer was dried over sodium sulfate, filtered and concentrated. Purification by preparative chromatography (90:10 $CH_2Cl_2$/MeOH) afforded 18 mg (24%) of product (Compound 57A) as white solid. MS (electrospray): mass calculated for $C_{24}H_{22}F_3NO_4$, 445.43; m/z found 446.3, [M+H]⁺.

Example 58

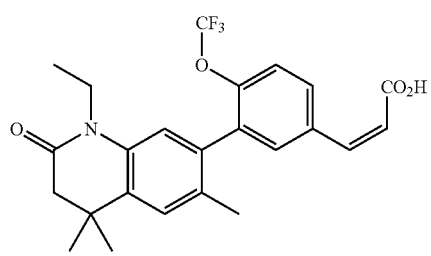

3-[3-(1-Ethyl-4,6,6-trimethyl-2-oxo-1,2,3,4-tetrahydro-quinolin-7-yl)-4-trifluoromethoxy-phenyl]-acrylic acid (Compound 58)

Compound 58 was prepared from Compound 1A using a procedure similar to the one described for Example 2, except that Triton B was used as the base and diphenylphosphonic acid ethyl ester were used to obtain the cis-double bond as the major isomer in step 2B. MS (electrospray): mass calculated for $C_{24}H_{24}F_3NO_4$, 447.17; m/z found 448.2 [M+H]⁺.

Example 59

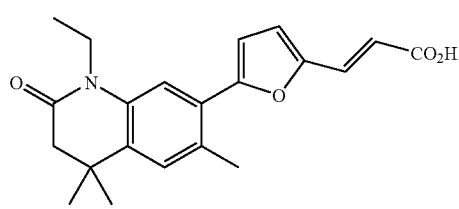

3-[5-(1-Ethyl-4,4,6-trimethyl-2-oxo-1,2,3,4-tetrahydro-quinolin-7-yl)-furan-2-yl]-acrylic acid (Compound 59)

Compound 59 was prepared from Compound 1A using a procedure similar to the one described for Example 1, except using 5-formyl-2-furanboronic acid as the starting material for step 1B. MS (electrospray): mass calculated for $C_{21}H_{23}NO_4$, 353.16; m/z found 354 [M+H]⁺.

Example 60

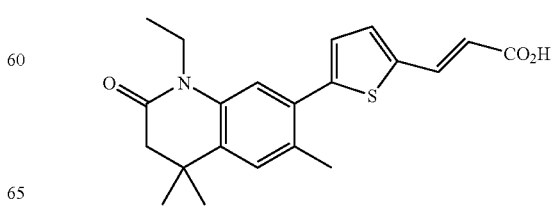

3-[5-(1-Ethyl-4,4,6-trimethyl-2-oxo-1,2,3,4-tetrahydro-quinolin-7-yl)-thiophen-2-yl]-acrylic acid (Compound 60)

Compound 60 was prepared from Compound 1A using a procedure similar to the one described for in Example 1, except using 5-formyl-2-thiopheneboronic acid as the starting material for step 1B. MS (electrospray): mass calculated for $C_{21}H_{23}NO_3S$, 369.14; m/z found 370 $[M+H]^+$.

D) General Administration, Formulation, and Dosages

The present compounds are RXR agonists and are therefore useful in treating, preventing, or inhibiting the progression of RXR mediated conditions, such as metabolic disorders including diabetes, dyslipidemia, hypercholesterolemia, and associated symptoms or complications thereof, as well as various cancerous and precancerous conditions in the breast, skin, prostate, cervix, uterus, colon, bladder, esophagus, stomach, lung, larynx, oral cavity, blood and/or lymphatic systems.

The invention features a method for treating a subject with a RXR mediated disease, said method comprising administering to the subject a therapeutically effective amount of a pharmaceutical composition comprising a compound of the invention. The invention also provides a method for treating or inhibiting the progression of diabetes, dyslipidemia, hypercholesterolemia, and associated symptoms or complications thereof in a subject, wherein the method comprises administering to the subject a therapeutically effective amount of a pharmaceutical composition comprising a compound of the invention.

Pharmaceutically acceptable salts include the therapeutically active non-toxic salts of disclosed compounds. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term "salt" also comprises the solvates which the disclosed compounds, as well as the salts thereof, are able to form. Such solvates are for example hydrates, alcoholates and the like. Conversely the salt form can be converted by treatment with alkali into the free base form.

Stereoisomeric forms define all the possible isomeric forms which the compounds of the invention may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

The next section includes detailed information relating to the use of the disclosed compounds and compositions.

E) Use

The compounds of the present invention are pharmaceutically active, for example, as RXR agonists. According to one aspect of the invention, the compounds are preferably selective RXR agonists.

Examples of RXR-mediated diseases include IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease (e.g., acute coronary syndromes or ACS, including but not limited to, non-ST segment myocardial infarction and ST-segment elevation myocardial infarctions), irritable bowel disorder, inflammation, cardiovascular disorders and cataracts.

According to one aspect of the invention, the disclosed compounds and compositions are useful for the amelioration of symptoms associated with, the treatment of, and the prevention of, the following conditions and diseases: phase I hyperlipidemia, pre-clinical hyperlipidemia, phase II hyperlipidemia, hypercholesteremia, hypertriglyceridemia, diabetes, insulin resistance, impaired glucose tolerance, dyslipidemia, and cardiovascular disorders. Preferred compounds of the invention are useful in lowering serum levels of low-density lipoproteins (LDL), intermediate density lipoprotein (IDL), and/or small LDL and other atherogenic molecules, or molecules that cause atherosclerotic complications, thereby reducing cardiovascular disorders and/or complications thereof. Preferred compounds are also useful in elevating serum levels of high-density lipoproteins (HDL), as well as in lowering serum levels of triglycerides and/or free fatty acids.

According to one aspect of the invention, the disclosed compounds may be used in a method for treating or inhibiting the progression of an RXR mediated condition and, optionally, an additional Retinoid A Receptor mediated condition, said method comprising administering to a patient in need of treatment a pharmaceutically effective amount of a composition of the invention.

Another aspect of the invention is a method of use wherein the RXR mediated condition is acute coronary syndromes such as non-ST segment myocardial infarction and ST-segment elevation myocardial infarctions.

A further aspect of the invention is a method for treating at least one RXR mediated condition and at least one Retinoid A Receptor mediated condition in a patient, said method comprising administering to a patient in need of treatment a pharmaceutically effective amount of a composition of the invention.

The invention also features pharmaceutical compositions which include, without limitation, one or more of the disclosed compounds, and pharmaceutically acceptable carriers or excipients.

1. Dosages

Those of skill in the treatment of disorders or conditions mediated by RXR could easily determine the effective daily amount from the test results presented hereinafter and other information. The exact dosage and frequency of administration depends on the particular compound of invention used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines in practicing the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to about 300 mg/kg (preferably from about 0.01 mg/kg to about 100 mg/kg; and, more preferably, from about 0.01 mg/kg to about 30 mg/kg) and may be given at a dosage of from about 0.01 mg/kg/day to about 300 mg/kg/day (preferably from about 0.01 mg/kg/day to about 100 mg/kg/day and more preferably from about 0.01 mg/kg/day to about 30 mg/kg/day). Preferably, the method for the treatment of metabolic disorders described in the present invention using any of the compounds as defined herein, the dosage form will contain a pharmaceutically acceptable carrier containing between from about 0.01 mg to about 100 mg; and, more preferably, from about 5 mg to about 50 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W.R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent (s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of this invention may be administered in any of the foregoing compositions and dosage regimens or by means of those compositions and dosage regimens established in the art whenever treatment of RXR mediated disorders is required for a subject in need thereof.

The daily dose of a pharmaceutical composition of the present invention may be varied over a wide range from about 0.7 mg to about 500 mg per adult human per day; preferably, the dose will be in the range of from about 0.7 mg to about 100 mg per adult human per day; most preferably the dose will be in the range of from about 0.7 mg to about 50 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. An effective amount of the drug is ordinarily supplied at a dosage level of from about 0.01 mg/kg to about 300 mg/kg of body weight per day. Advantageously, a compound of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

2. Formulations

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

The compounds of the present invention may be formulated into various pharmaceutical forms for administration purposes. Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

3. Combination Therapy

The compounds of the present invention may be used in combination with one or more pharmaceutically active agents. These agents include other RXR modulators, other RAR modulators, other anti-diabetic agents, other lipid lowering agents, as well as blood pressure lowering agents such as statin drugs and the fibrates.

Other RXR modulators include, but are not limited to:
(1) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455);
(2) 9-cis-retinoic acid;
(3) AGN-4326 (also known as ALRT-4204, AGN-4204, ALRT-326, ALRT-324, or LGD 1324);
(4) LGD 1324 (ALRT 324);
(5) LG 100754;
(6) LY-510929;
(7) LGD 1268 (6-(1,1,4,4,6-pentamethyl-1,2,3,4-tetrahydro-naphth-7-ylcycloprop-1-yl)nicotinic acid, known as ALRT 268 or LG 100268);
(8) LG 100264; and
(9) substituted heterocycles as disclosed in PCT publications WO 01/16122 and WO 01/16123 by Maxia.

One preferred example of substituted heterocycles is MX-6054, which is 2,4-thiazolidinedione, 5-[[3-(5,6,7,8-tetrahydro-3,5,5,8,8-pentamethyl-2-naphthalenyl)-4-(trifluoromethoxy)phenyl]methylene]-, (5Z)-, also named 3-(3,5,5,8,8-pentamethyl-5,6,7,8-tetrahydro-2-naphthyl)-4-trifluoromethoxybenzylidene-2,4-thiazolidinedione, represented by the following formula:

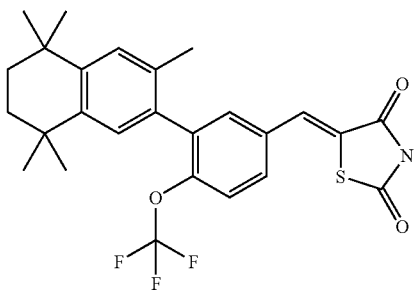

Another preferred example of substituted heterocycles is 2,4-thiazolidinedione, 5-[[3-(1-ethyl-1,2,3,4-tetrahydro-4,4,6-trimethyl-2-oxo-7-quinolinyl)-4-(trifluoromethoxy)phenyl]methylene]-, (5Z)-, represented by the following formula:

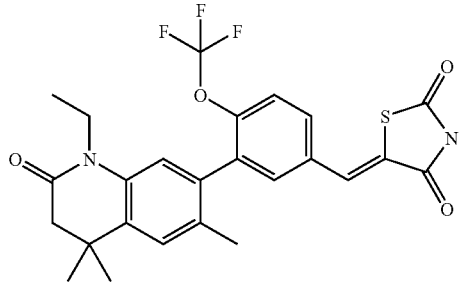

Preferred substituted heterocycles are selected from:
3-(3,5,5,8,8-pentamethyl-5,6,7,8-tetrahydro-2-naphthyl)-4-trifluoromethoxybenzylidene-2,4-thiazolidinedione;
4-[2-(3,5,5,8,8-pentamethyl-5,6,7,8-tetrahydro-2-naphthyl)-1,3-dioxolane]benzylidene-2,4-thiazolidinedione;
4-[2-(5,5,8,8-tetramethyl-5,6,7,8-tetrahydro-2-naphthyl)-2-propyl]benzylidene-2,4-thiazolidinedione;
4-[2-(3,5,5,8,8-pentamethyl-5,6,7,8-tetrahydro-2-naphthyl)-1,3-dioxolane]benzylidene-2-thioxo-2,4-thiazolidinedione;
4-[2-(5,5,8,8-tetramethyl-5,6,7,8-tetrahydro-2-naphthyl-2-propyl]benzylidene-2-thioxo-2,4-thiazolidinedione;
4-[2-(3,5,5,8,13-pentamethyl-5,6,7,8-tetrahydro-2-naphthyl)-1,3-dioxolane]benzylidene-2-thioxo-2,4-imidazolidinedione;
4-[2-(5,5,8,8-tetramethyl-5,6,7,8-tetrahydro-2-naphthyl)-2-propyl]benzylidene-2-thioxo-2,4-imidazolidinedione;
4-[2-(3,5,5,8,8-pentamethyl-5,6,7,8-tetrahydro-2-naphthyl)-1,3-dioxolane]benzylidene-2,4-imidazolidinedione;
4-[2-(5,5,8,8-tetramethyl-5,6,7,8-tetrahydro-2-naphthyl)-2-propyl]benzylidene-2,4-imidazolidinedione;
4-[2-(3,5,5,8,8-pentamethyl-5,6,7,8-tetrahydro-2-naphthyl)-1,3-dioxolane]benzyl-2,4-thiazolidinedione;
4-[2-(5,5,8,8-tetramethyl-5,6,7,8-tetrahydro-2-naphthyl)-2-propyl]benzyl-2,4-thiazolidinedione;
4-[2-(3,5,5,8,8-pentamethyl-5,6,7,8-tetrahydro-2-naphthyl)-1,3-dioxolane]benzyl-2-thioxo-2,4-thiazolidinedione;
4-[2-(5,5,8,8-tetramethyl-5,6,7,8-tetrahydro-2-naphthyl)-2-propyl]benzyl-2-thioxo-2,4-thiazolidinedione;
4-[2-(3,5,5,8,8-pentamethyl-5,6,7,8-tetrahydro-2-naphthyl)-1,3-dioxolane]benzyl-2-thioxo-2,4-imidazolidinedione;
4-[2-(5,5,8,8-tetramethyl-5,6,7,8-tetrahydro-2-naphthyl)-2-propyl]benzyl-2-thioxo-2,4-imidazolidinedione;
4-[2-(3,5,5,8,8-pentamethyl-5,6,7,8-tetrahydro-2-naphthyl)-1,3-dioxolane]benzyl-2,4-imidazolidinedione; and
4-[2-(5,5,8,8-tetramethyl-5,6,7,8-tetrahydro-2-naphthyl)-2-propyl]benzyl-2,4-imidazolidinedione.

Other anti-diabetic agents include thiazolidinedione and non-thiazolidinedione insulin sensitizers, which decrease peripheral insulin resistance by enhancing the effects of insulin at target organs and tissues.

The following agents are known to bind and activate the nuclear receptor peroxisome proliferator-activated receptor-gamma (PPARγ) which increases transcription of specific insulin-responsive genes. Examples of PPAR-gamma agonists are thiazolidinediones such as:
(1) rosiglitazone (2,4-thiazolidinedione,5-((4-(2-(methyl-2-pyridinylamino) ethoxy)phenyl)methyl)-, (Z)-2-butenedioate (1:1) or 5-((4-(2-(methyl-2-pyridinylamino) ethoxy)phenyl)methyl)-2,4-thiazolidinedione, known as AVANDIA; also known as BRL 49653, BRL 49653C, BRL 49653c, SB 210232, or rosiglitazone maleate);
(2) pioglitazone (2,4-thiazolidinedione, 5-((4-(2-(5-ethyl-2-pyridinyl)ethoxy)phenyl)methyl)-, monohydrochloride, (+−)- or 5-((4-(2-(5-ethyl-2-pyridyl)ethoxy)phenyl)methy)-2,4-thiazolidinedione, known as ACTOS, ZACTOS, or GLUSTIN; also known as AD 4833, U 72107, U 72107A, U 72107E, pioglitazone hydrochloride (USAN));
(3) troglitazone (5-((4-((3,4-dihydro-6-hydroxy-2,5,7,8-tetramethyl-2H-1-benzopyran-2-yl)methoxy)phenyl) methyl)-2,4-thiazolidinedione, known as NOSCAL, REZULIN, ROMOZIN, or PRELAY; also known as CI 991, CS 045, GR 92132, GR 92132X);
(4) isaglitazone ((+)-5-[[6-[(2-fluorophenyl)methoxy]-2-naphthalenyl]methyl]-2,4-thiazolidinedione or 5-((6-((2 fluorophenyl)methoxy)-2-naphthalenyl)methyl-2,4-thiazolidinedione or 5-(6-(2-fluorobenzyloxy)-naphthalen-2-ylmethyl) thiazolidine-2,4-dione, also known as MCC-555 or neoglitazone); and
(5) 5-BTZD.

Additionally, the non-thiazolidinediones that act as insulin sensitizing agents include, but are not limited to:
(1) JT-501 (JTT 501, PNU-1827, PNU-716-MET-0096, or PNU 182716: isoxazolidine-3,5-dione, 4-((4-(2-phenyl-5-methyl)-1,3-oxazolyl)ethylphenyl-4) methyl-);

(2) KRP-297 (5-(2,4-dioxothiazolidin-5-ylmethyl)-2-methoxy-N-(4-(trifluoromethyl)benzyl)benzamide or 5-((2,4-dioxo-5-thiazolidinyl)methyl)-2-methoxy-N-((4 (trifluoromethyl)phenyl)methyl)benzamide); and (3) Farglitazar (L-tyrosine, N-(2-benzoylphenyl)-o-(2-(5-methyl-2-phenyl-4-oxazolyl)ethyl)- or N-(2-benzoylphenyl)-O-(2-(5-methyl-2-phenyl-4-oxazolyl)ethyl)-L-tyrosine, or GW2570 or GI-262570).

Other anti-diabetic agents have also been shown to have PPAR modulator activity such as PPAR gamma, SPPAR gamma, and/or PPAR delta/gamma agonist activity. Examples are listed below:

(1) AD 5075;
(2) R 119702 ((+−)-5-(4-(5-Methoxy-1H benzimidazol-2-ylmethoxy)benzyl)thiazolin-2,4-dione hydrochloride, or CI 1037 or CS 011);
(3) CLX-0940 (peroxisome proliferator-activated receptor alpha agonist/peroxisome proliferator-activated receptor gamma agonist);
(4) LR-90 (2,5,5-tris(4-chlorophenyl)-1,3-dioxane-2-carboxylic acid, PPARdelta/γ agonist);
(5) Tularik (PPARγ agonist);
(6) CLX-0921 (PPARγ agonist);
(7) CGP-52608 (PPAR agonist);
(8) GW-409890 (PPAR agonist);
(9) GW-7845 (PPAR agonist);
(10) L-764406 (PPAR agonist);
(11) LG-101280 (PPAR agonist);
(12) LM-4156 (PPAR agonist);
(13) Risarestat (CT-112);
(14) YM 440 (PPAR agonist);
(15) AR-H049020 (PPAR agonist);
(16) GW 0072 (4-(4-((2S,5S)-5-(2-(bis(phenylmethyl)amino)-2-oxoethyl)-2-heptyl-4-oxo-3-thiazo lidinyl) butyl)benzoic acid);
(17) GW 409544 (GW-544 or GW-409544);
(18) NN 2344 (DRF 2593);
(19) NN 622 (DRF 2725);
(20) AR-H039242 (AZ-242);
(21) GW 9820 (fibrate);
(22) GW 1929 (N (2-benzoylphenyl)-O-(2-(methyl-2-pyridinylamino)ethyl)-L-tyrosine, known as GW 2331, PPAR alpha/γ agonist);
(23) SB 219994 ((S)-4-(2-(2-benzoxazolylmethylamino) ethoxy)-alpha-(2,2,2-trifluoroethoxy)benzen epropanoic acid or 3-(4-(2-(N-(2-benzoxazolyl)-N-methylamino)ethoxy)phenyl)-2 (S)-(2,2,2-trifluoroethoxy) propionic acid or benzenepropanoic acid,4-(2-(2-benzoxazolylmethylamino)ethoxy)-alpha-(2,2,2-trifluoroethoxy)-, (alphaS)-, PPAR alpha/γ agonist);
(24) L-796449 (PPAR alpha/γ agonist);
(25) Fenofibrate (Propanoic acid, 2-[4-(4-chlorobenzoyl) phenoxy]-2-methyl-, 1-methylethyl ester, known as TRICOR, LIPCOR, LIPANTIL, LIPIDIL MICRO PPAR alpha agonist);
(26) GW-9578 (PPAR alpha agonist);
(27) GW-2433 (PPAR alpha/γ agonist);
(28) GW-0207 (PPARγ agonist);
(29) LG-100641 (PPARγ agonist);
(30) LY-300512 (PPARγ agonist);
(31) NID525-209 (NID-525);
(32) VDO-52 (VDO-52);
(33) LG 100754 (peroxisome proliferator-activated receptor agonist);
(34) LY-510929 (peroxisome proliferator-activated receptor agonist);
(35) bexarotene (4-(1-(3,5,5,8,8-pentamethyl-5,6,7,8-tetrahydro-2-naphthalenyl)ethenyl)benzoic acid, known as TARGRETIN, TARGRETYN, TARGREXIN; also known as LGD 1069, LG 100069, LG 1069, LDG 1069, LG 69, RO 264455); and
(36) GW-1536 (PPAR alpha/γ agonist).

Other insulin sensitizing agents include, but are not limited to:

(1) INS-1 (D-chiro inositol or D-1, 2, 3, 4, 5, 6-hexahydroxycyclohexane);
(2) protein tyrosine phosphatase 1 B (PTP-1B) inhibitors;
(3) glycogen synthase kinase-3 (GSK3) inhibitors;
(4) beta 3 adrenoceptor agonists such as ZD 2079 ((R)—N-(2-(4-(carboxymethyl)phenoxy)ethyl)-N-(2-hydroxy-2-phenethyl) ammonium chloride, also known as ICI D 2079) or AZ 40140;
(5) glycogen phosphorylase inhibitors;
(6) fructose-1,6-bisphosphatase inhibitors;
(7) chromic picolinate, vanadyl sulfate (vanadium oxysulfate);
(8) KP 102 (organo-vanadium compound);
(9) chromic polynicotinate;
(10) potassium channel agonist NN 414;
(11) YM 268 (5,5'-methylene-bis(1,4-phenylene)bismethylenebis (thiazolidine-2,4-dione);
(12) TS 971;
(13) T 174 ((+−)-5-(2,4-dioxothiazolidin-5-ylmethyl)-2-(2-naphthylmethyl)benzoxazole);
(14) SDZ PGU 693 ((+)-trans-2 (S-((4-chlorophenoxy) methyl)-7alpha-(3,4-dichlorophenyl)tetrahydropyrrolo (2,1-b) oxazol-5(6H)-one);
(15) S 15261 ((−)-4-(2-((9H-fluoren-9-ylacetyl)amino) ethyl)benzoic acid 2-((2-methoxy-2-(3-(trifluoromethyl)phenyl)ethyl)amino)ethyl ester);
(16) AZM 134 (Alizyme);
(17) ARIAD;
(18) R 102380;
(19) PNU 140975 (1-(hydrazinoiminomethyl)hydrazino) acetic acid;
(20) PNU 106817 (2-(hydrazinoiminomethyl)hydrazino) acetic acid;
(21) NC 2100 (5-((7-(phenylmethoxy)-3-quinolinyl)methyl)-2,4-thiazolidinedione;
(22) MXC 3255;
(23) MBX 102;
(24) ALT 4037;
(25) AM 454;
(26) JTP 20993 (2-(4-(2-(5-methyl-2-phenyl-4-oxazolyl) ethoxy)benzyl)-malonic acid dimethyl diester);
(27) Dexlipotam (5(R)-(1,2-dithiolan-3-yl)pentanoic acid, also known as (R)-alpha lipoic acid or (R)-thioctic acid);
(28) BM 170744 (2,2-Dichloro-12-(p-chlorophenyl)dodecanoic acid);
(29) BM 152054 (5-(4-(2-(5-methyl-2-(2-thienyl)oxazol-4-yl)ethoxy)benzothien-7-ylmethyl)thiazolidine-2,4-dione);
(30) BM 131258 (5-(4-(2-(5-methyl-2-phenyloxazol-4-yl) ethoxy)benzothien-7-ylmethyl)thiazolidine-2,4-dione);
(31) CRE 16336 (EML 16336);
(32) HQL 975 (3-(4-(2-(5-methyl-2-phenyloxazol-4-yl) ethoxy)phenyl)-2 (S)-(propylamino)propionic acid);
(33) DRF 2189 (5-((4-(2-(1-Indolyl)ethoxy)phenyl)methyl)thiazolidine-2,4-dione);
(34) DRF 554158;
(35) DRF-NPCC;
(36) CLX 0100, CLX 0101, CLX 0900, or CLX 0901;
(37) IkappaB Kinase (IKK B) Inhibitors

(38) mitogen-activated protein kinase (MAPK) inhibitors p38 MAPK Stimulators
(39) phosphatidyl-inositide triphosphate
(40) insulin recycling receptor inhibitors
(41) glucose transporter 4 modulators
(42) TNF-☐ antagonists
(43) plasma cell differentiation antigen-1 (PC-1) Antagonists
(44) adipocyte lipid-binding protein (ALBP/aP2) inhibitors
(45) phosphoglycans
(46) Galparan;
(47) Receptron;
(48) islet cell maturation factor;
(49) insulin potentiating factor (IPF or insulin potentiating factor-1);
(50) somatomedin C coupled with binding protein (also known as IGF-BP3, IGF-BP3, SomatoKine);
(51) Diab II (known as V-411) or Glucanin, produced by Biotech Holdings Ltd. or Volque Pharmaceutical;
(52) glucose-6 phosphatase inhibitors;
(53) fatty acid glucose transport protein;
(54) glucocorticoid receptor antagonists; and
(55) glutamine:fructose-6-phosphate amidotransferase (GFAT) modulators.

Anti-diabetic agents also include biguanides, which decreases liver glucose production and increases the uptake of glucose. Examples of biguanides include metformin such as:
(1) 1,1-dimethylbiguanide (e.g., Metformin—DepoMed, Metformin—Biovail Corporation, or METFORMIN GR (metformin gastric retention polymer)); and
(2) metformin hydrochloride (N,N-dimethylimidodicarbonimidic diamide monohydrochloride, also known as LA 6023, BMS 207150, GLUCOPHAGE, or GLUCOPHAGE XR.

Anti-diabetic agents also include alpha-glucosidase inhibitors, which inhibit alpha-glucosidase. Alpha-glucosidase converts fructose to glucose, thereby delaying the digestion of carbohydrates. The undigested carbohydrates are subsequently broken down in the gut, reducing the post-prandial glucose peak. Examples of alpha-glucosidase inhibitors include, but are not limited to:
(1) acarbose (D-glucose, O-4,6-dideoxy-4-(((1S-(1alpha, 4alpha,5beta,6alpha))-4,5,6-trihydroxy-3-(hydroxymethyl)-2-cyclohexen-1-yl)amino)-alpha-D-lucopyranosyl-(1-4)-O-alpha-D-glucopyranosyl-(1-4)-, also known as AG-5421, Bay-g-542, BAY-g-542, GLUCOBAY, PRECOSE, GLUCOR, PRANDASE, GLUMIDA, or ASCAROSE);
(2) Miglitol (3,4,5-piperidinetriol, 1-(2-hydroxyethyl)-2-(hydroxymethyl)-, (2R (2alpha, 3beta, 4alpha, 5beta))- or (2R,3R,4R,5S)-1-(2-hydroxyethyl)-2-(hydroxymethyl-3,4,5-piperidinetriol, also known as BAY 1099, BAY M 1099, BAY-m-1099, BAYGLITOL, DIASTABOL, GLYSET, MIGLIBAY, MITOLBAY, PLUMAROL);
(3) CKD-711 (0-4-deoxy-4-((2,3-epoxy-3-hydroxymethyl-4,5,6-trihydroxycyclohexane-1-yl)amino)-alpha-b glucopyranosyl-(1-4)-alpha-D-glucopyranosyl-(1-4)-D-glucopyranose);
(4) emiglitate (4-(2-((2R,3R,4R,5S)-3,4,5-trihydroxy-2-(hydroxymethyl)-1-piperidinyl)ethoxy)benzoic acid ethyl ester, also known as BAY o 1248 or MKC 542);

(5) MOR 14 (3,4,5-piperidinetriol, 2-(hydroxymethyl)-1-methyl-, (2R-(2alpha,3beta,4alpha,5beta))-, also known as N-methyldeoxynojirimycin or N-methylmoranoline); and
(6) Voglibose (3,4-dideoxy-4-((2-hydroxy-1-(hydroxymethyl)ethyl)amino)-2-C-(hydroxymethyl)-D-epi inositol or D-epi-Inositol,3,4-dideoxy-4-((2 hydroxy-1-(hydroxymethyl)ethyl) amino)-2-C-(hydroxymethyl)-, also known as A 71100, AO 128, BASEN, GLUSTAT, VOGLISTAT.

Anti-diabetic agents also include insulins such as regular or short-acting, intermediate-acting, and long-acting insulins, non-injectable or inhaled insulin, tissue selective insulin, glucophosphokinin (D-chiroinositol), insulin analogues such as insulin molecules with minor differences in the natural amino acid sequence and small molecule mimics of insulin (insulin mimetics), and endosome modulators. Examples include, but are not limited to:
(1) Biota;
(2) LP 100;
(3) (SP-5-21)-oxobis (1-pyrrolidinecarbodithioato-S, S') vanadium,
(4) insulin aspart (human insulin (28B-L-aspartic acid) or B28-Asp-insulin, also known as insulin X14, INA-X14, NOVORAPID, NOVOMIX, or NOVOLOG);
(5) insulin detemir (Human 29B-(N6-(1-oxotetradecyl)-L lysine)-(1A-21A), (1B-29B)-Insulin or NN 304);
(6) insulin lispro ("28B-L-lysine-29B-L-proline human insulin, or Lys(B28), Pro(B29) human insulin analog, also known as lys-pro insulin, LY 275585, HUMALOG, HUMALOG MIX 75/25, or HUMALOG MIX 50/50);
(7) insulin glargine (human (A21-glycine, B31-arginine, B32-arginine) insulin HOE 901, also known as LANTUS, OPTISULIN);
(8) Insulin Zinc Suspension, extended (Ultralente), also known as HUMULIN U or ULTRALENTE;
(9) Insulin Zinc suspension (Lente), a 70% crystalline and 30% amorphous insulin suspension, also known as LENTE ILETIN II, HUMULIN L, or NOVOLIN L;
(10) HUMULIN 50/50 (50% isophane insulin and 50% insulin injection);
(11) HUMULIN 70/30 (70% isophane insulin NPH and 30% insulin injection), also known as NOVOLIN 70/30, NOVOLIN 70/30 PenFill, NOVOLIN 70/30 Prefilled;
(12) insulin isophane suspension such as NPH ILETIN II, NOVOLIN N, NOVOLIN N PenFill, NOVOLIN N Prefilled, HUMULIN N;
(13) regular insulin injection such as ILETIN II Regular, NOVOLIN R, VELOSULIN BR, NOVOLIN R PenFill, NOVOLIN R Prefilled, HUMULIN R, or Regular U-500 (Concentrated);
(14) ARIAD;
(15) LY 197535;
(16) L-783281; and
(17) TE-17411.

Anti-diabetic agents also include insulin secretion modulators such as:
(1) glucagon-like peptide-1 (GLP-1) and its mimetics;
(2) glucose-insulinotropic peptide (GIP) and its mimetics;
(3) exendin and its mimetics;
(4) dipeptyl protease (DPP or DPPIV) inhibitors such as
(4a) DPP-728 or LAF 237 (2-pyrrolidinecarbonitrile,1-(((2-((5-cyano-2-pyridinyl)amino)ethyl)amino) acetyl), known as NVP-DPP 728, DPP-728A, LAF-237);
(4b) P 3298 or P32/98 (di-(3N-((2S,3S)-2-amino-3-methyl-pentanoyl)-1,3-thiazolidine) fumarate);

(4c) TSL 225 (tryptophyl-1,2,3,4-tetrahydroisoquinoline-3-carboxylic acid);
(4d) Valine pyrrolidide (valpyr);
(4e) 1-aminoalkylisoquinolinone-4-carboxylates and analogues thereof;
(4f) SDZ 272-070 (1-(L-Valyl)pyrrolidine);
(4g) TMC-2A, TMC-2B, or TMC-2C;
(4h) Dipeptide nitriles (2-cyanopyrrolodides);
(4i) CD26 inhibitors; and
(4j) SDZ 274-444;
(5) glucagon antagonists such as AY-279955; and
(6) amylin agonists which include, but are not limited to, pramlintide (AC-137, Symlin, tripro-amylin or pramlintide acetate).

Known anti-diabetic agents include insulin, sulfonylureas, biguanides, meglitinides, AGI's (Alpha-Glucosidase Inhibitors; e.g., Glyset), PPAR alpha agonists, and PPAR gamma agonists, and dual PPAR alpha/gamma agonists.

Examples of lipid lowering agents include bile acid sequestrants, fibric acid derivatives, nicotinic acid, and HMGCoA reductase inhibitors. Specific examples include statins such as LIPITOR®, ZOCOR®, PRAVACHOL®, LESCOL®, and MEVACOR®, and pitavastatin (nisvastatin) (Nissan, Kowa Kogyo, Sankyo, Novartis) and extended release forms thereof, such as ADX-159 (extended W release lovastatin), as well as Colestid, Locholest, Questran, Atromid, Lopid, and Tricor.

Examples of blood pressure lowering agents include antihypertensive agents, such as angiotensin-converting enzyme (ACE) inhibitors (Accupril, Altace, Captopril, Lotensin, Mavik, Monopril, Prinivil, Univasc, Vasotec, and Zestril), adrenergic blockers (such as Cardura, Dibenzyline, Hylorel, Hytrin, Minipress, and Minizide) alpha/beta adrenergic blockers (such as Coreg, Normodyne, and Trandate), calcium channel blockers (such as Adalat, Calan, Cardene, Cardizem, Covera-HS, Dilacor, DynaCirc, Isoptin, Nimotop, Norvace, Plendil, Procardia, Procardia XL, Sula, Tiazac, Vascor, and Verelan), diuretics, angiotensin II receptor antagonists (such as Atacand, Avapro, Cozaar, and Diovan), beta adrenergic blockers (such as Betapace, Blocadren, Brevibloc, Cartrol, Inderal, Kerlone, Lavatol, Lopressor, Sectral, Tenormin, Toprol-XL, and Zebeta), vasodilators (such as Deponit, Dilatrate, SR, Imdur, Ismo, Isordil, Isordil Titradose, Monoket, Nitro-Bid, Nitro-Dur, Nitrolingual Spray, Nitrostat, and Sorbitrate), and combinations thereof (such as Lexxel, Lotrel, Tarka, Teczem, Lotensin HCT, Prinzide, Uniretic, Vaseretic, Zestoretic).

In addition, a second RXR or RAR modulator, as described above in Section B), may also be utilized as a third antidiabetic agent, provided that it is different from the first RXR or RAR modulator.

F) Biological Examples

ABCA1 bDNA Assay

THP-1 cells, a human monocytic cell line, were obtained from ATCC and maintained in RPMI (Gibco) supplemented with 10% fetal bovine serum (Gibco), 2 mM L-glutamine and 1% antibiotic-antimycotic in 5% $CO_2$ at 37° C. For ABCA1 mRNA induction assays, the cells were pelleted and resuspended in RPMI supplemented with 0.5% charcoal treated serum (Hyclone), 2 mM glutamine and 1% antibiotic-antimycotic. The cells were plated at a density of 40,000 cells/90 □l and incubated as above for at least 4 hours before the initiation of treatments. Compounds were prepared as 10 mM stocks in DMSO. For treatments, the compounds were diluted in medium and 10 □l of 10× stocks were added to the cells at a final concentration 0.1% DMSO. The cells were incubated for the desired amount of time (usually 18-24 hrs) and then lyzed with 50 □l of Quantigene HV bDNA lysis buffer which also contained the ABCA1 bDNA probes (probe sequences shown below):

| ABCA1 bDNA probe sequences | |
|---|---|
| Primer Name | Sequence |
| hABC1001 | CGGGTAACGGAAACAGGGGTTGTTTTTCTCTTGGAAAGAAAGT |
| hABC1002 | TCCGGGAGCCTCCCCAGGAGTTTTTCTCTTGGAAAGAAAGT |
| hABC1003 | GCCAGTTTCTCCCTTGGTAGTTTTTCTCTTGGAAAGAAAGT |
| hABC1004 | CTCCTTGCTCGGGAAGGGTTTTTCTCTTGGAAAGAAAGT |
| hABC1005 | AACAGCTCCTGGGCCAGAGTTTTTCTCTTGGAAAGAAAGT |
| hABC1006 | TTCAGCCCCCTCCCTCGGGATTTTTTCTCTTGGAAAGAAAGT |
| hABC1007 | ATGCGGGAAAGAGGACTAGTTTTTCTCTTGGAAAGAAAGT |
| hABC1008 | GTTCACCTCAGCCATGACCTTTTTCTCTTGGAAAGAAAGT |
| hABC1009 | CATGCCTTCCAGATCATGGAACTTTTTCTCTTGGAAAGAAAGT |
| hABC1010 | GCGAGCCACAATGGATTTTTTTAGGCATAGGACCCGTGTCT |
| hABC1011 | CTCCGAGCATCTGAGAACAGTTTTTAGGCATAGGACCCGTGTCT |
| hABC1012 | TCAGAACTTTGCGCATGTCCTTTTTTAGGCATAGGACCCGTGTCT |
| hABC1013 | GGATTTCTTGATCTGCTGTAATGTTCTTTTTAGGCATAGGACCCGTGTCT |
| hABC1014 | AAGGTTTCATTGTCCACCAGGAATTTTTAGGCATAGGACCCGTGTCT |

| ABCA1 bDNA probe sequences | |
|---|---|
| Primer Name | Sequence |
| hABC1015 | GGTTGTGATACAGGAACCCAGAGTTTTTAGGCATAGGACCCGTGTCT |
| hABC1016 | GTCCACAGTAGACTTTGGGAGAGAGATTTTTAGGCATAGGACCCGTGTCT |
| hABC1017 | TGACATCAGCCCTCAGCATCTTTTTTTAGGCATAGGACCCGTGTCT |
| hABC1018 | CTTGTCAAATGTAAGTGGTAGCCTTTTTTAGGCATAGGACCCGTGTCT |
| hABC1019 | CTGATTTTGATCCATTGCACAGATTTTTAGGCATAGGACCCGTGTCT |
| hABC1020 | GGCTTCAGGATGTCCATGTTGTTTTAGGCATAGGACCCGTGTCT |
| hABC1021 | AGATGTAGAGTTTAGTGTTCTCAGGATTTTTTAGGCATAGGACCCGTGTCT |
| hABC1022 | TTTTGTGGCTTCGGCCAGTTTTTAGGCATAGGACCCGTGTCT |
| hABC1023 | TCCCAAGACTATGCAGCAATGTTTTTAGGCATAGGACCCGTGTCT |
| hABC1024 | GTCACTCCAGCTTCTCATGCTGTTTTAGGCATAGGACCCGTGTCT |
| hABC1025 | GAAACATCACCTCCTGTCGCATTTTTAGGCATAGGACCCGTGTCT |
| hABC1026 | GCCTGGTAGATTTGGGTGGTTTTAGGCATAGGACCCGTGTCT |
| hABC1027 | GCCCGCAGACAATACGAGACACATTTTTAGGCATAGGACCCGTGTCT |
| hABC1028 | GGCTTTGTAGTTGTTGTCCTCTTTTTAGGCATAGGACCCGTGTCT |
| hABC1029 | TGCCATTGCCTCCAAAGAGTTTTTAGGCATAGGACCCGTGTCT |
| hABC1030 | AAGGTTTCAGCATCTTCCTCAGTTTTTAGGCATAGGACCCGTGTCT |
| hABC1031 | TGCAGTAAGGAGTTGTAGAGTTGTCATAGTTTTTAGGCATAGGACCCGTGTCT |
| hABC1032 | ACTCCAAATTCTTCATCAAATCATTTTTAGGCATAGGACCCGTGTCT |
| hABC1033 | CGGCTTCAGAGCTTTCCAGATATTTTTAGGCATAGGACCCGTGTCT |
| hABC1034 | GTTAAAGTTTCCAACAAC |
| hABC1035 | TGTATAAAAGAAGC |
| hABC1036 | TCATGCTGGTGTCTTTCTGGC |
| hABC1037 | ATCTTGAAGCTTCAAGTTTGAGCT |
| hABC1038 | GCAAAATACCTTGTGGAGAA |
| hABC1039 | GGTCACCAAGTTGAATCATCTCTT |
| hABC1040 | GCCACAAAGCTCAGAAACTTCTT |
| hABC1041 | GAACGAAGTACTCGCTCTGCTGCA |
| hABC1042 | AGGAGCTGGAGCTGTTCACATTGGTCA |
| hABC1043 | ATACCAGTTGAGAGACTTGATC |
| hABC1044 | ATACAGGATCTTCCCAACGAGCAG |
| hABC1045 | GCCTTGTGGCTGGAGTGTCAGGTGT |

| ABCA1 bDNA probe sequences | |
|---|---|
| Primer Name | Sequence |
| hABC1046 | ACAGCCAGTTCCTGGAAGGTCTT |

RXR Co-Transfection Assay

The nucleic acid sequence from 676-1464 bp (accession number X52773) encoding the ligand binding domains was subcloned into the pM vector (BD Biosciences Clontech, Palo Alto, Calif.) and were fused with the DNA binding domain of yeast GAL4. HEK293 cells were cultured in DMEM/F12 medium supplemented with 10% FBS and 1% l-glutamine (growth medium). Cells were seeded at a density of $5\text{-}10\times10^6$ cells in 50 ml of growth medium and left overnight. The medium was removed and the cells were washed with 15 ml of OptiMEM serum free medium (Invitrogen Corp). The cells were transfected using OptiMEM serum free medium and DMRIE transfection reagent (Invitrogen Corp). Approximately 10-30 ng of DNA for the different receptors and 5-10 ng of the luciferase reporter (1:1 ratio for RAR and 4:1 ratio for RXR of receptor DNA:reporter DNA) were gently mixed with 51 □l of DMRIE reagent in a total volume of 17 ml of OptiMEM medium. Eighteen hours after transfection, the cells were washed once with growth medium and then incubated for 6 hrs in 30 ml of growth medium. The cells were then trypsinized, and reseeded at a density of 50,000 per well in 96 well plates and left overnight. The medium was replaced with 90 □l of medium containing DMEM/F12 supplemented with 0.5% charcoal-treated FBS (HyClone; Logan, Utah) and 1% glutamine. Compounds or vehicle were added in 10 □l of 10× concentration of compound or vehicle (0.1% dimethyl sulfoxide). The cells were treated for 16-18 hours, lysed and assayed for luciferase activity using the Steady Glo luciferase assay kit (Promega, Madison, Wis.).

Compounds listed in Table II below were tested in the above assay(s):

TABLE II

| Compound # | ABCA1 $EC_{50}$ in nM (% max MX-6054) | RXR co-transfection $EC_{50}$ in nM (% of 2,4-thiazolidinedione, 5-[[3-(1-ethyl-1,2,3,4-tetrahydro-4,4,6-trimethyl-2-oxo-7-quinolinyl)-4-(trifluoro-methoxy)phenyl]methylene]-, (5Z)-) |
|---|---|---|
| 1 | 479, 114 (60) | 57.2 (76.5%)<br>72.3 (80%)<br>72.4 (82%) |
| 2 | ~3.6 (81) | 1 (130%)<br>2.5 (100%) |
| 3 | 200 (56% @3 µM) | 12.8 (76%)<br>35.8 (92%) |
| 4 | 10 (70.3% @0.3 µM) | 16.3 (97%) |
| 9 | 100 (39.9% @0.3 µM) | 31.7 (71%)<br>24.2 (92%) |
| 11 | 44 (24.5% @3 µM) (32% @3 µM) | 23.1 (64%) |
| 12 | 510 (59) | 71.2 (85%)<br>62.7 (85%)<br>36.7 (85%) |
| 26 | 47 (56.8) | 7.1 (95%)<br>7.3 (63%) |
| 28 | 1 (59) | 3.4 (80%) |
| 30 | 347 (160) | 46.3 (99%)<br>29.1 (100%) |
| 31 | 369 (45) | 59.6 (89%)<br>12.6 (85%)<br>37.2 (60%) |
| 42 | >1400 (38% @3 µM) | 144 (108%) |
| 43 | >1000 (56% @3 µM) | 2.9 (121%)<br>7.1 (85%) |
| 44 | 1524 (29) | 251 (97%)<br>164 (80%) |
| 58 | 886 (75) | ~50.9 (93%)<br>27.2 (100%) |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method for treating or ameliorating a retinoid X receptor mediated condition in a subject in need thereof, wherein the retinoid X receptor condition is selected from IDDM, NIDDM, IGT, IFG, Syndrome X (or Metabolic Syndrome), insulin resistance, obesity, hyperlipidemia (including, phase I hyperlipidemia, pre-clinical hyperlipidemia, and phase II hyperlipidemia), hypercholesteremia, hypertriglyceridemia, insulin resistance, dyslipidemia, nephropathy, neuropathy, retinopathy, atherosclerosis, low HDL, non-alcoholic steatohepatitis, polycystic ovary syndrome or polycystic ovarian syndrome, hypertension, ischemia, stroke, high blood pressure, heart disease, irritable bowel disorder, inflammation, cardiovascular disorders and cataracts, comprising administering to the subject a therapeutically effective amount of at least one compound of Formula (I)

[Structure of Formula (I): a 3,4-dihydroquinolin-2(1H)-one with substituents $R_1$ on N, $R_2$ and $R_3$ at the 4-position, $R_4$ at the 7-position, $R_5$ at the 6-position, $R_6$ at the 5-position]

wherein
  $R_1$ is H or optionally substituted $C_{1-3}$alkyl;
  $R_2$ and $R_3$ are independently $C_{1-3}$alkyl;
  $R_4$ is $$-\overset{(R_a)_n}{\underset{(R_b)_m}{Z}}-X-C(O)OH,$$

wherein
  Z is selected from

[phenyl ring]

X is selected from a bond, optionally substituted —O—$C_{1-5}$alkyl-, and optionally substituted $C_{1-6}$alkylene;
  $R_a$ and $R_b$ are independently selected from optionally substituted $C_{1-3}$alkyl, optionally substituted —$C_{2-3}$alkenyl, and optionally substituted $C_{1-3}$alkoxy; and
  m and n are independently selected from 0, 1, and 2, except that m and n cannot both be 2;
or alternatively $R_4$ is H or optionally substituted $C_{1-3}$alkyl;
with the proviso that when $R_4$ is $$-\overset{(R_a)_n}{\underset{(R_b)_m}{Z}}-X-C(O)OH,$$

then $R_5$ cannot be $$-\overset{(R_a)_n}{\underset{(R_b)_m}{Z}}-X-C(O)OH,$$

provided further that when $R_4$ is H or optionally substituted $C_{1-3}$alkyl, then $R_5$ cannot be H or optionally substituted $C_{1-3}$alkyl;
  $R_5$ is $$-\overset{(R_a)_n}{\underset{(R_b)_m}{Z}}-X-C(O)OH,$$

wherein
  Z is selected from

[phenyl ring]

X is selected from a bond, optionally substituted —O—$C_{1-5}$alkyl-, and optionally substituted $C_{1-6}$alkylene;
  $R_a$ and $R_b$ are independently selected from optionally substituted $C_{1-3}$alkyl, optionally substituted —$C_{2-3}$alkenyl, and optionally substituted $C_{1-3}$alkoxy; and
  m and n are independently selected from 0, 1, and 2, except that m and n cannot both be 2;
or alternatively $R_5$ is H or optionally substituted $C_{1-3}$alkyl;
with the proviso that when $R_5$ is $$-\overset{(R_a)_n}{\underset{(R_b)_m}{Z}}-X-C(O)OH,$$

then $R_4$ cannot be $$-\overset{(R_a)_n}{\underset{(R_b)_m}{Z}}-X-C(O)OH,$$

provided further that when $R_5$ is H or optionally substituted $C_{1-3}$alkyl, then $R_4$ cannot be H or optionally substituted $C_{1-3}$alkyl; and
  $R_6$ is H or $C_{1-3}$alkyl;
or an optical isomer, enantiomer, diastereomer, racemate, or pharmaceutically acceptable salt thereof.

2. The method of claim 1 wherein the RXR condition is selected from diabetes, dyslipidemia, hypercholesterolemia, and associated symptoms or complications thereof.

3. The method of claim 2 comprising administering to the subject a therapeutically effective amount of (a) at least one compound of claim 1; and (b) at least one additional agent selected from a retinoid receptor agonist, an anti-diabetic agent, a lipid lowering agent, an anti-thrombotic agent, and a blood pressure lowering agent, said administration being in any order.

4. The method of claim 3 wherein the additional agent is a RXR agonist.

5. The method of claim 1 wherein the therapeutically effective amount of the compound of Formula 1 is from about 0.001 mg/kg/day to about 5 mg/kg/day.

* * * * *

SEQUENCE LISTING

<160> NUMBER OF SEQ ID NOS: 46

<210> SEQ ID NO 1
<211> LENGTH: 43
<212> TYPE: DNA
<213> ORGANISM: Artificial Sequence
<220> FEATURE:
<223> OTHER INFORMATION: Synthetic

<400> SEQUENCE: 1
cgggtaacgg aaacaggggt tgttttctc ttggaaagaa agt                43

<210> SEQ ID NO 2
<211> LENGTH: 42
<212> TYPE: DNA
<213> ORGANISM: Artificial Sequence
<220> FEATURE:
<223> OTHER INFORMATION: Synthetic

<400> SEQUENCE: 2
tccgggagcc tccccaggag ttttttctct tggaaagaaa gt                42

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
gccagtttct cccttggtag tttttctctt ggaaagaaag t                 41

<210> SEQ ID NO 4
<211> LENGTH: 39
<212> TYPE: DNA
<213> ORGANISM: Artificial Sequence
<220> FEATURE:
<223> OTHER INFORMATION: Synthetic

<400> SEQUENCE: 4
ctccttgctc gggaagggtt tttctcttgg aaagaaagt                    39

<210> SEQ ID NO 5
<211> LENGTH: 40
<212> TYPE: DNA
<213> ORGANISM: Artificial Sequence
<220> FEATURE:
<223> OTHER INFORMATION: Synthetic

<400> SEQUENCE: 5
aacagctcct gggccagagt ttttctcttg gaaagaaagt                   40

<210> SEQ ID NO 6
<211> LENGTH: 43
<212> TYPE: DNA
<213> ORGANISM: Artificial Sequence
<220> FEATURE:
<223> OTHER INFORMATION: Synthetic

<400> SEQUENCE: 6
ttcagccccc ctccctcggg attttttctc ttggaaagaa agt               43

<210> SEQ ID NO 7
<211> LENGTH: 40
<212> TYPE: DNA

<213> ORGANISM: Artificial Sequence
<220> FEATURE:
<223> OTHER INFORMATION: Synthetic

<400> SEQUENCE: 7
atgcgggaaa gaggactagt ttttctcttg gaaagaaagt                    40

<210> SEQ ID NO 8
<211> LENGTH: 41
<212> TYPE: DNA
<213> ORGANISM: Artificial Sequence
<220> FEATURE:
<223> OTHER INFORMATION: Synthetic

<400> SEQUENCE: 8
gttcacctca gccatgacct tttttctctt ggaaagaaag t                  41

<210> SEQ ID NO 9
<211> LENGTH: 43
<212> TYPE: DNA
<213> ORGANISM: Artificial Sequence
<220> FEATURE:
<223> OTHER INFORMATION: Synthetic

<400> SEQUENCE: 9
catgccttcc agatcatgga acttttctc ttggaaagaa agt                 43

<210> SEQ ID NO 10
<211> LENGTH: 42
<212> TYPE: DNA
<213> ORGANISM: Artificial Sequence
<220> FEATURE:
<223> OTHER INFORMATION: Synthetic

<400> SEQUENCE: 10
gcgagccaca atggattttt tttaggcata ggacccgtgt ct                 42

<210> SEQ ID NO 11
<211> LENGTH: 44
<212> TYPE: DNA
<213> ORGANISM: Artificial Sequence
<220> FEATURE:
<223> OTHER INFORMATION: Synthetic

<400> SEQUENCE: 11
ctccgagcat ctgagaacag tttttaggca taggacccgt gtct               44

<210> SEQ ID NO 12
<211> LENGTH: 45
<212> TYPE: DNA
<213> ORGANISM: Artificial Sequence
<220> FEATURE:
<223> OTHER INFORMATION: Synthetic

<400> SEQUENCE: 12
tcagaacttt gcgcatgtcc tttttaggc ataggacccg tgtct               45

<210> SEQ ID NO 13
<211> LENGTH: 50
<212> TYPE: DNA
<213> ORGANISM: Artificial Sequence
<220> FEATURE:
<223> OTHER INFORMATION: Synthetic

<400> SEQUENCE: 13
ggatttcttg atctgctgta atgttctttt taggcatagg acccgtgtct         50

<210> SEQ ID NO 14
<211> LENGTH: 47
<212> TYPE: DNA
<213> ORGANISM: Artificial Sequence
<220> FEATURE:
<223> OTHER INFORMATION: Synthetic

<400> SEQUENCE: 14
aaggtttcat tgtccaccag gaattttag gcataggacc cgtgtct                    47

<210> SEQ ID NO 15
<211> LENGTH: 47
<212> TYPE: DNA
<213> ORGANISM: Artificial Sequence
<220> FEATURE:
<223> OTHER INFORMATION: Synthetic

<400> SEQUENCE: 15
ggttgtgata caggaaccca gagtttttag gcataggacc cgtgtct                    47

<210> SEQ ID NO 16
<211> LENGTH: 50
<212> TYPE: DNA
<213> ORGANISM: Artificial Sequence
<220> FEATURE:
<223> OTHER INFORMATION: Synthetic

<400> SEQUENCE: 16
gtccacagta gactttggga gagagatttt taggcatagg acccgtgtct                 50

<210> SEQ ID NO 17
<211> LENGTH: 46
<212> TYPE: DNA
<213> ORGANISM: Artificial Sequence
<220> FEATURE:
<223> OTHER INFORMATION: Synthetic

<400> SEQUENCE: 17
tgacatcagc cctcagcatc ttttttagg cataggaccc gtgtct                      46

<210> SEQ ID NO 18
<211> LENGTH: 49
<212> TYPE: DNA
<213> ORGANISM: Artificial Sequence
<220> FEATURE:
<223> OTHER INFORMATION: Synthetic

<400> SEQUENCE: 18
cttgtcaaat gtaactggta gccttttttt aggcatagga cccgtgtct                  49

<210> SEQ ID NO 19
<211> LENGTH: 47
<212> TYPE: DNA
<213> ORGANISM: Artificial Sequence
<220> FEATURE:
<223> OTHER INFORMATION: Synthetic

<400> SEQUENCE: 19
ctgattttga tccattgcac agattttag gcataggacc cgtgtct                     47

<210> SEQ ID NO 20
<211> LENGTH: 45
<212> TYPE: DNA
<213> ORGANISM: Artificial Sequence
<220> FEATURE:
<223> OTHER INFORMATION: Synthetic

```
<400> SEQUENCE: 20
ggcttcagga tgtccatgtt gttttttaggc ataggacccg tgtct            45

<210> SEQ ID NO 21
<211> LENGTH: 52
<212> TYPE: DNA
<213> ORGANISM: Artificial Sequence
<220> FEATURE:
<223> OTHER INFORMATION: Synthetic

<400> SEQUENCE: 21
agatgtagag tttagtgttc tcaggatttt tttaggcata ggacccgtgt ct      52

<210> SEQ ID NO 22
<211> LENGTH: 42
<212> TYPE: DNA
<213> ORGANISM: Artificial Sequence
<220> FEATURE:
<223> OTHER INFORMATION: Synthetic

<400> SEQUENCE: 22
ttttgtggct tcggccagtt tttaggcata ggacccgtgt ct                 42

<210> SEQ ID NO 23
<211> LENGTH: 46
<212> TYPE: DNA
<213> ORGANISM: Artificial Sequence
<220> FEATURE:
<223> OTHER INFORMATION: Synthetic

<400> SEQUENCE: 23
tcccaagact atgcagcaat gttttttagg cataggaccc gtgtct             46

<210> SEQ ID NO 24
<211> LENGTH: 46
<212> TYPE: DNA
<213> ORGANISM: Artificial Sequence
<220> FEATURE:
<223> OTHER INFORMATION: Synthetic

<400> SEQUENCE: 24
gtcactccag cttctcatgc tgttttagg cataggaccc gtgtct              46

<210> SEQ ID NO 25
<211> LENGTH: 46
<212> TYPE: DNA
<213> ORGANISM: Artificial Sequence
<220> FEATURE:
<223> OTHER INFORMATION: Synthetic

<400> SEQUENCE: 25
gaaacatcac ctcctgtcgc atttttagg cataggaccc gtgtct              46

<210> SEQ ID NO 26
<211> LENGTH: 43
<212> TYPE: DNA
<213> ORGANISM: Artificial Sequence
<220> FEATURE:
<223> OTHER INFORMATION: Synthetic

<400> SEQUENCE: 26
gcctggtaga tttgggtggt ttttaggcat aggacccgtg tct                43

<210> SEQ ID NO 27
<211> LENGTH: 47
<212> TYPE: DNA
```

```
<213> ORGANISM: Artificial Sequence
<220> FEATURE:
<223> OTHER INFORMATION: Synthetic

<400> SEQUENCE: 27
gcccgcagac aatacgagac acatttttag gcataggacc cgtgtct                47

<210> SEQ ID NO 28
<211> LENGTH: 45
<212> TYPE: DNA
<213> ORGANISM: Artificial Sequence
<220> FEATURE:
<223> OTHER INFORMATION: Synthetic

<400> SEQUENCE: 28
ggctttgtag ttgttgtcct cttttaggc ataggacccg tgtct                   45

<210> SEQ ID NO 29
<211> LENGTH: 43
<212> TYPE: DNA
<213> ORGANISM: Artificial Sequence
<220> FEATURE:
<223> OTHER INFORMATION: Synthetic

<400> SEQUENCE: 29
tgccattgcc tccaaagagt ttttaggcat aggacccgtg tct                    43

<210> SEQ ID NO 30
<211> LENGTH: 46
<212> TYPE: DNA
<213> ORGANISM: Artificial Sequence
<220> FEATURE:
<223> OTHER INFORMATION: Synthetic

<400> SEQUENCE: 30
aaggtttcag catcttcctc agtttttagg cataggaccc gtgtct                 46

<210> SEQ ID NO 31
<211> LENGTH: 53
<212> TYPE: DNA
<213> ORGANISM: Artificial Sequence
<220> FEATURE:
<223> OTHER INFORMATION: Synthetic

<400> SEQUENCE: 31
tgcagtaagg agttgtagag ttgtcatagt ttttaggcat aggacccgtg tct         53

<210> SEQ ID NO 32
<211> LENGTH: 48
<212> TYPE: DNA
<213> ORGANISM: Artificial Sequence
<220> FEATURE:
<223> OTHER INFORMATION: Synthetic

<400> SEQUENCE: 32
actccaaatt cttcatcaaa tcattttta ggcataggac ccgtgtct                48

<210> SEQ ID NO 33
<211> LENGTH: 46
<212> TYPE: DNA
<213> ORGANISM: Artificial Sequence
<220> FEATURE:
<223> OTHER INFORMATION: Synthetic

<400> SEQUENCE: 33
cggcttcaga gctttccaga tatttttagg cataggaccc gtgtct                 46
```

```
<210> SEQ ID NO 34
<211> LENGTH: 18
<212> TYPE: DNA
<213> ORGANISM: Artificial Sequence
<220> FEATURE:
<223> OTHER INFORMATION: Synthetic

<400> SEQUENCE: 34
gttaaagttt ccaacaac                                                 18

<210> SEQ ID NO 35
<211> LENGTH: 14
<212> TYPE: DNA
<213> ORGANISM: Artificial Sequence
<220> FEATURE:
<223> OTHER INFORMATION: Synthetic

<400> SEQUENCE: 35
tgtataaaag aagc                                                     14

<210> SEQ ID NO 36
<211> LENGTH: 21
<212> TYPE: DNA
<213> ORGANISM: Artificial Sequence
<220> FEATURE:
<223> OTHER INFORMATION: Synthetic

<400> SEQUENCE: 36
tcatgctggt gtctttctgg c                                             21

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atcttgaagc ttcaagtttg agct                                          24

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
gcaaaaatac cttgtggaga a                                             21

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
ggtcaccaag ttgaatcatc tctt                                          24

<210> SEQ ID NO 40
<211> LENGTH: 23
<212> TYPE: DNA
<213> ORGANISM: Artificial Sequence
<220> FEATURE:
<223> OTHER INFORMATION: Synthetic
```

```
<400> SEQUENCE: 40
gccacaaagc tcagaaactt ctt                                           23

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
gaacgaagta ctcgctctgc tgca                                          24

<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
aggagctgga gctgttcaca ttggtca                                       27

<210> SEQ ID NO 43
<211> LENGTH: 22
<212> TYPE: DNA
<213> ORGANISM: Artificial Sequence
<220> FEATURE:
<223> OTHER INFORMATION: Synthetic

<400> SEQUENCE: 43
ataccagttg agagacttga tc                                            22

<210> SEQ ID NO 44
<211> LENGTH: 24
<212> TYPE: DNA
<213> ORGANISM: Artificial Sequence
<220> FEATURE:
<223> OTHER INFORMATION: Synthetic

<400> SEQUENCE: 44
atacaggatc ttcccaacga gcag                                          24

<210> SEQ ID NO 45
<211> LENGTH: 25
<212> TYPE: DNA
<213> ORGANISM: Artificial Sequence
<220> FEATURE:
<223> OTHER INFORMATION: Synthetic

<400> SEQUENCE: 45
gccttgtggc tggagtgtca ggtgt                                         25

<210> SEQ ID NO 46
<211> LENGTH: 23
<212> TYPE: DNA
<213> ORGANISM: Artificial Sequence
<220> FEATURE:
<223> OTHER INFORMATION: Synthetic

<400> SEQUENCE: 46
acagccagtt cctggaaggt ctt                                           23
```